United States Patent
Arditi et al.

(10) Patent No.: US 9,512,196 B2
(45) Date of Patent: *Dec. 6, 2016

(54) SHORT-FORM HUMAN MD-2 AS A NEGATIVE REGULATOR OF TOLL-LIKE RECEPTOR 4 SIGNALING

(71) Applicant: Cedars-Sinai Medical Center, Los Angeles, CA (US)

(72) Inventors: Moshe Arditi, Encino, CA (US); Pearl S. Gray, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/639,782

(22) Filed: Mar. 5, 2015

(65) Prior Publication Data

US 2015/0218246 A1    Aug. 6, 2015

Related U.S. Application Data

(63) Continuation-in-part of application No. 14/010,362, filed on Aug. 26, 2013, now abandoned, which is a continuation of application No. 13/051,390, filed on Mar. 18, 2011, now Pat. No. 8,546,324, which is a continuation-in-part of application No. PCT/US2009/050317, filed on Jul. 10, 2009.

(60) Provisional application No. 61/098,861, filed on Sep. 22, 2008.

(51) Int. Cl.
| | |
|---|---|
| A61K 38/16 | (2006.01) |
| A61K 38/17 | (2006.01) |
| C07K 14/705 | (2006.01) |
| C07K 14/435 | (2006.01) |
| C07K 14/47 | (2006.01) |

(52) U.S. Cl.
CPC ........... *C07K 14/705* (2013.01); *A61K 38/177* (2013.01); *A61K 38/16* (2013.01); *C07K 14/435* (2013.01); *C07K 14/47* (2013.01)

(58) Field of Classification Search
None
See application file for complete search history.

(56) References Cited

U.S. PATENT DOCUMENTS

| | | | |
|---|---|---|---|
| 5,591,227 | A | 1/1997 | Dinh et al. |
| 5,733,327 | A | 3/1998 | Igaki et al. |
| 6,171,609 | B1 | 1/2001 | Kunz |
| 6,297,011 | B1 | 10/2001 | Greenspan et al. |
| 6,306,663 | B1 | 10/2001 | Kenten et al. |
| 6,323,334 | B1 | 11/2001 | Kingsbury et al. |
| 7,312,320 | B2 | 12/2007 | Elson |
| 7,959,918 | B2 | 6/2011 | Arditi et al. |
| 8,546,324 | B2 | 10/2013 | Arditi et al. |
| 2003/0077279 | A1 | 4/2003 | Arditi et al. |
| 2003/0148986 | A1 | 8/2003 | Arditi et al. |
| 2003/0232352 | A1 | 12/2003 | Schwartz et al. |
| 2008/0286285 | A1 | 11/2008 | Arditi et al. |
| 2014/0045775 | A1 | 2/2014 | Arditi et al. |

FOREIGN PATENT DOCUMENTS

| | | |
|---|---|---|
| EP | 1302206 A2 | 4/2003 |
| EP | 1355150 A2 | 10/2003 |
| EP | 1455829 A0 | 9/2004 |
| JP | 2005507920 A | 3/2005 |
| JP | 2005512636 A | 5/2005 |
| JP | 2007534775 A | 11/2007 |
| WO | WO 94/16706 A1 | 8/1994 |
| WO | WO 98/50547 A2 | 11/1998 |
| WO | WO 00/20019 A2 | 4/2000 |
| WO | WO 00/24776 A1 | 5/2000 |
| WO | WO 00/72023 A2 | 11/2000 |
| WO | WO 01/72993 A1 | 4/2001 |
| WO | WO 01/36488 A1 | 5/2001 |
| WO | WO 01/43691 A2 | 6/2001 |
| WO | WO 01/55386 A1 | 8/2001 |
| WO | WO 01/88137 A2 | 11/2001 |
| WO | WO 03/35110 A1 | 5/2003 |
| WO | WO 03/050137 A2 | 6/2003 |
| WO | WO 03/051396 A1 | 6/2003 |
| WO | WO 2004/023973 A2 | 3/2004 |
| WO | WO 2004/031225 A1 | 4/2004 |
| WO | WO 2004/093778 A2 | 11/2004 |
| WO | WO 2005/117975 A2 | 12/2005 |
| WO | WO 2006/005035 A2 | 1/2006 |

(Continued)

OTHER PUBLICATIONS

Buckley et al. The influence of dysfunctional signaling and lipid homeostasis in mediating the inflammatory responses during atherosclerosis. Biochim Biophys Acta 1852: 1498-1510, 2015.*
Elsner et al. Chemokine receptor antagonists: a novel therapeutic approach in allergic diseases. Allergy 59: 1243-1258, 2004.*
Furler et al. Signaling through the P38 and ERK pathways: a common link between HIV replication and the immune response. Immunol Res 48: 99-109, 2010.*
Herbein et al. Macrophage signaling in HIV infection. Retrovirol :34, 2010 (13 total pages).*

(Continued)

*Primary Examiner* — Bridget E Bunner
(74) *Attorney, Agent, or Firm* — Nixon Peabody LLP; Linda B. Huber

(57) ABSTRACT

The present invention is based on a novel, alternatively spliced human isoform of MD-2 (MD-2s). In addition, the present invention relates to modified MD-2 proteins, wherein one or more tyrosine residues have been mutated to phenylalanine. In various embodiments, the invention relates to methods and kits for preventing, reducing the likelihood of developing and/or treating various conditions using MD-2s. The invention also describes methods of determining the risk of a subject to various conditions.

14 Claims, 29 Drawing Sheets

(5 of 29 Drawing Sheet(s) Filed in Color)

(56) References Cited

FOREIGN PATENT DOCUMENTS

| WO | WO 2006/025995 A2 | 3/2006 |
|---|---|---|
| WO | WO 2008/016356 A2 | 2/2008 |
| WO | WO 2008/067195 A2 | 6/2008 |
| WO | WO 2009/059143 A2 | 5/2009 |
| WO | WO 2010/033294 A1 | 3/2010 |

OTHER PUBLICATIONS

Hosoki et al. Myeloid differentiation protein 2 facilitates pollen— and cat dander-induced innate and allergic airway inflammation. J Allergy Clin Immunol (http://dx.doi.org/10.1016/j.jaci.2015.09.036); available online Nov. 15, 2015, 10 total pages.*

Juno et al. Clarifying the role of G protein signaling in HIV infection: new approaches to an old question. AIDS Rev 12: 164-176, 2010.*

Lee et al. Transgenic mice which overproduce Th2 cytokines develop spontaneous atopic dermatitis and asthma. Int Immunol 16(8): 1155-1160, 2004.*

Yao et al. Pathophysiological aspects of sepsis: an overview. Methods Mol Biol 1237: 5-15, 2015.*

PCT/US2002/034120 International Search Report dated Feb. 28, 2003.

PCT/US2002/034120 Written Opinion dated Jun. 10, 2003.

PCT/US2002/034120 International Preliminary Examination Report dated Aug. 28, 2003.

PCT/US2002/039932 International Search Report dated Feb. 28, 2003.

PCT/US2002/039932 Written Opinion dated Aug. 11, 2003.

PCT/US2002/039932 International Preliminary Examination Report dated Nov. 5, 2003.

PCT/US2005/018604 International Search Report dated Feb. 28, 2006.

PCT/US2005/018604 Written Opinion dated Feb. 28, 2006.

PCT/US2005/018604 International Preliminary Report on Patentability dated Feb. 2, 2006.

PCT/US2009/050317 International Search Report dated Dec. 10, 2009.

PCT/US2009/050317 Written Opinion dated Dec. 10, 2009.

PCT/US2009/050317 International Preliminary Report on Patentability dated Mar. 22, 2011.

EP Application No. 05760412.6 Supplementary Search Report dated Jun. 3, 2008.

EP Application No. 09814939.6 Extended Search Report dated Feb. 12, 2012.

Agencourt 6708521 NIH_MGC_120 Homo sapiens cDNA clone, Image: 5747232 5, mRNA seqence. Retrieved from EBI accession No. EM_EST: BM918324. Mar. 15, 2002.

Agrawal et al. Antisense Therapeutics: is it as simple as complementary base recognition? Molecular Medicine Today. (2000). 6::72-81.

Akashi et al. Lipopolysaccharide Interaction with Cell Surface Toll-like Receptor 4-MD-2: Higher Affinity than that with MD-2 or CD14. Exp. Med. (2003). 198(70):1035-1042.

Bartfai, T. et al. A low molecular weight mimic of the Toll/IL-1 receptor/resistance domain inhibits IL-1 receptor-mediated responses. PNAS. (2003). 100(13):7971-7976.

Bernstein et al. Role for a bidentate ribonuclease in the initiation step of RNA interference. Nature. (2001). 409(6818):363-366. ABSTRACT ONLY.

Bjorkbacka, H. et al. Reduced atherosclerosis in MyD88-null mice links elevated serum cholesterol levels to activation of innate immunity signaling pathways. Nature Immunology (2004). 10(4): 416-421.

Bowie, A. et al. A46R and A52R from vaccinia virus are antagonists of hot IL-1 and toll-like receptor signaling. PNAS (2000). 97(18): 10162-10167.

Branch, A.D. A good antisense molecule is hard to fmd. Trends in Biochem. Sci (TIBS). (1998). 23:45-50.

Brint, E.K. et al. ST2 is an inhibitor of interleukin 1 receptor and Toll-like receptor 4 signaling and maintains endotoxin tolerance. Nature Immunology (2004). 5(4): 373-379.

Bulut et al. Chlamydial Heat Shock Protein 60 Activates Macrophags and Endothelial Cells Through Toll-Like Receptor 4 and MD2 in a MyD88-Dependent Pathway. Journal of Immunology. (2002). 168:1435-1440.

Burns, K. et al. MyD88, an adapter protein involved in interleukin-1 signaling. The Journal of Biological Chemistry. (1998). 273(20): 12203-12209.

Chirila et al. The Use of Synthetic Polymers for Delivery of Therapeutic Antisense Oligodeoxynucleotides. Biomaterials. (2002). 23:321-342.

Derossi et al. The Third Helix of the Antennapedia Homeodomain Translocates Through Biological Membranes. The Journal of Biological Chemistry. (1994). 289(14):10444-10450.

Edfeldt et al. Expression of Toll-LIke Receptors in Human Atheroscerotic Lesions: A Possible Pathway for Plaque Activation. Circulation (2002). 105:1158-1161.

Elbashir et al. RNA interference is mediated by 21—and 22-nucleotode RNAs. Genes and Development (2001). 15:188-200.

Erridge, C. Endogenous ligands of TLR2 and TLR4: agonists or assistants? Journal of Leukocyte Biology (2010). 87:989-999.

Fitzgerald, K. et al. Mal (MyD88-adapter-like) is required for Toll-like receptor-4 signal transduction. Nature. (2001). 413:78-83.

Fort, M.M. et al. A Synthetic TLR4 Antagonist has Anti-Inflammatory Effects in two Murine Models of Inflammatory Bowel Disease. The Journal of Immunology (2005). 174:6416-6423.

Gray et al. Identification of a Novel Human MD-2 Splice Variant that Negatively Regulates Lipopolysaccharide-Induced TLR4 Signaling. The Journal of Immunology (2012). 184:6359-6366, pre-published online Apr. 30, 2010.

Gupta, B. et al. Intracellular delivery of large molecules and small particles by cell-penetrating proteins and peptides.Advanced Drug Delivery Reviews. (2005). 57:637-651.

Hamann et al. A coding mutation within the first exon of the human MD-2 gene results in decreased lipopolysaccharide-induced signaling. Genes and Immunity (2004). 5:283-2888.

Hammond et al. An RNA-directed nuclease mediates post-transcriptional gene silencing in Drosophila cells. Nature. (2000). 404:293-296. ABSTRACT ONLY.

Hanada et al. Regulation of cytokine signaling and inflammation. Cytokine and Growth Factor Reviews. (2002). 13:413-421.

Kiechl, S. et al. Toll-like receptor 4 polymorphisms and atherogenesis. New England Journal of Medicine. (2002). 347(3):185-192.

Kennedy et al. A Complex of Soluble MD-2 and Lipopolysaccharide Serves as an Activation Ligand for Toll-like Receptor 4. J Biol Chem (2004). 279(33):34698-34704.

Kim et al. Crystal Structure of the TLR4-MD-2 Complex with Bound Endotoxin Antagonist Eritoran. Cell (2007). 130, 906-917.

Means et al. Differential Effects of a Toll-Like Receptor Antagonist on Mycobacterium tuberculosis-Induced Macrophage Responses. Journal of Immunology. (2001). 166(6):4074-4082.

Mita et al. Toll-Like Receptor 2 and 4 Surface expressions on Human Monocytes and Modulated by Interferon-Gamma and Macrophage Colony-Stimuating Factor. Immunol Lett. (2001) 78:97-101. ABSTRACT.

Ohta et al. Identification of a novel isoform of MD-2 that downregulates lipopolysaccharide signaling. Biochemical and Biophysical Research Communications. (2004). 323, 1103-1108.

O'Neill et al. Therapeutic Targeting of Toll-Like Receptors for Infectious and Inflammatory Diseases and Cancer. Pharmacol Rev. (2009). 61(2):177-197.

Pasterkamp, G. et al. Role of Toll-like receptor 4 in the initiation and progression of atherosclerotic disease. Eur J. Clin Invest. (2004). 34(5):328-334.

Peracchi, A. Prospects for Antiviral Ribozymes and Deoxyribozymes. Revies in Medical Virology. (2004). 14:47-64.

Prebeck et al. Predominant Role of Toll-Like Receptor 2 versus 4 in Chamydia Pneumoniae-Induced Activation of Dendritic Cells. J. Immun. (2001). 167(6):3316-3323.

(56) References Cited

OTHER PUBLICATIONS

Pooga et al. Cell Penetration by Transportation. FASEB J. (1998). 12:67-77.

Re et al. Separate Functional Domains of Human MD-2 Mediate Toll-Like Receptor 4-Binding and Lipopolysaccharide Responsiveness. J Immunol (2003). 171:5272-5276.

Ronni, T. et al. Common Interaction Surfaces of the Toll-Like Receptor 4 Cytoplasmic Domain Stimulate Multiple Nuclear Targets. Molecular and Cellular Biology. (2003). 23(7): 2543-2555.

Sasu et al. *Clamydia pneumoniae* and Chlamydial Heat Shock Protein 60 Stimulate Proliferation of Human Vascular Smooth Muscle Cells via Toll-Like Receptor 4 and p44/p42 Mitogen-Activated Protein Kinase Activation. Circulation Research (2001). 89(3):244-250.

Sharp, P.A. RNA interference. Genes and Development (2001). 15:485-490.

Shimazu et al. MD-2, a Molecule that Confers Lipopolysaccharide Responsiveness on Toll-like Receptor 4. J. Exp. Med. (1999). 189(11):1777-1782.

Tabeta et al. Toll-Like Receptors Confer Responsiveness to Lipopolysaccharide from Porphyromonas gingivalis in Human Gingival Fibroblasts. Infection and Immunity. (2000). 68(6): 3731-3735.

Thomas et al. HEK293 cell line: A vehicle for the expression of recombinant proteins. Journal of Pharmacological and Toxicological Methods (2005). 51:187-200.

Uehori et al. Simultaneous Blocking of Human Toll-Like Receptors 2 and 4 Suppresses Myeloid Dendritic Cell Activation Induced by *Mycobacterium bovis* Bacillus Calmette-Guerin Peptidoglycan. Infection and Immunity. (2003). 71(8):4238-4249.

Uesugi et al. Toll-Like Receptor 4 is Involved in the Mechanism of Early Alcohol-Induced Liver Injury in Mice. Heptalogy. (2001). 34(1): 101-108.

Ulevitch, R. et al. Therapeutics targeting the innate immune system. Nature Reviews. Immunology (2004). 4:512-520.

Vabulas et al. Endocytosed HSP6Os Use Toll-Like Receptor 2 (TLR2) and TLT4 to Activate the Toll/Interleukin-1 Receptor Signaling Pathway in Innate Immune Cells. J. Biol. Chem. (2001). 276(33): 31332-31339.

Van Tassell, B.W. et al. Pharmacologic Inhibition of Myeloid Differentiation Factor 88 (MyD88) Prevents Left Ventricular Dilation and Hypertrophy after Experimental Acute Myocardial Infarction in the Mouse. Journal of Cardiocasc Pharmacology. (2010). 55(4):385-390.

Vasl et al. Functional Activity of MD-2 Polymorphic Variant is Significantly Different in Soluble and TLR4Bound Forms: Decreased Endotoxin Binding by G56R MD-2 and its Rescue by TLR4 Ectodomain. J Immunol (2008). 180:6107-6115.

Xu, X.H et al. Toll-like Receptor-4 is Expressed in Human Coronary Atherosclerotic Plaques and Upregulated by Oxidized Low Density Lipoprotein in Macrophages. Journal of the American College of Cardiology (2000). 35(2) Suppl A. ABSTRACT ONLY.

Xu et al. Toll-Like Receptor-4 is Expressed by Macrophages in Murine and Human Lipid-Rick Atherosclerotic Plaques and Upregulated by Oxidized LDL. Circulation (2001). 104:3103-3108.

Zuany-Amorim, C. et al. Toll-like receptors as potential therapeutic targets for multiple diseases. Nature Reviews. Drug Discovery (2002). 1:797-807.

Crooke, S.T. Antisense Research and Application. Springer-Verlag (1998). Chapters 1 and 2. pp. 1-50.

\* cited by examiner

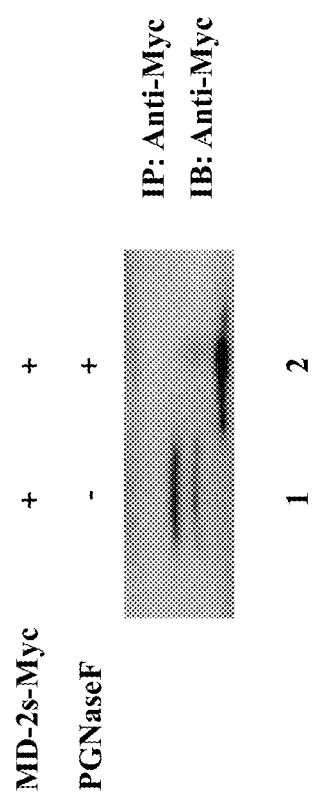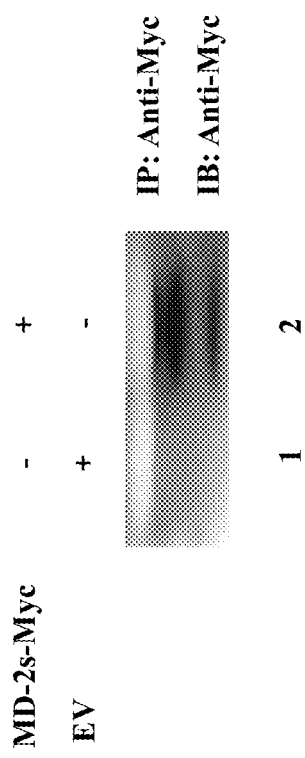
FIG. 2A
FIG. 2B

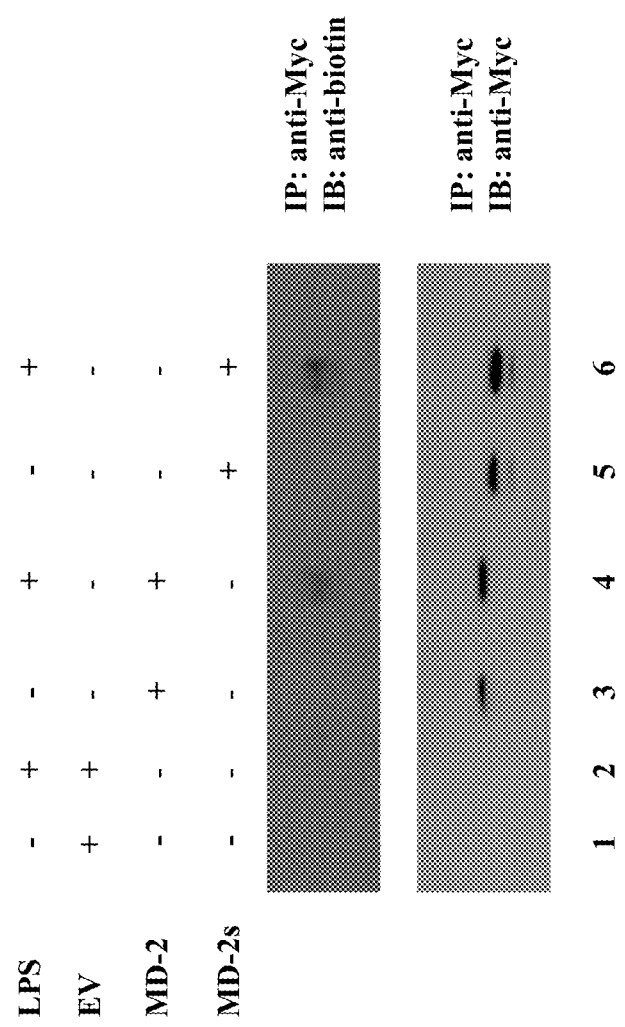

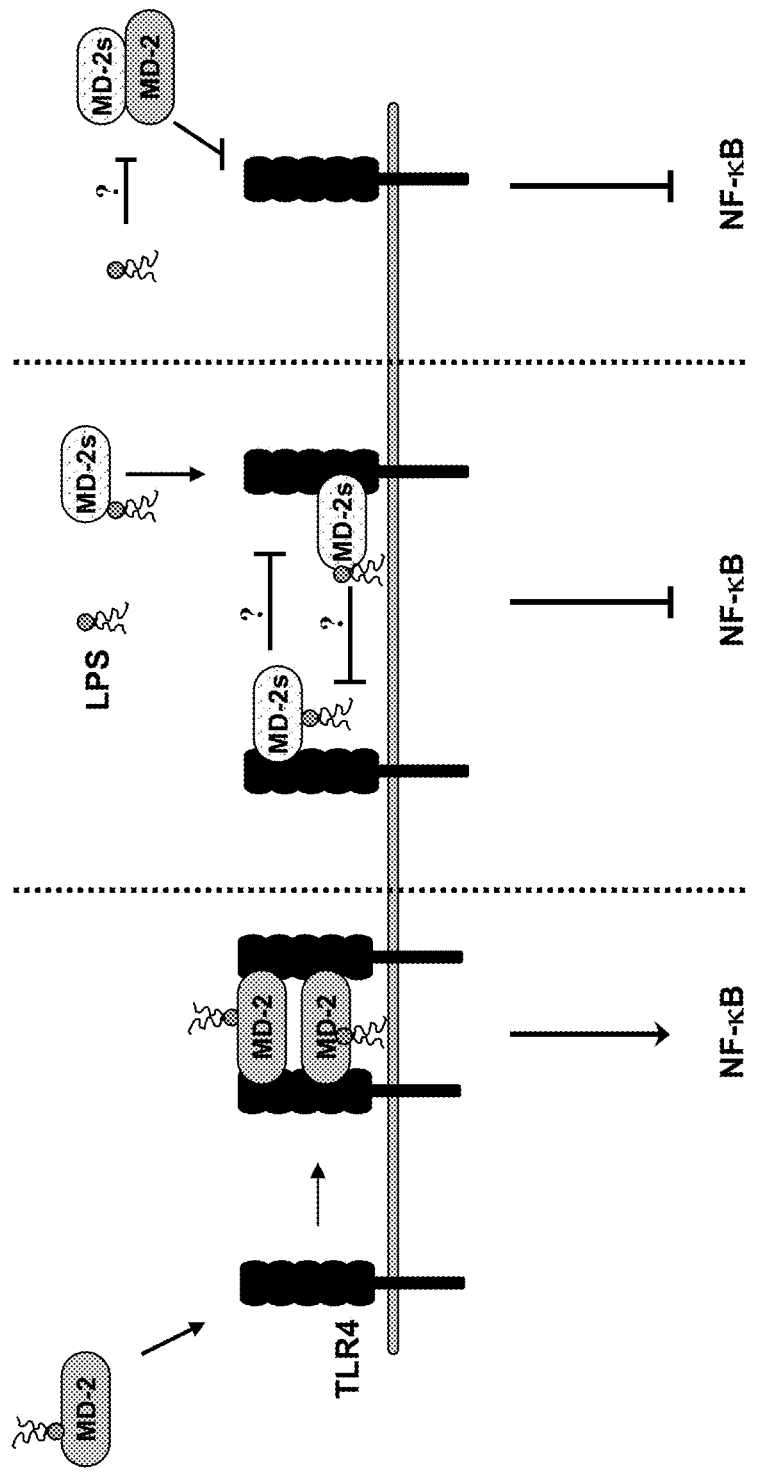

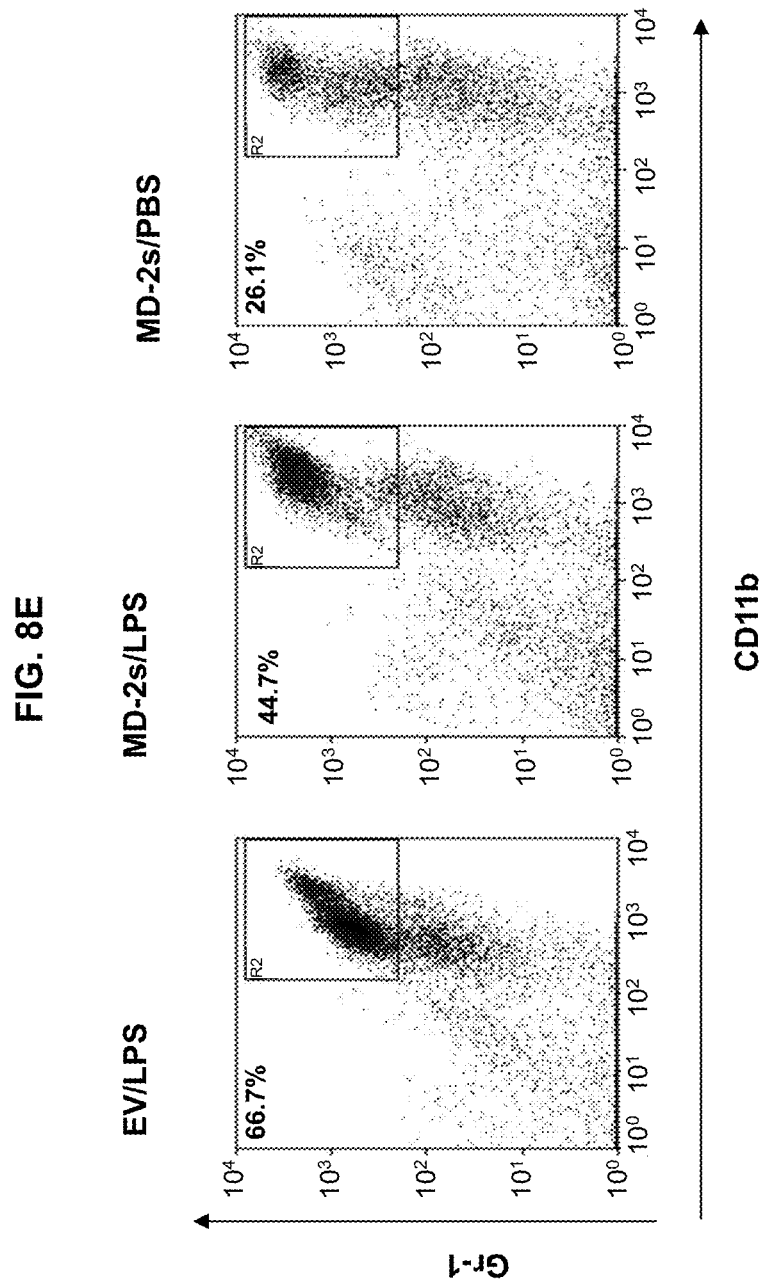

FIG. 12A
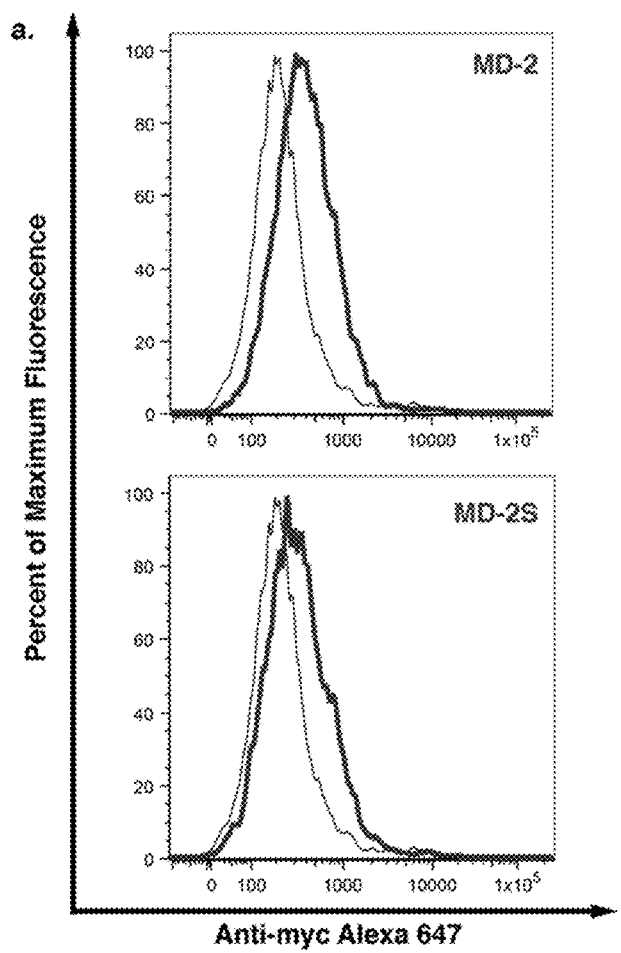
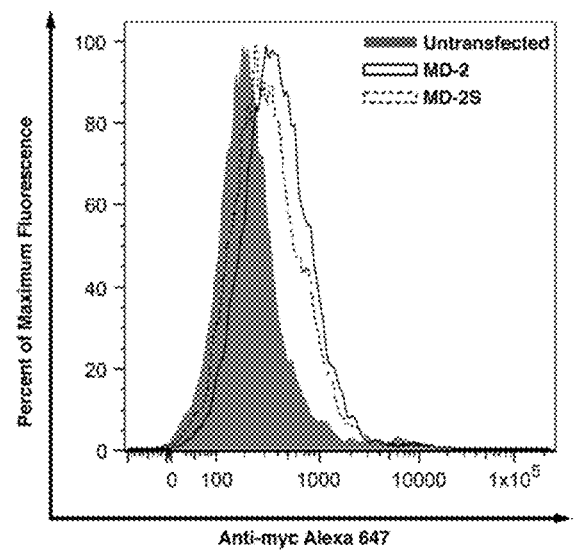

FIG. 13
A
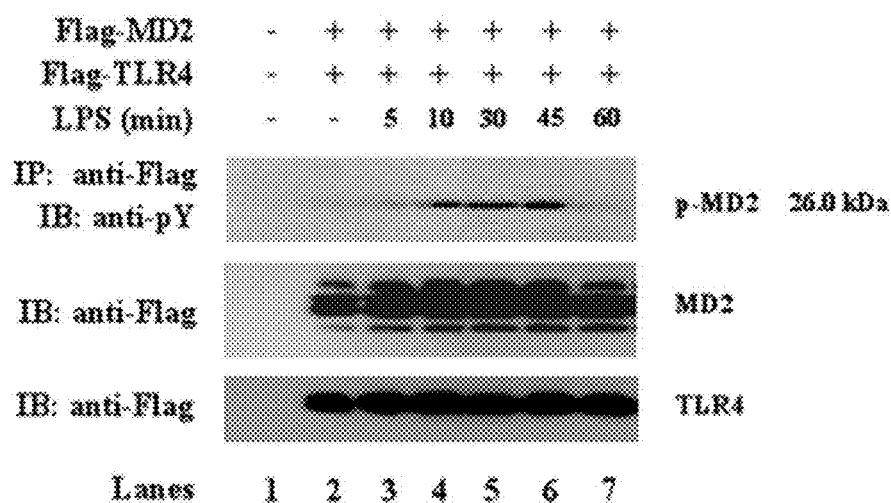
B
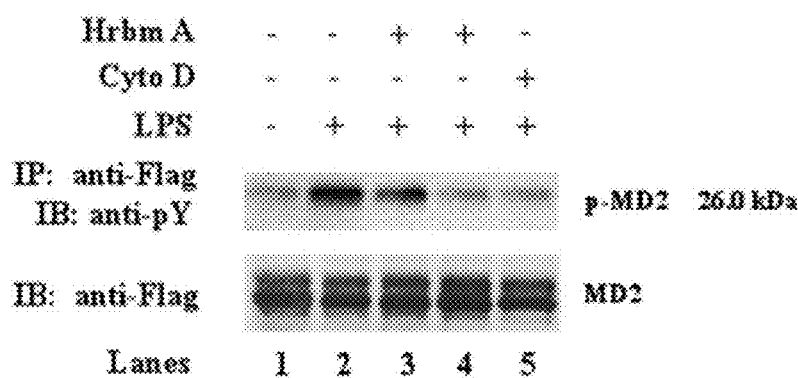

FIG. 16
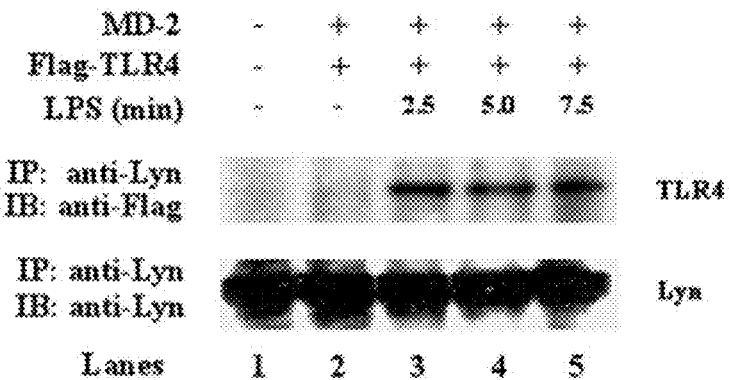
A
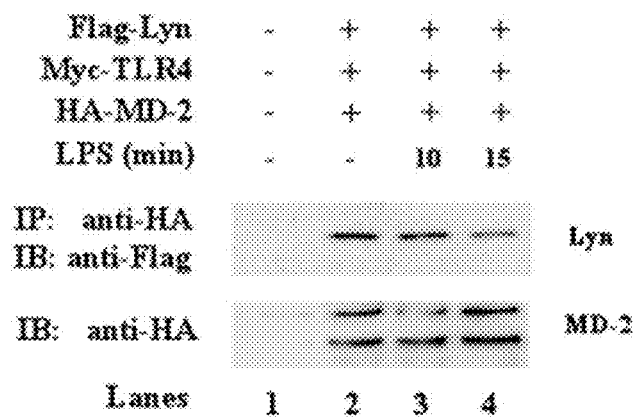
B
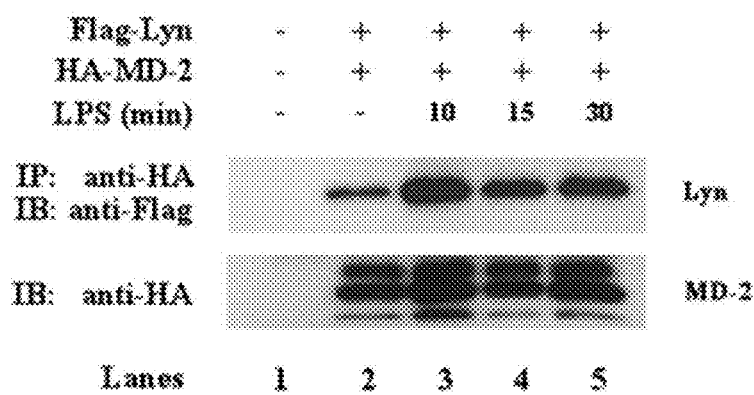
C

FIG. 17
A
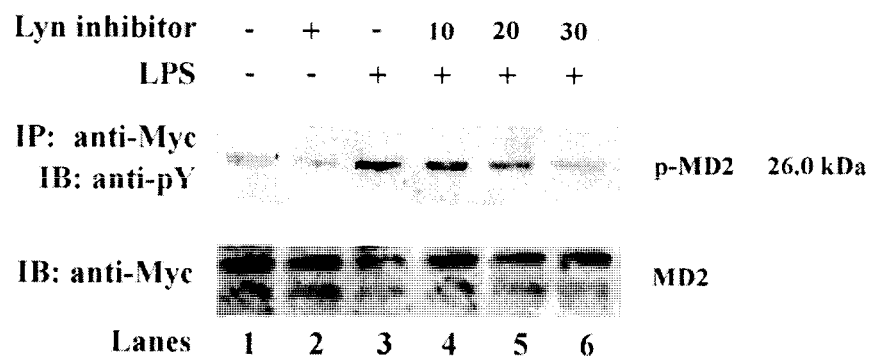
B
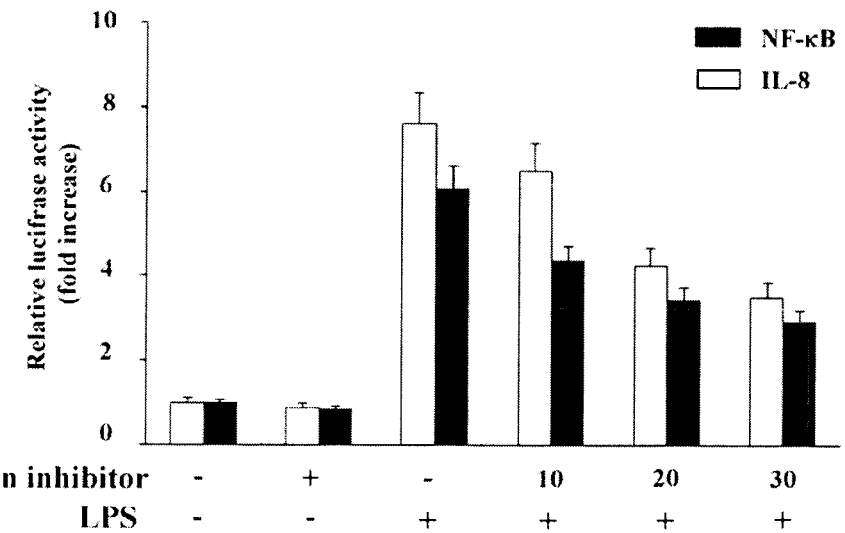

SHORT-FORM HUMAN MD-2 AS A NEGATIVE REGULATOR OF TOLL-LIKE RECEPTOR 4 SIGNALING

CROSS-REFERENCE TO RELATED APPLICATIONS

This application is a continuation-in part of application Ser. No. 14/010,362, filed Aug. 26, 2013, now abandoned, which is a continuation of application Ser. No. 13/051,390, filed Mar. 18, 2011, and issued as U.S. Pat. No. 8,546,324 on Oct. 1, 2013, which is a continuation in part of International Application PCT/US09/50317, filed Jul. 10, 2009, which designated the U.S. and that International Application was published under PCT Article 21(2) in English, which claims the priority of U.S. Provisional Patent Application No. 61/098,861, filed Sep. 22, 2008.

STATEMENT REGARDING FEDERALLY-SPONSORED RESEARCH

This invention was made with Government support under Grant Nos. AI058128 and HL066436 awarded by the National Institute of Health. The Government has certain rights in the invention.

FIELD OF INVENTION

This invention relates to myeloid differentiation-2 and its role in toll-like receptor 4 and lipopolysaccharide signaling.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Microbial detection and instigation of an appropriate innate and subsequent adaptive immune response to a pathogenic assault, is highly reliant on toll-like receptors (TLRs) (Brikos et al. (2008) HANDB EXP PHARMACOL, 21-50). Members of the TLR family recognize specific conserved pathogen-associated molecular patterns (PAMPs) expressed by invading microorganisms. TLR4, one of the most widely studied TLRs, recognizes a repertoire of PAMPs, which includes lipopolysaccharide (LPS), a major component of the outer membrane of Gram-negative bacteria (Poltorak et al. (1998) SCIENCE 282, 2085-2088; Qureshi et al. (1999) J EXP MED 189, 615-625; Hoshino et al. (1999) J IMMUNOL 162, 3749-3752; Medzhitov et al. (1997) NATURE 388, 394-397). For optimal LPS-induced signal transduction to occur, a receptor complex is assembled consisting of the signaling subunit TLR4, the co-receptor myeloid differentiation (MD)-2, and two accessory proteins, LPS-binding protein (LBP) and CD14 (Schumann et al. (1990) SCIENCE 249, 1429-1431; Pugin et al. (1993) PROC NATL ACAD SCI USA 90, 2744-2748; Frey et al. (1992) J EXP MED 176, 1665-1671; Shimazu et al. (1999) J EXP MED 189, 1777-1782).

MD-2 belongs to the MD-2-related lipid recognition (ML) family (Inohara et al. (2002) TRENDS BIOCHEM SCI 27, 219-221). A secretion signal, the signature sequence of this group of proteins, is located at the N-terminal domain of MD-2 (Kato et al. (2000) BLOOD 96, 362-364). Although MD-2 lacks transmembrane and intracellular regions, it may be membrane-bound through its association with the extracellular portion of TLR4 (Akashi et al. (2000) J IMMUNOL 164, 3471-3475). Studies with mice deficient in either MD-2 or that lacked a functional TLR4 have revealed that both proteins are absolutely required for LPS signaling (Poltorak et al. (1998) SCIENCE 282, 2085-2088; Qureshi et al. (1999) J EXP MED 189, 615-625; Hoshino et al. (1999) J IMMUNOL 162, 3749-3752; Shimazu et al. (1999) J EXP MED 189, 1777-1782). Although TLR4 is critical to mount a response to gram-negative bacteria, tight regulation of the TLR4 signal transduction pathway is imperative to prevent excessive inflammation that could lead to collateral damage to the host (Liew et al. (2005) NAT REV IMMUNOL 5, 446-458). One method of control involves alternative splicing of specific genes that encode essential components of the TLR4 signaling pathway to produce inhibitory isoforms, examples include myeloid differentiation factor $88_S$ (MyD$88_S$) (Janssens et al. (2002) CURR BIOL 12, 467-471), and smTLR4 (Iwami et al. (2000) J IMMUNOL 165, 6682-6686; Jaresova et al. (2007) MICROBES INFECT 9, 1359-1367). Similarly, the murine MD-2 gene encodes two alternatively spliced isoforms. The truncated variant, MD-2B, generated by the splicing out of the first 54 amino acids of exon 3, down-regulates LPS signaling (Ohta et al. (2004) BIOCHEM BIOPHYS RES COMMUN 323, 1103-1108). Given that mouse and human MD-2 are highly conserved, an alternative splicing of this gene in humans could also play an important regulatory role in humans.

There is still a need for therapeutic strategies that may be used to treat human pathologies characterized by an overly exuberant or chronic immune response to LPS. Therefore, novel mechanisms to further regulate TLR4 signaling would be beneficial and the protein MD-2s described herein may be used to treat these human pathologies.

SUMMARY OF THE INVENTION

The following embodiments and aspects thereof are described and illustrated in conjunction with compositions and methods which are meant to be exemplary and illustrative, not limiting in scope.

Various embodiments of the present invention provide for a method of inhibiting toll-like receptor 4 signaling ("TLR4"), inhibiting lipopolysaccharide ("LPS") signaling, treating a condition mediated by TLR4 signaling, or reducing a likelihood of developing a condition mediated by TLR4 signaling in a subject in need thereof, comprising: providing a purified polypeptide comprising an amino acid sequence that is at least 80% identical to SEQ ID NO:1 or SEQ ID NO:2; and administering the polypeptide to the subject to inhibit TLR4 signaling, inhibit LPS signaling, treat the condition mediated by TLR4 signaling, or reduce the likelihood of developing the condition mediated by TLR4 signaling.

In various embodiments, the condition mediated by TLR signaling can be selected from the group consisting of sepsis, septic shock, inflammation, gram negative bacterial infection, lung inflammation, gram negative bacterial lung infection, immune response, atherosclerosis, asthma, viral infection and combinations thereof.

In various embodiments, the polypeptide can comprise the amino acid sequence as disclosed by SEQ ID NO:1 or SEQ ID NO:2. In various embodiments, the polypeptide can be glycosylated. In various embodiments, the polypeptide can comprise the amino acid sequence of SEQ ID NO:1 or SEQ ID NO:2 and 1-20 conservative amino acid substitutions. In various embodiments, the polypeptide can comprise the amino acid sequence of SEQ ID NO:1 or SEQ ID NO:2 and 1-20 amino acid insertions, deletions and/or substitutions.

Various embodiments provide for a method of inhibiting lipopolysaccharide ("LPS") induced lung inflammation in a subject in need thereof, comprising: providing a purified polypeptide comprising an amino acid sequence that is at least 85% identical to SEQ ID NO:1 or SEQ ID NO:2; and administering the polypeptide to the subject to inhibit LPS induced lung inflammation.

In various embodiments, the polypeptide can comprise the amino acid sequence of SEQ ID NO:1. In various embodiments, the polypeptide can be glycosylated. In various embodiments, the polypeptide can comprise the amino acid sequence of SEQ ID NO:2. In various embodiments, the purified polypeptide comprising an amino acid sequence can be at least 90% identical to SEQ ID NO:1 or SEQ ID NO:2. In various embodiments, the purified polypeptide comprising an amino acid sequence can be at least 95% identical to SEQ ID NO:1 or SEQ ID NO:2. In various embodiments, the purified polypeptide comprising an amino acid sequence can be at least 99% identical to SEQ ID NO:1 or SEQ ID NO:2.

Various embodiments provide for a method of treating asthma, allergic asthma, house dust mite (HDM)-induced allergic airway inflammation, perennial rhinitis, or atopic dermatitis (AD) in a subject in need thereof, comprising: providing a purified polypeptide comprising an amino acid sequence that is at least 85% identical to SEQ ID NO:1 or SEQ ID NO:2; and administering the polypeptide to the subject to treat asthma, allergic asthma, house dust mite (HDM)-induced allergic airway inflammation, perennial rhinitis, or atopic dermatitis (AD).

In various embodiments, the polypeptide can comprise the amino acid sequence of SEQ ID NO:1. In various embodiments, the polypeptide can be glycosylated. In various embodiments, the polypeptide can comprise the amino acid sequence of SEQ ID NO:2. In various embodiments, the purified polypeptide comprising an amino acid sequence can be at least 90% identical to SEQ ID NO:1 or SEQ ID NO:2. In various embodiments, the purified polypeptide comprising an amino acid sequence can be at least 95% identical to SEQ ID NO:1 or SEQ ID NO:2. In various embodiments, the purified polypeptide comprising an amino acid sequence can be at least 99% identical to SEQ ID NO:1 or SEQ ID NO:2.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

The patent or application file contains at least one drawing executed in color. Copies of this patent or patent application publication with color drawing(s) will be provided by the Office upon request and payment of the necessary fee.

Exemplary embodiments are illustrated in referenced figures. It is intended that the embodiments and figures disclosed herein are to be considered illustrative rather than restrictive.

FIGS. 2A-2B show that MD-2s is N-linked glycosylated and secreted in accordance with an embodiment of the present invention. (A) Myc-MD-2s was immunoprecipitated (IP) from cell lysates prepared from HEK293 cells transiently transfected with a plasmid encoding Myc-MD-2s. Immunoprecipitants were either left untreated (lane 1) or treated with peptide N-glycosidase F (PNGase F) (lane 2). Samples were subsequently analyzed by SDS-PAGE and immunoblotted with an anti-Myc antibody. (B) Myc-MD-2s was immunoprecipitated (IP) from culture supernatants that were obtained from HEK293 cells transiently transfected with a plasmid encoding Myc-MD-2s. Samples were subsequently analyzed by SDS/PAGE and immunoblotted (IB) with an anti-Myc antibody. Mock transfected culture supernatants were used as a negative control.

FIGS. 6A-6C show that MD-2s interacts with wild-type MD-2 and LPS in accordance with an embodiment of the present invention. (A) HEK293 cells were transiently transfected with plasmids encoding for Flag-tagged MD-2 (lanes 1-4) in combination with either a Myc-tagged MD-2 (lanes 1 and 3) or a Myc-tagged MD-2s (lanes 2 and 4) expressing plasmid. Co-immunoprecipitation experiments were then performed using an anti-Flag antibody (lanes 3-4) or an IgG isotype control antibody (lane 1-2). Samples were fractionated by SDS-PAGE and immunoblotting with an anti-Myc antibody was performed. (B) Structural analysis of MD-2. Structural features representing the TLR4 binding sites (red); the ligand contacts (dark blue); the ligand binding pocket (light blue) and the TLR4 secondary contacts (pink) are illustrated. The residues deleted in MD-2s (yellow) are also shown. (C) HEK293 cells were transiently transfected with plasmids encoding for Myc-tagged MD-2 (lanes 3 and 4) or a Myc-tagged MD-2s (lanes 5 and 6) expressing plasmid and treated with LPS-biotin as indicated. Co-immunoprecipitation experiments were then performed using an anti-Myc antibody. Samples were fractionated by SDS-PAGE and immunoblotting with an anti-biotin (upper panel) and anti-Myc antibody (lower panel) were performed.

FIG. 7 depicts schematic diagram representing the possible mechanisms employed by which MD-2s negatively regulates LPS signaling in accordance with an embodiment of the present invention.

FIGS. 8A-8E show that MD-2s inhibits lung inflammation induced by LPS in vivo in accordance with an embodiment of the present invention. (A) MD-2s expression can be detected following in vivo transfection. RNA was isolated from lung tissue of wild-type mice at 48 h post in vivo transfection with control vector (lane 1), Myc-MD2 (lane 2) or a plasmid encoding MycMD-2s (lane 3) and reverse transcribed into cDNA. RT-PCR using human MD-2-specific primers (lanes 1-3) or murine GAPDH primers (lanes 4-6), was then performed. (B-E) Wild-type mice were transfected with control vector (EV, open bars) or a plasmid encoding MD-2s (black bars) 48 h before being challenged intratracheally with PBS or 10 μg of LPS, for 24 h. MD-2s expression reduced (B) IL-6 concentration in bronchoalveolar lavage fluid (BALF), (C) KC concentration in the lung homogenate, and (D) recruitment of polymorphonuclear leukocytes (PMN) into the lung. (E) Flow cytometry analysis demonstrated that following LPS challenge the percentage of GR-1$^+$CD11b$^+$ cells in the lung decreased from 66.7% to 26.1% with MD-2s expression.

FIGS. 12A-12B shows that MD-2 and MD-2S bind to the surface of TLR4-expressing cells in accordance with an embodiment of the present invention. HEK293T cells stably expressing fluorescent TLR4-mCitrine were transiently transfected with myc-tagged wild-type MD-2 or MD-2s and surface-stained with anti-myc antibody. (a) Cells analyzed by flow cytometry were gated to select single cells and the TLR4-positive population. Anti-myc staining of TLR4-mCitrine positive cells expressing MD-2 (top panel, thick line) or MD-2s (middle panel, thick line) and untransfected cells (thin line) is shown. (b) Confocal imaging shows that a subpopulation of cells expressing mCitrine-tagged TLR4 (green) co-express transfected MD-2 (red, top panel) or MD-2S (red, bottom panel). Co-localization of TLR4 and MD-2 isoforms on the cell surface is visualized in yellow.

FIG. 13 shows that MD-2 is tyrosine phosphorylated and that this phosphorylation is inhibited by herbimycin A and cytochalasin D. (A) HEK293 cells were transiently transfected with Flag-TLR4, Flag-MD-2 and CD14 constructs (lanes 2-7) or mock transfected (lane 1). 24 h later cells were left untreated (lanes 1 and 2) or stimulated with LPS (lanes 3-7). Flag-tagged proteins were immunoprecipitated with an anti-Flag Ab in cell lysates and analyzed by SDS-PAGE and immunoblotted with an anti-phosphotyrosine Ab (top panel), or an anti-Flag Ab (middle and lower panels). (B) HEK293 cells were transiently transfected with Flag-TLR4 and Flag-MD-2 (lanes 1-5). 24 hrs later, cells were pretreated for 2 hrs with herbimycin A at 0.5 μg/ml (lane 3) or 2.5 μg/ml (lane 4), or for 1 hr with 2 μM cytochalasin D (lane 5) prior to stimulation with LPS for 5 mins.

FIGS. 16A-16C show that Lyn interacts with MD-2. (A) HEK293 cells were transiently transfected with MD-2, Flag-TLR4 and CD14 construct. 24 h later, cells were left untreated (lanes 1 and 2) or stimulated with LPS (lanes 3-5). Lyn proteins were immunoprecipitated with an anti-Lyn antibody in cell lysates and analyzed by SDS-PAGE and immunoblotted with an anti-Flag Ab (top panel), or an anti-Lyn Ab (lower panel). (B) HEK293 cells were transiently transfected with Flag-Lyn, Myc-TLR4 and HA-MD-2 and CD14 constructs. 24 h later, cells were left untreated (lanes 1 and 2) or stimulated with LPS (lanes 3-4). HA-tagged proteins were immunoprecipitated with an anti-HA Ab in cell lysates, and analyzed by SDS-PAGE and immunoblotted with an anti-Flag Ab. (C) HEK293 cells were transiently transfected with Flag-Lyn and HA-MD-2 construct. 24 h later, cells were left untreated (lanes 1 and 2) or stimulated with LPS (lanes 3-5). HA-tagged proteins were immunoprecipitated with an anti-HA Ab in cell lysates and analyzed by SDS-PAGE and immunoblotted with an anti-Flag Ab.

FIGS. 17A-17B show that MD-2 tyrosine phosphorylation is inhibited by Lyn peptide inhibitor. (A) HEK293 cells were transiently transfected with TLR4 and Myc-MD-2 (lanes 1-6). 24 hrs later, cells were pretreated for 2 hrs with Lyn peptide inhibitor at 10, 20 or 30 µM, prior to stimulation with LPS for 10 mins (lanes 3-6). Myc-tagged proteins were immunoprecipitated with an anti-Myc Ab in cell lysates, and analyzed by SDS-PAGE and immunoblotted with an anti-phosphotyrosine Ab (top panel), or an anti-Myc Ab (lower panel). (B) HEK293 cells stably transfected with a NF-κB or IL-8 reporter gene and TLR4 were transiently transfected with wild-type MD-2 24 hrs later, cells were pretreated for 2 hrs with Lyn peptide inhibitor (µM) at indicated doses. Cells were left untreated or stimulated with LPS for 6 hours and luciferase activity measured in cell lysates and expressed as fold induction relative to untreated cells.

DESCRIPTION OF THE INVENTION

Figure 1A:
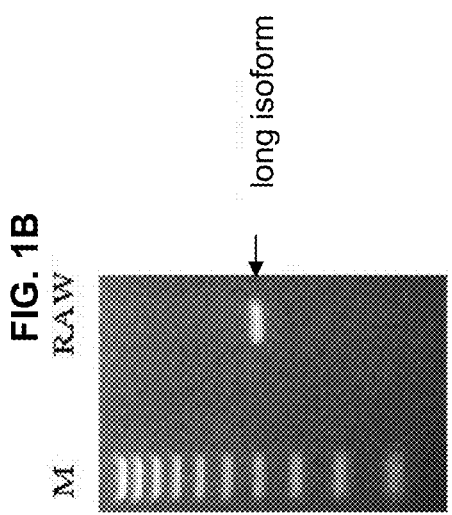
FIGS. 1A-1G depict detection of an alternatively spliced isoform of MD-2 in human, but not mouse cells in accordance with an embodiment of the present invention. RNA from (A) HMECs, (B) RAW 246.7 cells, or (C) murine liver tissue, and dendritic cells were isolated and reverse transcribed into cDNA. Following cDNA synthesis, RT-PCR using human or mouse MD-2-specific primers, was performed. (D) A schematic representation depicting the mature human MD-2 protein shown above the alternatively spliced MD-2s isoform. MD-2s is generated by skipping exon 2. An amino acid substitution, D38G, also occurs at the junction between exons 2 and 3. (E) Sequence alignment of wild-type MD-2 and MD-2s. (F) Expression profiles of MD-2 and MD-2s in different human tissues. MD-2 and MD-2s were amplified by RT-PCR from the indicated human tissues, as described herein. (G) Detection of MD-2s in BMDMs derived from transgenic mice that contain human MD-2 (lanes 1, 3, and 4).

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* $3^{rd}$ ed., J. Wiley & Sons (New York, N.Y. 2001); March, *Advanced Organic Chemistry Reactions, Mechanisms and Structure* $5^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Therapeutically effective amount" as used herein refers to that amount which is capable of achieving beneficial results in a patient in need of treatment. A therapeutically effective amount can be determined on an individual basis and will be based, at least in part, on consideration of the physiological characteristics of the mammal, the type of delivery system or therapeutic technique used and the time of administration relative to the progression of the disease.

"Treatment" and "treating," as used herein refer to both therapeutic treatment and prophylactic or preventative measures, wherein the object is to prevent, slow down and/or lessen the disease, even if the treatment is ultimately unsuccessful.

"Conditions," as used herein, may include, but are in no way limited to any condition or disease in which modulation of TLR4 signaling would be beneficial, including partial or complete TLR4 inhibition. Conditions may include, but are in no way limited to, sepsis, septic shock, inflammation, lung inflammation, LPS-induced acute lung injury (ALI), gram negative bacterial infections, gram negative bacterial lung infections, asthma, allergic asthma, house dust mite (HDM)-induced allergic airway inflammation, perennial rhinitis, and atopic dermatitis (AD), viral infections, immune responses such as atherosclerosis and other diseases or conditions resulting from or characterized by TLR4 activation and/or an over-exaggerated MD2/TLR4-induced immune response.

"Isolated" nucleic acid as used herein refers to nucleic acids (e.g., DNA or RNA) that are isolated relative to other nucleic acids in the source material. For example, "isolated DNA" that encodes MD-2s (including cDNA) refers to DNA isolated relative to DNA which encodes polypeptides other than MD-2s.

"Purified" protein or polypeptide as used herein refers to proteins or polypeptides that are purified relative to other proteins or polypeptides in the source material. For example, "purified MD-2s" refers to MD-2s purified relative to proteins and polypeptides other than MD-2s.

"Binds specifically" as used herein refers to the act of an antibody binding to its antigen and is intended to exclude low-level, non-specific binding that may occur between random proteins. "Binds specifically" as used herein is not intended and does not imply that the antibody will not bind to any protein other than the proteins or polypeptides as disclosed herein since antibodies can cross-react with any protein that includes the relevant epitope.

An inappropriately excessive immune response causes considerable morbidity and mortality in a number of diseases. For example, sepsis is among the most common causes of death in the United States, with over 750,000 cases presenting annually, of which more than one-quarter are fatal (Angus et al. (2001) CRIT CARE MED 29, 1303-1310). Excessive inflammation is the hallmark of a number of related infectious pathologies as well, including acute respiratory distress syndrome and multiple organ failure (Miller et al. (2005) NAT REV MICRO 3, 36-46). LPS derived from bacterial sources can contribute to these diseases, and does so by interacting with a complex consisting of TLR4, CD14, LBP, and MD-2. To circumvent an excessive host immune response to LPS, it is imperative that TLR4 signal transduction be tightly regulated, but the precise molecular mechanisms by which this is accomplished are only partly understood.

The most direct way to attenuate TLR4 signaling is by targeting specific proteins at the extracellular level, akin to the method employed by the soluble TLR4 decoy receptors. Another mechanism dispatches the LPS receptor complex for endosomal trafficking, which results in lysosomal degradation of TLR4 and termination of LPS signal transduction (Husebye et al. (2006) EMBO J 25, 683-692; Latz et al. (2002) J BIOL CHEM 277, 47834-47843). In addition, the relative levels of LBP, CD14, MD-2 and TLR4 all have a direct effect on the potency of the host response to LPS (Abreu et al. (2001) J IMMUNOL 167, 1609-1616; Kitchens et al. (2003) J ENDOTOXIN RES 9, 113-118). However, despite the elucidation of the MD-2 and TLR4 crystalline structures (Kim et al. (2007) CELL 130, 906-917; Ohto et al. (2007) SCIENCE 316, 1632-1634), it remains unclear as to the precise mechanism by which LPS interacts with the MD-2/TLR4 complex. While numerous studies have shown that LPS directly associates with both TLR4 and MD-2 (Poltorak et al. (2000) PROC NATL ACAD SCI USA 97, 2163-2167; da Silva Correia et al. (2001) J BIOL CHEM 276, 21129-21135), it has also been proposed that a monomeric LPS:MD-2 complex, rather than LPS alone, is the true ligand for TLR4 (Gioannini et al. (2004) PROC NATL ACAD SCI USA 101, 4186-4191; Visintin et al. (2005) J IMMUNOL 175, 6465-6472; Prohinar et al. (2007) J BIOL CHEM 282, 1010-1017).

It is clear that myeloid differentiation-2 (MD-2) is an essential component of the signaling receptor complex that recognizes and initiates an innate immune response to bacterial LPS (Shimazu et al. (1999) J EXP MED 189, 1777-1782). At the receptor level, LPS binding protein (Schumann et al. (1990) SCIENCE 249, 1429-1431), CD14 (Wright et al. (1990) SCIENCE 249, 1431-1433) and TLR4 (Inohara et al. (2002) TRENDS BIOCHEM SCI 27, 219-221; Kato et al. (2000) BLOOD 96, 362-364; Visintin et al. (2001) PROC NATL ACAD SCI USA 98, 12156-12161) are also required in this signaling event, as is evidenced by the fact that mice deficient in either of these proteins or MD-2 (Shimazu et al. (1999) J EXP MED 189, 1777-1782) display a similar hyporesponsiveness to LPS challenge. For signaling to occur, LPS is first extracted from the bacterial membrane by LBP, which is then transferred to CD14 in its monomeric form. CD14 subsequently delivers LPS to MD-2, which is a secreted glycoprotein that belongs to the MD-2-related lipid recognition (ML) family (Inohara et al. (2002) TRENDS BIOCHEM SCI 27, 219-221), the signature sequence of which is a secretion signal. MD-2 may be present in a soluble form or bound to the ectodomain of TLR4 (Kato et al. (2000) BLOOD 96, 362-364; Visintin et al. (2001) PROC NATL ACAD SCI USA 98, 12156-12161)). Upon LPS binding, a receptor multimer composed of two copies of the TLR4-MD-2-LPS complex is formed (Park et al. (2009) NATURE 458, 1191-1195), which triggers a downstream signaling cascade, culminating in the activation of transcription factors such as nuclear factor-κB (NF-κB) and the interferon regulatory factors (IRFs), which in turn induce various immune and inflammatory genes.

Upon ligand binding, the TLR signaling pathway initiates a cascade of serine, threonine and tyrosine phosphorylation events. Interestingly, several members of the TLR family are also tyrosine phosphorylated, including TLR2 (Arbibe et al. (2000) NAT IMMUNOL 1, 533-540), TLR3 (Sarkar et al. (2004) NAT STRUCT MOL BIOL 11, 1060-1067; Sarkar et al. (2007) J BIOL CHEM 282, 3423-3427; Sarkar et al. (2003) J BIOL CHEM 278, 4393-4396), and TLR4 (Medvedev et al. (2007) J BIOL CHEM 282, 16042-16053; Chen et al. (2003) AM J PHYSIOL LUNG CELL MOL PHYSIOL 284, 607-613). To date the identity of the kinases involved have yet to be elucidated, however, in the case of TLR4, the Src kinase Lyn has been implicated in this posttranslational modification (Medvedev et al. (2007) J BIOL CHEM 282, 16042-16053). In addition to TLRs, the TLR adapter proteins, MyD88 (Ojaniemi et al. (2003) EUR J IMMUNOL 33, 597-605), MyD88-adapter like (Gray et al. (2006) J BIOL CHEM 281, 10489-10495), TRIF (Bin et al. (2003) J BIOL CHEM 278, 24526-24532) and TRAM (McGettrick et al. (2006) PROC NATL ACAD SCI USA 103, 9196-9201) have also been shown to be phosphorylated.

Described herein, the inventors further elucidate the complexities involved in averting an excessive and dysregulated immune response to LPS by the identification of a naturally occurring alternatively spliced isoform of human MD-2, which the inventors have termed MD-2s. The inventors report that human MD-2s is generated by the removal of exon 2 from MD-2, which leads to an in-frame deletion of 30 amino acids spanning positions 39-69, and one amino acid substitution (D38G). Under similar conditions and using primers homologous to the murine MD-2 gene, a corresponding murine splice variant was not detected. The mRNA expression profile of MD-2s revealed that it is ubiquitously expressed, suggesting that this isoform may perform a widespread role in regulating LPS signal transduction. The inventors also detected MD-2s protein, indicating that MD-2s mRNA is not subject to nonsense-mediated decay, and found that similar to wild type MD-2, multiple forms of MD-2s were detected upon overexpression. Glycosidase treatment established that the slower migrating forms of MD-2s represented glycosylated MD-2s protein. The glycosylation sites of MD-2 are located to the extremity of the cavity region and are believed to play a role in the secretion and stability of the protein (Ohto et al. (2007) SCIENCE 316, 1632-1634). Closer analysis of MD-2s confirmed that it is also stably secreted.

The functional studies provide significant insights into a novel regulatory mechanism employed to control TLR4 signaling upon exposure to LPS. Ectopic expression of the MD-2s isoform failed to trigger NF-κB activation following LPS treatment, suggesting that MD-2s interferes with normal LPS-induced signaling. Interaction studies demonstrated that MD-2s maintains the ability to bind TLR4. This may have been predicted, given that MD-2s retains most of the residues reported to be essential in mediating a MD-2/TLR4 interaction, with the exception of 166 and R68 (Kim et al. (2007) CELL 130, 906-917; Re et al. (2003) J IMMUNOL 171, 5272-5276). In addition, MD-2s interacts directly with both MD-2 and LPS. Thus, MD-2s binds to LPS, TLR4, and MD-2.

Two theoretical models of LPS-induced MD-2/TLR4 dimerization have been proposed. Model 1 proposes that MD-2 first binds LPS, which induces a structural change in MD-2 that in turn facilitates an interaction between a second TLR4 molecule. In model 2, the remaining chains of LPS that are not accommodated in the ligand binding pocket are predicted to interact with a second TLR4 (Kim et al. (2007) CELL 130, 906-917). An independent study also predicts that the binding of LPS promotes TLR4 homodimerization of the TLR4 ectodomains (Walsh et al. (2008) J IMMUNOL 181, 1245-1254). It is thought unlikely that MD-2 homodimerization is required for receptor dimerization (Kim et al. (2007) CELL 130, 906-917), which concurs with previous reports indicating that monomeric MD-2 preferentially binds TLR4 and confers LPS responsiveness more efficiently than MD-2 multimers (Re et al. (2002) J BIOL CHEM 277, 23427-23432).

The results showing that MD-2s suppresses LPS-induced TLR4 activation are most consistent with at least two possibilities. First, MD-2s could be forming a complex with MD-2; this would reduce the amount of active monomeric MD-2 available to bind both LPS and TLR4, which could in turn suppress TLR4 activation. Secondly, MD-2s could interact directly with LPS, and then compete with the MD-2:LPS complex for binding to TLR4. These possibilities are not mutually exclusive, and either or both could be operative, the net effect is still the same: MD-2s suppresses LPS-induced TLR4 activation by acting as a competitive inhibitor of the active MD2:LPS:TLR4 signaling assembly.

In addition, there is another possible mechanism by which MD-2s could interfere with TLR4 activation. MD-2s retains the His155 and Phe126 residues, both of which are required for TLR4 dimerization. However, the missing exon may alter the tertiary structure such that these essential residues are no longer able to promote an effective interaction between MD-2s and a second TLR4 molecule, and the subsequently reduced TLR4 dimerization might reduce TLR4-dependent signaling. Also this could minimize the formation of a TLR4:MD-2 heterodimer due to the number of TLR4:MD2 complexes being proportionally reduced as the number of TLR4:MD-2s complexes increase.

Based on these results and while not wishing to be bound to any particular theory, the inventors believe that MD-2s functionally behaves like a decoy co-receptor by binding LPS and TLR4 to form a non-functional complex that does not activate NF-κB (FIG. 7, left panel). In addition, MD-2s heterodimerizes with MD-2, thus decreasing the availability of the more active monomeric MD-2, which in turn would be predicted to further dampen LPS-induced NF-κB activation (FIG. 7, right panel). The inventors are currently investigating whether or not MD-2s interferes with formation of TLR4:TLR4 dimers (FIG. 7, middle panel). Nevertheless, collectively, the results define an important role for MD-2s in regulating the LPS/TLR4 signal transduction pathway.

According to embodiments disclosed herein, the inventors determined the role of MD-2 in TLR4 signaling and demonstrated that MD-2 undergoes tyrosine phosphorylation upon LPS stimulation and that this phosphorylation event is required for LPS-induced NF-κB activation. Phosphorylation is a highly conserved mechanism that can be employed to regulate protein function. Indeed several studies have illustrated that the TLR signaling pathway is dependent on a series of phosphorylation events. As disclosed herein, the inventors discovered that similar to TLR2, TLR3, and TLR4, MD-2 also undergoes tyrosine phosphorylation in response to LPS. Furthermore, the disclosed results suggest that phosphorylation of MD-2 on specific tyrosines are required for NF-κB activation and can be a regulatory step employed to curtail an over exuberant host immune response. Furthermore, the inventors confirmed that this MD-2 tyrosine phosphorylation was specific to LPS stimulation, as it did not occur following stimulation with IL-1β or TNFα.

As described herein, this phosphorylation event is inhibited by the tyrosine kinase inhibitor herbimycin A. Furthermore, an endocytosis inhibitor, cytochalasin D, blocks the tyrosine phosphorylation of MD-2 in cells stimulated with LPS. The inventors have identified two residues, located at positions 22 and 131, as possible phospho-accepting tyrosines. Mutant proteins in which these tyrosines were altered to phenylalanine have a significantly reduced ability to activate LPS-induced NF-κB and IL-8. In addition, the inventors determined that Lyn interacts with MD2 and that a Lyn-binding peptide inhibitor specifically abolishes MD-2 tyrosine phosphorylation, thus according to certain embodiments Lyn is the kinase required for MD-2 tyrosine phophorylation. The inventors have shown that MD-2 as a phosphoprotein and have demonstrated the importance of this posttranslational event as a mechanism required for MD-2-TLR4-LPS signaling.

Based on these results and while not wishing to be bound to any particular theory, the inventors believe that Lyn is responsible for LPS stimulated MD-2 tyrosine phosphorylation. LPS-induced tyrosine phosphorylation of MD-2 is specific, it is blocked by the tyrosine kinase inhibitor, Herbimycin A, and by an inhibitor of endocytosis, Cytochalsin-D, suggesting that MD-2 phosphorylation occurs during trafficking of MD2 and not on cell surface. Furthermore, the inventors have identified two possible phospho-accepting tyrosine residues at positions 22 and 131. Mutant proteins in which these tyrosines were changed to phenylalanine have significantly diminished ability to activate NF-κB in response to LPS. In addition, MD2 co-precipitates with Lyn kinase and pretreatment with a Lyn-binding peptide inhibitor abolished MD2 tyrosine phosphorylation, suggesting that Lyn is a likely candidate to be the kinase required for MD-2 tyrosine phophorylation. The currently disclosed studies demonstrate that tyrosine phosphorylation of MD-2 is important for signaling following exposure to LPS and underscores the importance of this event in mediating an efficient and prompt immune response.

Also described herein, the inventors demonstrated that the alternatively spliced form of human MD-2 has clear beneficial effects on TLR4-mediated lung injury using the murine models of LPS-induced ALI and HDM-induced allergic airway inflammation. To investigate the in vivo effects of MD-2s on TLR4-mediated lung inflammation, the inventors used two mouse models dependent on MD2/TLR4 signaling: LPS-induced acute lung injury (ALI) and house dust mite (HDM)-induced allergic airway inflammation. In both models, the inventors found that overexpression of MD-2s led to marked reduction in markers of tissue injury and inflammation.

HDM is a mouse model of allergic asthma. House dust mites (HDM; *Dermatophagoides* sp.) are one of the commonest sources of airborne allergens worldwide and the inventors can consider that HDM sensitization affects more than 15-20% of the population from industrialized countries. Atopic patients exposed to HDM allergens develop potent inflammatory diseases in such allergic asthma, perennial rhinitis, and atopic dermatitis (AD). Experimental evidences suggest that HDM allergen-specific Th2 cells play the central role in the allergic inflammatory response inducing the production of allergen-specific IgE, the eosinophil recruitment in tissues, the permissiveness of endothelium for the recruitment of inflammatory cells to inflamed lungs, the production of mucus, and the modulation of the airway smooth muscle contraction.

MD-2s markedly reduced the numbers of inflammatory cells, total proteins, MPO activity, and IL-6, KC, and MIP-2 levels in BALF and lung homogenate after LPS exposure to the lungs. Additionally, the results of the BALF transfer experiment showed that sMD-2s also ameliorated LPS-induced ALI in mice. TLR4 alone is not sufficient for conferring LPS responsiveness. MD-2 is absolutely required for TLR4 signaling and considered the co-receptor for triggering of TLR4 signaling. Indeed, addition of exogenous MD-2 protein could reverse LPS hypo-responsiveness in some experiments. In addition, MD-2 knockout mice do not respond to LPS and survive against endotoxic shock. Hence, MD-2 is the logical target for pharmacological intervention against triggering of TLR4 signaling. As LPS recognition is the first step of the signaling pathway, inhibiting this process could be an efficient way to suppress inflammatory responses before the signal has been transmitted into the downstream pathways. Some effective approaches targeting this step have already been described, but most of them are mainly focused on TLR4 and LPS, whereas few antagonists directed toward MD-2 have been reported.

Extensive work has suggested that a number of endogenous molecules such as nuclear protein high-mobility group box 1 or oxidized low-density lipoprotein may be potent activators of TLR4 and capable of inducing proinflammatory cytokine production by the monocyte-macrophage system and the activation and maturation of dendritic cells. Thus, it is possible that MD-2s might also be able to downregulate this endogenous signaling. Further investigations into the scope of MD-2s inhibition are required.

MD-2s is generated by alternatively splicing out exon 2 of the MD-2 gene, which leads to an in-frame deletion of 30 aa spanning at positions 39-69. Earlier studies describing the essential residues in LPS- or TLR4-binding regions of the MD-2 protein, which are intact in our MD-2s. However, recent publications reported the importance of several amino acids in LPS-induced TLR-4/MD-2-mediated cell activation, which are missing in MD-2s. Kawasaki et al. (*Identification of mouse MD-2 residues important for forming the cell surface TLR4-MD-2 complex recognized by anti-TLR4-MD-2 antibodies, and for conferring LPS and taxol responsiveness on mouse TLR4 by alanine-scanning mutagenesis.* J. IMMUNOL. 170: 413-420, 2003) reported that the mouse MD-2 mutant G59A can form the cell-surface TLR4/MD-2 complex, but its ability to confer LPS responsiveness was reduced. Expression of the polymorphic variant G56R MD-2 reduces transfer of endotoxin from CD14 to MD-2, thereby reducing TLR4-dependent cell activation. These data suggest that amino acids encoded in exon 2 of MD-2 gene play key roles in the triggering and activating LPS signaling.

Particular innocuous environmental proteins act as allergens in susceptible hosts, but clear mechanistic explanations of allergenicity are still lacking Concentrated in HDM fecal pellets, Der p 2 has the highest rates of skin test positivity compared with other mite allergens in HDM-allergic patients. Der p 2 belongs to the MD-2-related lipid-recognition domain family of proteins, binds LPS, and also interacts directly with the TLR4 complex, facilitating LPS signaling. Der p 2 drives Th2 inflammation in the airway in a TLR4-dependent fashion by mimicking MD-2 in the absence of MD-2. Thus, Der p 2 has autoadjuvant activity.

This is of special importance because airway epithelial cells express TLR4 but little or no MD-2. Several studies have demonstrated a role for TLR4 signaling in type 2-mediated inflammation. In response to the major allergen HDM, specifically Der p 2, the mucosal epithelium induces proinflammatory mediators such as IL-8, TSLP, and IL-6 that causes the selective recruitment, retention, and accumulation of cells in the lung. In this study, the inventors showed in vitro that MD-2s clearly suppresses HDM-induced IL-8 release in human primary SAEC and also human epithelial cell line. In our allergic lung inflammation model, MD-2s effectively inhibited the increase of Th2 cytokine, IL-5, and eosinophil count in BALF, and histological studies found that MD-2s substantially inhibited HDM-induced goblet cell hyperplasia in the airway. These results suggest that MD-2s may be useful for the treatment of HDM-related allergic lung inflammation via its inhibition of TLR4 signaling.

MD-2 also plays an important role in certain viral infections. During influenza infection, reactive oxygen species production leads to oxidized lipids that can potently signal though TLR4, requiring MD-2 in the process. Additionally, during respiratory syncytial virus infection, the F protein also signals through MD-2/TLR4. In both of these cases, excess inflammation can lead to damaging pneumonia, which, when inhibited by TLR4 agonists, may help resolve the inflammation. Finally, the HIV Tat protein has also been shown to bind the TLR4-MD-2 complex, leading to its activation and dysregulation. Thus, these viral infections may also present attractive targets for MD-2s-based immune regulation. Sepsis remains a leading cause of death worldwide. Despite years of extensive research, effective drugs that inhibit the proinflammatory effects of LPS and improve outcome when added to conventional sepsis treatments are lacking. An alternatively spliced isoform, such as MD-2s, can behave like a decoy coreceptor to form a non-functional complex that negatively regulates downstream signaling. Described herein, the inventors showed that MD-2s attenuates TLR4-mediated inflammatory responses in vivo, indicating that MD-2s may be useful in the treatment of inflammation associated with TLR4 and LPS. Our data also indicates that in addition to several other alternatively spliced inhibitory check points, an MD-2s-mediated negative-feedback loop also ensures that innate immunity is self-limiting, which can be relevant to sepsis, asthma, cancer, and several other diseases with an inflammatory component.

Embodiments of the present invention are based, at least in part, on the inventors' identification of the alternatively spliced isoform of human MD-2. Similar to wild-type MD-2, it is demonstrated herein that MD-2s is secreted and glycosylated. In addition, despite its ability to interact with TLR4 and LPS, MD-2s fails to mediate NF-κB activation following LPS exposure. Importantly, MD-2s is identified as a negative regulator of LPS-induced NF-κB activation. The inventors' results therefore, define a novel mechanism that can curtail excessive activation of the innate immune response following initiation of the LPS/TLR4 signal transduction pathway.

Further embodiments of the present invention are based on the inventors' discovery that MD-2 is phosphorylated on certain tyrosine residues. In particular, two of the substitutions, MD-2-Y22F and MD-2-Y131F, resulted in a 50% decrease in NF-κB activity upon LPS stimulation, indicating that these residues were critical for maximal NF-κB activation and could possibly be phospho-accepting residues. Importantly, by analyzing the published crystal structure of MD-2, the inventors determined that the hydroxyl groups of both MD2 tyrosine residues, located at positions 22 and 131, are surface exposed thereby permitting phosporylation of the aforementioned residues to occur.

Still further embodiments of the present invention relate to the kinase for MD-2 phosphorylation, Lyn kinase. Lyn kinase is recruited to TLR4 as well as to CD14 upon LPS stimulation and has also been implicated as the kinase involved in the tyrosine phosphorylation of TLR4. According to embodiments described herein, MD-2 has been determined to also be present in a complex with TLR4 and Lyn and that MD-2 can immunoprecipitate Lyn in the absence of CD14 and TLR4. Furthermore the inventors determined that LPS-induced MD-2 tyrosine phosphorylation is strongly abolished following pre-treatment with a Lyn-binding peptide inhibitor. Since MD-2 and Lyn appear to directly interact with one another, and MD-2 tyrosine phosphorylation is diminished following Lyn kinase inactivation, according to certain embodiments, that similar to TLR4, Lyn kinase is involved in the tyrosine phosphorylation of MD-2

TABLE 1

Sequences relating to human MD-2s.

| SEQ ID NO. | Sequence | Description |
|---|---|---|
| 1 | MLPFLFFSTLFSSIFTEAQKQYWVCNSSDASISYTYC GRDLKQLYFNLYITVNTMNLPKRKEVICRGSDDDY SFCRALKGETVNTTISFSFKGIKFSKGKYKCVVEAIS GSPEEMLFCLEFVILHQPNSN | Expressed protein |
| 2 | EAQKQYWVCNSSDASISYTYCGRDLKQLYFNLYIT VNTMNLPKRKEVICRGSDDDYSFCRALKGETVNTT ISFSFKGIKFSKGKYKCVVEAISGSPEEMLFCLEFVIL HQPNSN | Secreted protein |
| 3 | KMQYPISINVNPCIELKGSKGLLHIFYIP | Polypeptide encoded by Exon 2 |

TABLE 1 -continued

Sequences relating to human MD-2s.

| SEQ ID NO. | Sequence | Description |
|---|---|---|
| 4 | atgttacca tttctgtttt tttccaccct gttttcttcc atatttactg aagctcagaa gcagtattgg gtctgcaact catccgatgc aagtatttca tacacctact gtgggagaga tttaaagcaa ttatatttca atctctatat aactgtcaac accatgaatc ttccaaagcg caaagaagtt atttgccgag gatctgatga cgattactct ttttgcagag ctctgaaggg agagactgtg aatacaacaa tatcattctc cttcaaggga ataaaatttt ctaagggaaa atacaaatgt gttgttgaag ctatttctgg gagcccagaa gaaatgctct tttgcttgga gtttgtcatc ctacaccaac ctaattcaaa ttag | Nucleotide sequence for expressed protein |
| 5 | gaagctcagaa gcagtattgg gtctgcaact catccgatgc aagtatttca tacacctact gtgggagaga tttaaagcaa ttatatttca atctctatat aactgtcaac accatgaatc ttccaaagcg caaagaagtt atttgccgag gatctgatga cgattactct ttttgcagag ctctgaaggg agagactgtg aatacaacaa tatcattctc cttcaaggga ataaaatttt ctaagggaaa atacaaatgt gttgttgaag ctatttctgg gagcccagaa gaaatgctct tttgcttgga gtttgtcatc ctacaccaac ctaattcaaa ttag | Nucleotide sequence for secreted protein |
| 6 | ataaaatgcaatacccaatttcaattaatgttaacccctgtctagaattgaaaagatc caaaggattattgcacattttctacattccaa | Nucleotide sequence of Exon 2 |

One embodiment of the present invention provides for a purified MD-2s protein. In various embodiments, the MD-2s is a soluble form of MD-2s.

In one embodiment, a purified polypeptide, the amino acid sequence of which comprises SEQ ID NO:1 is provided. In a particular embodiment, the purified polypeptide consists of the amino acid sequence as set forth in SEQ ID NO:1. In a further embodiment, the purified polypeptide is glycosylated.

In another embodiment, a purified polypeptide, the amino acid sequence of which comprises SEQ ID NO:2 is provided. In a particular embodiment, the purified polypeptide consists of the amino acid sequence as set forth in SEQ ID NO:2. In a further embodiment, the purified polypeptide is glycosylated.

In another embodiment, a purified polypeptide comprising 10, 20 or 30 consecutive residues of SEQ ID NO:1 or SEQ ID NO:2 is provided. One of ordinary skill in the art will readily be able to screen for the purified polypeptide's ability to modulate (e.g., inhibit, induce) TLR signaling without undue burden using methods known in the art and as described herein.

In another embodiment, a purified immunogenic polypeptide comprising an immunogenic domain comprising ten consecutive residues of SEQ ID NO:1 or SEQ ID NO:2. These purified immunogenic polypeptides can be useful for producing antibodies that bind specifically to MD-2s.

In other embodiments, the present invention provides a purified polypeptide comprising residues N26 to N84 of SEQ ID NO:1 or residues N10 to N68 of SEQ ID NO:2. In additional embodiments, the present invention provides a purified polypeptide comprising N-glycosylated sites at positions N26 and N84 of SEQ ID NO:1 or N-glycosylated sites at positions N10 and N68 of SEQ ID NO:2.

In additional embodiments, the present invention provides a purified polypeptide comprising residues involved in the dimerization interface of the TLR4/MD-2/LPS complex. In one embodiment, the purified polypeptide comprises residues V52 to F96 of SEQ ID NO:1, or residues V36 to F80 of SEQ ID NO:2. In another embodiment, purified polypeptide comprising one or more residues selected from the group consisting of V52, M55, L57, R60, S88, K92, G93, 194, K95, and F96 of SEQ ID NO:1; or one or more residues selected from the group consisting of V36, M39, L41, R44, S72, K76, G77, I78, K79, and F80 of SEQ ID NO:2: (Park et al., *The structural basis of lipopolysaccharide recognition by the TLR4-MD-2 complex,* doi:10.1038/nature07830).

In further embodiments, the present invention provides a purified polypeptide comprising residues C37 to C118, or residues C65 and/or C75. In additional embodiments, the present invention provides a purified polypeptide comprising C37 and/or C118, which are residues involved in the second disulphide bond; or C65 and/or C75, which are residues involved in the third disulphide bond of SEQ ID NO:1.

In another embodiment, a purified polypeptide, the amino acid sequence of which comprises a sequence at least 80%, 85%, 90%, 95%, 96%, 97%, 98%, or 99% identical to SEQ ID NO:1 or SEQ ID NO:2 is provided. In a further embodiment, the purified polypeptide is glycosylated.

In another embodiment, a purified polypeptide comprising the amino acid sequence of SEQ ID NO:1 or SEQ ID NO:2, but with 0 to 29 conservative amino acid substitution is provided. In particular embodiments, the purified polypeptides have 0 to 20, 1-20, 0-10, or 1-10 conservative amino acid substitutions. In a further embodiment, the purified polypeptide is glycosylated.

In another embodiment, a purified polypeptide comprising the amino acid sequence of SEQ ID NO:1 or SEQ ID NO:2, but with 0 to 29 amino acid insertions, deletions and/or substitutions is provided. In a particular embodiment, the purified polypeptide has 0 to 20, 1-20, 0-10, or 1-10 amino acid insertions, deletions and/or substitutions. In a further embodiment, the purified polypeptide is glycosylated.

In another embodiment, a purified polypeptide consisting of the amino acid sequence of SEQ ID NO:3 is provided. In another embodiment, a purified polypeptide, the amino acid sequence of which comprises a sequence at least 80%, 85%, 90%, 95%, 96%, 97%, 98%, or 99% identical to SEQ ID NO:3 is provided. These polypeptides may be useful for modulating LPS-induced signaling and/or TLR signaling.

In further embodiments, a purified polypeptide, the amino acid sequence of which comprises SEQ ID NO:17 is provided. In a particular embodiment, the purified polypeptide consists of the amino acid sequence as set forth in SEQ ID NO:17. In a further embodiment, the purified polypeptide is glycosylated. In another embodiment, a purified polypeptide, the amino acid sequence of which comprises a sequence at least 80%, 85%, 90%, 95%, 96%, 97%, 98%, or 99% identical to SEQ ID NO:17 is provided. These polypeptides may be useful for modulating LPS-induced signaling and/or TLR signaling.

In another embodiments, a purified polypeptide, the amino acid sequence of which comprises SEQ ID NO:25 is provided. In a particular embodiment, the purified polypeptide consists of the amino acid sequence as set forth in SEQ ID NO:25. In a further embodiment, the purified polypeptide is glycosylated. In another embodiment, a purified polypeptide, the amino acid sequence of which comprises a sequence at least 80%, 85%, 90%, 95%, 96%, 97%, 98%, or 99% identical to SEQ ID NO:25 is provided. These polypeptides may be useful for modulating LPS-induced signaling and/or TLR signaling.

In further embodiments, a purified polypeptide, the amino acid sequence of which comprises SEQ ID NO:26 is provided. In a particular embodiment, the purified polypeptide consists of the amino acid sequence as set forth in SEQ ID NO:26. In a further embodiment, the purified polypeptide is glycosylated. In another embodiment, a purified polypeptide, the amino acid sequence of which comprises a sequence at least 80%, 85%, 90%, 95%, 96%, 97%, 98%, or 99% identical to SEQ ID NO:25 is provided. These polypeptides may be useful for modulating LPS-induced signaling and/or TLR signaling.

In various embodiments, the present invention provides pharmaceutical compositions including a pharmaceutically acceptable excipient along with a therapeutically effective amount of MD-2s or a polypeptide as described above. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal or parenteral. "Transdermal" administration may be accomplished using a topical cream or ointment or by means of a transdermal patch. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the parenteral route, the compositions may be in the form of solutions or suspensions for infusion or for injection. Via the topical route, the pharmaceutical compositions based on compounds according to the invention may be formulated for treating the skin and mucous membranes and are in the form of ointments, creams, milks, salves, powders, impregnated pads, solutions, gels, sprays, lotions or suspensions. They can also be in the form of microspheres or nanospheres or lipid vesicles or polymer vesicles or polymer patches and hydrogels allowing controlled release. These topical-route compositions can be either in anhydrous form or in aqueous form depending on the clinical indication. Via the ocular route, they may be in the form of eye drops.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment of a condition in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins PA, USA) (2000).

Typical dosages of an effective amount of MD-2s or a polypeptide as described above can be as indicated to the skilled artisan by the in vitro responses or responses in animal models. Such dosages typically can also be reduced by up to about one order of magnitude in concentration or amount without losing the relevant biological activity. Thus, the actual dosage can depend upon the judgment of the physician, the condition of the patient, and the effectiveness of the therapeutic method based, for example, on the in vitro responsiveness of the relevant primary cultured cells or histocultured tissue sample or the responses observed in the appropriate animal models.

Another embodiment of the present invention provides for a nucleic acid or an isolated nucleic acid encoding the MD-2s protein or a polypeptide as described above.

In one embodiment, a nucleic acid, the nucleotide sequence of which comprises SEQ ID NO:4 is provided. In another embodiment, the nucleic acid is isolated and/or consists of SEQ ID NO:4.

In another embodiment, a nucleic acid, the nucleotide sequence of which comprises SEQ ID NO:5 is provided. In another embodiment, the nucleic acid is isolated and/or consists of SEQ ID NO:5.

In another embodiment, an isolated DNA, the nucleotide sequence of which consists of SEQ ID NO:4 or SEQ ID NO:5 is provided.

In another embodiment, a nucleic acid, the nucleotide sequence of which comprises a degenerate variant of SEQ ID NO:4 or SEQ ID NO:5 is provided. In another embodiment, the nucleic acid is isolated and/or consists of SEQ ID NO:4 or SEQ ID NO:5.

In another embodiment, an isolated nucleic acid comprising a sequence that hybridizes under highly stringent conditions to a hybridization probe, the nucleotide sequence of which consists of SEQ ID NO:4, SEQ ID NO:5 or a complement of SEQ ID NO:4 or SEQ ID NO:5 is provided. In a particular embodiment, the hybridization probe comprises SEQ ID NO:7, SEQ ID NO:8, or SEQ ID NO:9.

In another embodiment, an isolated nucleic acid comprising a sequence at least 90%, 95%, 96%, 97%, 98%, or 99% identical to SEQ ID NO:4 or SEQ ID NO:5, wherein the nucleic acid encodes a polypeptide that binds to TLR4 or LPS is provided. In another embodiment, the isolated nucleic acid consists of a sequence at least 90%, 95%, 96%, 97%, 98%, or 99% identical to SEQ ID NO:4 or SEQ ID NO:5.

In another embodiment, an isolated nucleic acid, the nucleotide sequence of which encodes a polypeptide at least 80%, 85%, 90%, 95%, 96%, 97%, 98%, or 99% identical to SEQ ID NO:1 or SEQ ID NO:2, wherein the polypeptide binds to TLR4 or LPS is provided.

In another embodiment, an isolated nucleic acid comprising a sequence that encodes a polypeptide comprising the sequence of SEQ ID NO:1 or SEQ ID NO:2 with up to 10, 15, 20 or 25 conservative amino acid substitutions, wherein the polypeptide binds TLR4 or LPS, is provided. In a particular embodiment, the isolated nucleic acid consists of the sequence that encodes a polypeptide comprising the sequence of SEQ ID NO:1 or SEQ ID NO:2 with up to 10, 15, 20 or 25 conservative amino acid substitutions.

In another embodiment, an isolated nucleic acid comprising a sequence that encodes a polypeptide comprising the sequence of SEQ ID NO:1 or SEQ ID NO:2 with up to 10, 15, 20 or 25 amino acid insertions, deletions and/or substitutions, wherein the polypeptide binds to TLR4 or LPS, is provided. In another embodiment, the isolated nucleic acid consists of the sequence that encodes a polypeptide comprising the sequence of SEQ ID NO:1 or SEQ ID NO:2 with up to 10, 15, 20 or 25 amino acid insertions, deletions and/or substitutions.

Another embodiment provides for a nucleic acid comprising exon 2 of human MD-2 gene. In one embodiment, a nucleic acid, the nucleotide sequence of which comprises SEQ ID NO:6 is provided. In another embodiment, the nucleic acid is isolated and consists of SEQ ID NO:6.

In another embodiment, an isolated nucleic acid comprising a sequence that encodes a polypeptide comprising the sequence of SEQ ID NO:3 is provided.

Another embodiment of the present invention provides for a PCR primer and/or a nucleic acid probe. The primer and/or probe can be used to identify the presence or absence of MD2s. In one embodiment, the PCR primer and/or nucleic acid probe is a nucleic acid comprising SEQ ID NO:7, SEQ ID NO:8, or SEQ ID NO:9. In another embodiment, the PCR primer and/or nucleic acid probe comprises a nucleic acid at least 80%, 85%, 90%, 95%, 96%, 97%, 98%, or 99% identical SEQ ID NO:7, SEQ ID NO:8, or SEQ ID NO:9. In another embodiment, the PCR primer and/or nucleic acid probe hybridizes under highly stringent conditions to a region comprising exon 1 and exon 3 or a fragment thereof of MD-2s. In one particular embodiment, the PCR primer and/or nucleic acid probe hybridizes under highly stringent conditions to about 20 nucleotides of exon 1 and about 20 nucleotides of exon 3. In other particular embodiments, the PCR primer and/or nucleic acid probe hybridizes under highly stringent conditions to about 10 to 20 nucleotides of exon 1 and about 10 to 20 nucleotides of exon 3. In other particular embodiments, the PCR primer and/or nucleic acid probe hybridizes under highly stringent conditions to about 15 to 20 nucleotides of exon 1 and about 15 to 20 nucleotides of exon 3. In another particular embodiment, the PCR primer and/or nucleic acid probe hybridizes under highly stringent conditions to about 15, 14, 13, 12, 11 or 10 nucleotides of exon 1 and about 15, 14, 13, 12, 11 or 10 nucleotides of exon 3.

In another embodiment, an expression vector comprising a nucleic acid as described above operably linked to an expression control sequence is provided. In various embodiments, the expression vector and expression control sequence may be any expression vector or expression control sequence known in the art or as described herein. Examples of expression vectors include but are not limited to pCDNA3.1, pCMV-HA and pEF-BOS. Examples of expression control sequences include but are not limited to human cytomegalovirus immediate early (CMV) promoter and EF1-α promoter region.

In another embodiment, a cultured cell comprising the expression vector comprising a nucleic acid as described above is provided.

In another embodiment, a cultured cell comprising a nucleic acid as described above, operably linked to an expression control sequence is provided. In various embodiments, the expression control sequence may be any expression control sequence known in the art or as described herein.

In another embodiment, a cultured cell transfected with an expression vector comprising a nucleic acid as described above or a progeny of said cell, wherein the cell expresses a polypeptide as described above is provided.

Another embodiment of the present invention provides for a method of producing MD-2s or a polypeptide as described above is provided.

In one embodiment, the method comprises culturing a cultured cell described above under conditions permitting expression of the polypeptide. In a further embodiment, the method comprises purifying the polypeptide from the cell or the medium of the cell.

In another embodiment, the method comprises culturing a cultured cell described above under conditions permitting expression under the control of the expression control sequence, and purifying the polypeptide from the cell or the medium of the cell.

Another embodiment of the present invention provides for methods of using the isolated MD-2s protein, or compositions comprising the isolated MD-2s protein.

In one embodiment, the method is for inhibiting TLR4 signaling in a subject in need thereof. The method comprises providing a purified MD-2s protein or polypeptide as described above and administering the purified MD-2s protein or polypeptide as described above to the subject. The purified MD-2s protein or polypeptide as described above may be in a composition that further comprises a pharmaceutically acceptable carrier or a pharmaceutically acceptable excipient.

In one embodiment, the method is for inhibiting LPS signaling in a subject in need thereof. The method comprises providing a purified MD-2s protein or polypeptide as described above and administering the purified MD-2s protein or polypeptide as described above to the subject. The purified MD-2s protein or polypeptide as described above may in a composition that further comprises a pharmaceutically acceptable carrier or a pharmaceutically acceptable excipient.

In another embodiment, the method is for treating a condition mediated by TLR4 signaling or reducing the likelihood of developing a condition mediated by TLR signaling in a subject in need thereof. The method comprises providing a purified MD-2s protein or a polypeptide as described above and administering the purified MD-2s protein or polypeptide as described above to the subject. The purified MD-2s protein or polypeptide may be in a composition that further comprises a pharmaceutically acceptable carrier and/or a pharmaceutically acceptable excipient. In various embodiments, the condition is sepsis, septic shock, inflammation, lung inflammation, LPS-induced acute lung injury (ALI), gram negative bacterial infections, gram negative bacterial lung infections, asthma, allergic asthma, house dust mite (HDM)-induced allergic airway inflammation, perennial rhinitis, and atopic dermatitis (AD), viral infections (e.g., influenza, HIV), immune responses such as atherosclerosis and other diseases or conditions resulting from or characterized by TLR4 activation and/or an over-exaggerated MD2/TLR4-induced immune response.

In another embodiment, the method is for inhibiting lipopolysaccharide ("LPS") induced lung inflammation in a subject in need thereof. The method comprises providing purified MD-2s protein or a polypeptide as described above; and administering the polypeptide to the subject to inhibit LPS induced lung inflammation.

In another embodiment, the method is for treating asthma, allergic asthma, house dust mite (HDM)-induced allergic airway inflammation, perennial rhinitis, or atopic dermatitis (AD) in a subject in need thereof. The method comprises providing a purified MD-2s protein or a polypeptide as described above; and administering the polypeptide to the subject to treat asthma, allergic asthma, house dust mite (HDM)-induced allergic airway inflammation, perennial rhinitis, or atopic dermatitis (AD).

Another embodiment of the present invention provides a method of detecting the presence or absence of a nucleic acid that encodes MD-2s in a subject. The method comprises providing a PCR primer or nucleic acid probe as described above; and detecting the presence or absence of a second nucleic acid that encodes MD-2s in a biological sample of the subject, wherein the presence of the second nucleic acid indicates the presence of MD-2s and the absence of the second nucleic acid indicates the absence of MD-2s. In one embodiment, the method comprises providing a first nucleic acid, the nucleotide sequence of which comprises SEQ ID NO:7, SEQ ID NO: 8, or SEQ ID NO:9; and detecting the presence or absence of a second nucleic acid that encodes MD-2s in a biological sample of the subject, wherein the presence of the second nucleic acid indicates the presence of MD-2s and the absence of the second nucleic acid indicates the absence of MD-2s. These methods may further comprise reporting the presence or absence of the second nucleic acid. For example, a laboratory performing the test may report the results to a medical practitioner, such as the subject's doctor and/or the subject's doctor may report the results to the subject. In other non-limiting examples, reporting may comprise recording the results on an electronic storage medium, displaying the results on a computer screen, or printing the results on a piece of paper.

Examples of "biological sample" include but are not limited to mammalian body fluids, sera such as blood (including whole blood as well as its plasma and serum), CSF (spinal fluid), urine, sweat, saliva, tears, pulmonary secretions, breast aspirate, prostate fluid, seminal fluid, stool, cervical scraping, cysts, amniotic fluid, intraocular fluid, mucous, moisture in breath, animal tissue, cell lysates, tumor tissue, hair, skin, buccal scrapings, nails, bone marrow, cartilage, prions, bone powder, ear wax, etc. or even from external or archived sources such as tumor samples (i.e., fresh, frozen or paraffin-embedded).

In one embodiment, detecting the presence or absence of the second nucleic acid comprises contacting the PCR primer or nucleic acid probe with a biological sample of the subject and performing real time polymerase chain reaction on the sample. In a particular embodiment, detecting the presence or absence of the second nucleic acid comprises contacting the first nucleic acid with a biological sample of the subject and performing real time polymerase chain reaction on the sample.

In another embodiment, detecting the presence or absence of the second nucleic acid comprises contacting the PCR primer or nucleic acid probe with a biological sample from the subject and determining whether the PCR primer or nucleic acid probe hybridizes under highly stringent conditions with the second nucleic acid in the biological sample, wherein the presence of a first and second nucleic acid binding complex indicates the presence of the second nucleic acid. In a particular embodiment, detecting the presence or absence of the second nucleic acid comprises contacting the first nucleic acid with a biological sample from the subject and determining whether the first nucleic acid hybridizes under highly stringent conditions with the second nucleic acid in the biological sample, wherein the presence of a first and second nucleic acid binding complex indicates the presence of the second nucleic acid.

Individuals who do not have MD-2s may have a higher risk of developing LPS-induced inflammation or an inflammatory disease. For example, an individual without MD-2s may develop severe sepsis when they are infected with gram negative bacteria. Therefore, another embodiment of the present invention provides for a method to determine a subject's risk of developing LPS-induced inflammation or an inflammatory disease. In one embodiment, the method comprises detecting the presence or absence of a nucleic acid that encodes MD-2s or a polypeptide as described above; and correlating the presence of the nucleic acid with a lower risk of developing LPS-induced inflammation or an inflammatory disease or correlating the absence of the second nucleic acid with a higher risk of developing LPS-induced inflammation or an inflammatory disease. These methods may further comprise reporting the presence or absence of the nucleic acid that encodes MD-2s, or reporting the low or high level of risk of developing LPS-induced inflammation an inflammatory disease. For example, a laboratory performing the test may report the results to a medical practitioner, such as the subject's doctor and/or the subject's doctor may report the results to the subject. In other non-limiting examples, reporting may comprise recording the results on an electronic storage medium, displaying the results on a computer screen, or printing the results on a piece of paper. Examples of LPS-induced inflammation or an inflammatory disease include but are not limited to sepsis, septic shock, gram negative bacterial infection, gram negative bacterial lung infection and immune response such as atherosclerosis.

Alternatively, the method comprises detecting the expression level of a nucleic acid that encodes MD-2s or a polypeptide as described above; comparing the expression level of the nucleic acid to a standardized expression level of a nucleic acid that encodes MD-2s determined from individuals who have MD-2s; and correlating an expression level that is equal or higher than the standardized expression level to a lower risk of developing LPS-induced inflammation or an inflammatory disease or correlating an expression level that is lower than the standardized expression level to a higher risk of developing LPS-induced inflammation or an inflammatory disease. These methods may further comprise reporting the low or high level of risk of developing LPS-induced inflammation an inflammatory disease. For example, a laboratory performing the test may report the results to a medical practitioner, such as the subject's doctor and/or the subject's doctor may report the results to the subject. In other non-limiting examples, reporting may comprise recording the results on an electronic storage medium, displaying the results on a computer screen, or printing the results on a piece of paper. Examples of LPS-induced inflammation or an inflammatory disease include but are not limited to sepsis, septic shock, gram negative bacterial infection, gram negative bacterial lung infection and immune response such as atherosclerosis.

The present invention describes kits for preventing or reducing the likelihood of developing and/or treating a condition using MD-2s and kits for determining a subject's risk of developing severe sepsis. Various embodiments of the present invention thus provides for kits for preventing or reducing the likelihood of developing and/or treating a condition in a mammal in need thereof, comprising: a quantity of MD-2s or a polypeptide as described above and instructions for administering the quantity of MD-2s or the polypeptide as described above to the mammal to prevent, reduce the likelihood of developing and/or treat the condition. Another embodiment of the present invention provides for a kit for determining a subject's risk of developing these diseases or disease conditions, comprising: a quantity of a PCR primer or nucleic acid probe as described above; and instructions for using the quantity PCR primer or nucleic acid probe to determine the subject's risk of developing these diseases or disease conditions. References herein to MD-2s include synthetic, recombinant, naturally-occurring and any other forms of the protein. In one embodiment, the condition is sepsis or septic shock. In another embodiment, the condition is inflammation. In another embodiment, the condition is a lung infection.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Biological Reagents and Cell Culture

Immortalized human dermal microvessel endothelial cells (HMEC) (a kind gift from F. J. Candal, Center for Disease Control and Prevention, Atlanta, Ga.) were cultured in MCDB-131 medium, supplemented with 10% heat-inactivated fetal bovine serum, 2 mM glutamine, and 100 µg/ml penicillin and streptomycin. The HEK293 cell line and the mouse RAW 264.7 macrophage cell line were cultured in Dulbecco's modified Eagle's medium, supplemented with 10% heat-inactivated FBS and 2 mM glutamine. The plasmid encoding human wild-type Flag MD-2 was a generous gift from Kensuke Miyake. LPS (TLRGrade) was from (Alexis) and biotin-LPS (Ultrapure) was from Invivogen. Protein tyrosine kinase inhibitor herbimycin A was purchased from Sigma-Aldrich. Lyn peptide inhibitor was purchased from Tocris Cookson. 4G10 anti-phosphotyrosine Ab was purchased from Upstate. Anti-Flag agarose affinity gel and anti-Flag Ab were from Sigma Aldrich. Anti-Myc and Anti-HA Abs were from Santa Cruz Biotechnology and Zymed Labs respectively.

Example 2

RT-PCR

Total cellular RNA was isolated from HMEC, RAW 264.7, murine dendritic cells, and murine liver tissue using RNeasy mini kit (Qiagen, Valencia, Calif.). RNA from human lung, pancreas, thymus, kidney, spleen, liver, heart, and placenta was purchased from Ambion (Austin, Tex.). Following reverse transcription with Omniscript cDNA synthesis kit (Qiagen), PCR analysis was performed using primers specific for the human MD-2 (sense: ATGTTACCATTTCTGTTT (SEQ ID NO:10)), antisense: CTAATTTGAATTAGGTTG (SEQ ID NO:11)) or mouse MD-2 (sense: TCTGCAACTCCTCCGATG (SEQ ID NO:12), antisense: GGCGGTGAATGATGGTGA (SEQ ID NO:13)). The PCR was performed using Taq DNA polymerase (Invitrogen, Carlsbad, Calif.). Glyceraldehyde-3-phosphate dehydrogenase (GAPDH) served as a loading control.

Example 3

Immunoprecipitation and Immunoblotting

HEK 293 cells were seeded into 100 mm dishes ($1.5 \times 10^6$) 24 h prior to transfection. Transfections were performed according to the manufacturer's instructions using lipofectamine. For co-immunoprecipitations, 4 µg of each construct was transfected. For competition experiments where the effect of increasing sMD-2 expression on complex formation between two signaling molecules was examined, 2 µg of each signaling molecule expression plasmid was transfected in the presence of increasing amounts of the sMD-2 expression plasmid. The total amount of DNA in each sample was kept constant by using empty vector cDNA. In all cases, cells were harvested 24 h following transfection in 600 µl of lysis buffer (50 mM HEPES, pH 7.5, 100 mM NaCl, 1 mM EDTA, 10% glycerol, 0.5% NP-40 containing protease inhibitor cocktail, and 1 mM sodium orthovanadate). For immunoprecipitations, the indicated antibodies were incubated with the cell lysates overnight at 4° C. Subsequently, Trueblot™ IgG beads were added and the samples were incubated at 4° C. for 1 hr. The immune complexes were then washed and the associated proteins were eluted from the beads by boiling in 35 µl of sample buffer, and then fractionated by SDS-PAGE. For immunoblotting, primary antibodies were detected using horseradish peroxidase-conjugated secondary antibodies, followed by enhanced chemiluminescence (Amersham Biosciences).

Example 4

NF-κB and IL-8 Promoter Luciferase Activation in HEK 293 Cells

HEK293 cells were transiently transfected with the expression vectors noted in combination with constructs encoding the NF-κB- and IL-8-luciferase reporter gene, and either the β-galactosidase gene or the phRL-TK report gene to normalize for transfection efficiency. In all cases, total DNA concentration was kept constant by supplementation with empty vector control. Following overnight incubation, cells were stimulated for 6 hours with 50 ng/ml LPS and then lysed, and luciferase activity was measured as described previously (Ohta et al. (2004) BIOCHEM BIOPHYS RES COMMUN 323, 1103-1108). Data are shown as mean±SD of three or more independent experiments and are reported as a percentage of LPS-stimulated NF-κB and IL-8 promoter activity, or relative luciferase activity.

Example 5

Identification of a Novel Human MD-2 Splice Variant

Figure 1B:
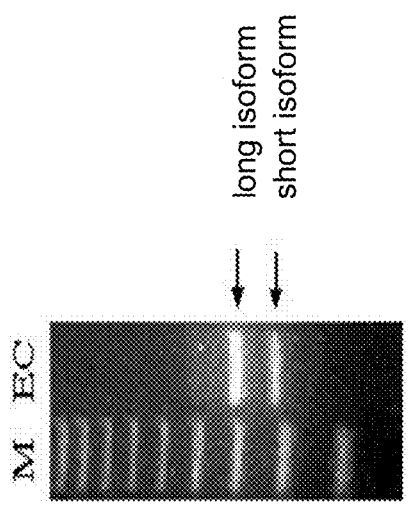
Figure 1C:
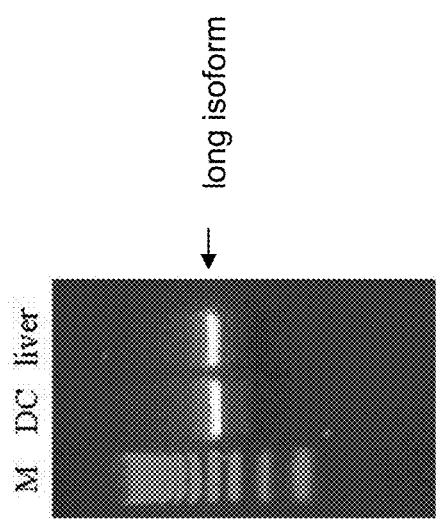

During the inventors' analysis of MD-2 expression in HMECs, two cDNA products approximately 390 and 480 bp in length (FIG. 1A) were detected by RT-PCR. The expression of murine MD-2 was also examined by performing RT-PCR on cDNA derived from the murine cell line, RAW 246.7 (FIG. 1B). In contrast, using primers homologous to the same region in the mouse as in the human, only the larger RT-PCR product was detected. To confirm that the absence of the smaller fragment was not specific to the murine cell line selected, cDNA from murine bone marrow derived dendritic cells and liver tissues obtained from C57BL/6 mice were also amplified. Again only the larger cDNA fragment was observed in the murine tissues tested (FIG. 1C).

Figure 1D:
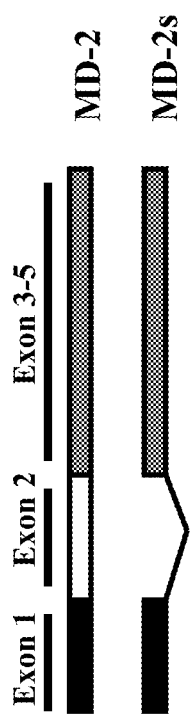
Figure 1E:
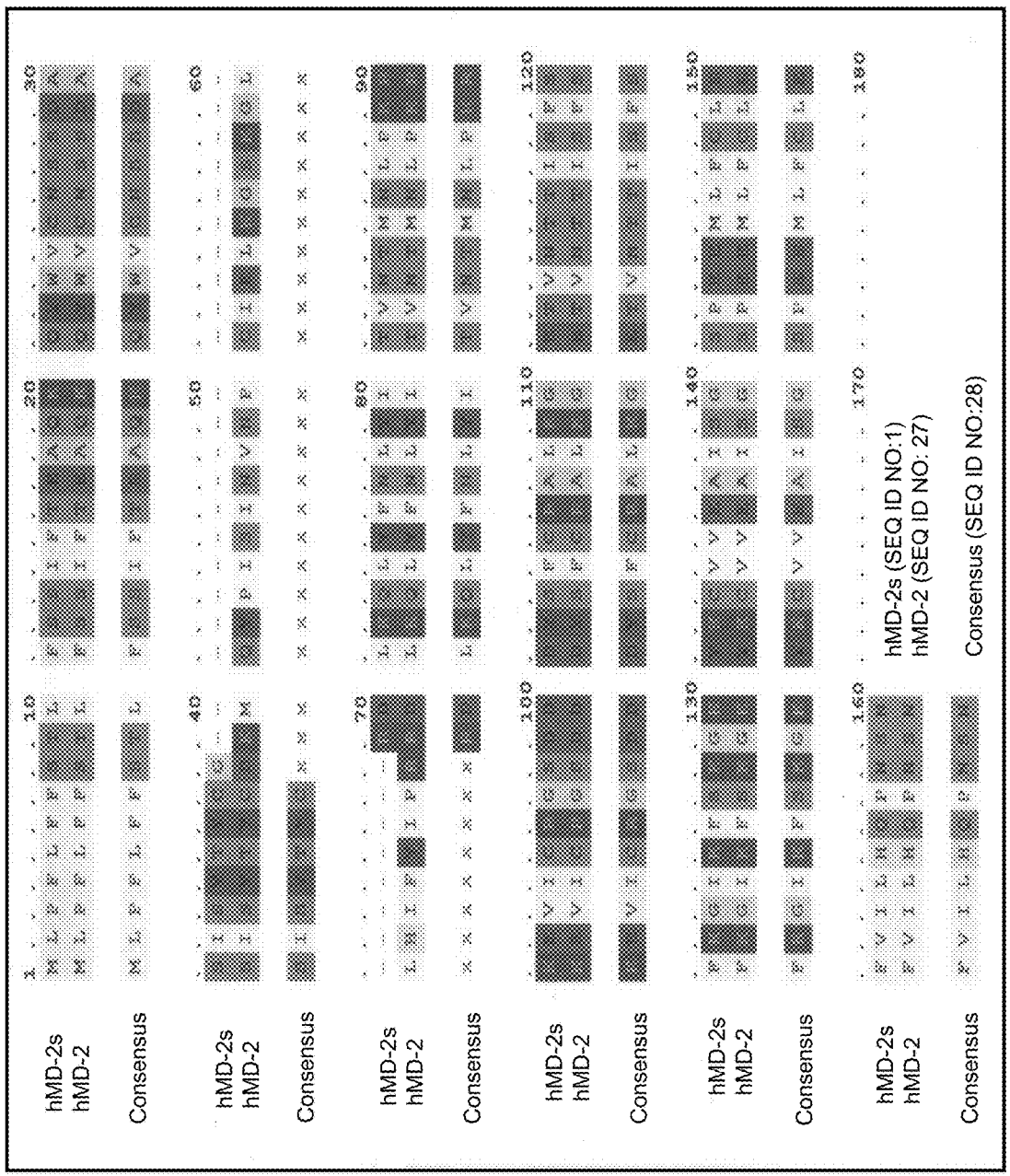
Figure 1F:
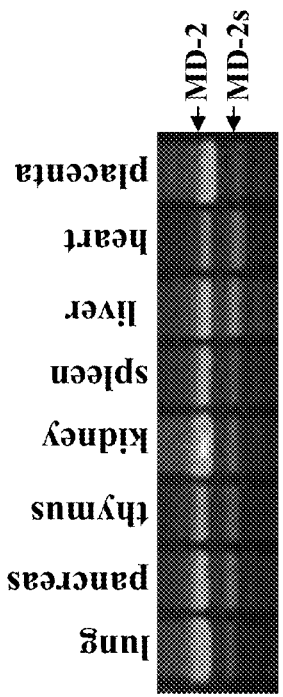

Upon sequencing the larger cDNA fragment detected in HMECs, it was determined that this PCR product corresponded to the published sequence of full-length human MD-2. Sequence analysis of the smaller cDNA fragment (subsequently referred to as MD-2s), revealed that this was a splice variant of human MD-2, which lacked the region encoded by exon 2 of the MD-2 gene (FIGS. 1D and E). This isoform is putatively translated into a 114-residue protein with no frame shift, however, one amino acid substitution, D38G, occurs at the junction between exons 2 and 3.

Figure 1G:
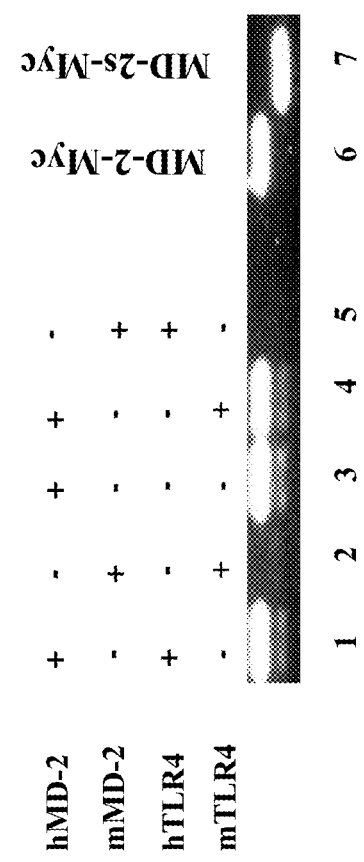

To further characterize the expression profile of MD-2s, RT-PCR analysis on a variety of human tissues was performed. As shown in FIG. 1G, MD-2s was widely expressed in all human tissues analyzed. Furthermore, it was observed that the full length wild-type MD-2 is the predominant form detected, although the ratio between MD-2 and MD-2s varies in different tissues. These findings establish that MD-2s is not a result of tissue-specific alternative splicing, but rather is ubiquitously expressed in all human tissues tested.

Having established that MD-2s is not expressed in the mouse, it was investigated if MD-2s could be detected in transgenic mice overexpressing the human MD-2 gene. RT-PCR analysis conducted on BMDMs from these mice revealed that MD-2s can be detected irrespective of the presence or absence of human or murine TLR4 (FIG. 1G, compare lane 3, to lane 1 or 4).

To determine why the human but not the mouse MD-2 gene alternatively skips exon 2, the gene structures and sequences of the two species were compared (Table 2). Both the human and the murine MD-2 genes are organized into five exons and four introns, and each species encodes a predicted full-length MD-2 protein of 145 amino acids. Alignment of the human and mouse genomic regions revealed that the exons and coding sequences were well conserved. However, analysis of the non-coding regions revealed a number of differences. In particular, it was noted that intron 1 of human MD-2 is composed of 13239 base pairs, while the mouse has 3067. The longer intron 1 may increase the probability for alternative lariat formation during the splicing process of human MD-2. In addition, after comparing the sequences at the 3' end of intron 1, murine MD-2 was found to have more pyrimidines than human MD-2, which may lead to a more stable lariat formation in murine MD-2, thereby preventing alternative splicing of exon 2 in this species.

TABLE 2

| (a) | E-1 coding | Intron 1 | Sequences at 3' of Intron 1 | E2 | E3 | E4 | E5-coding |
|---|---|---|---|---|---|---|---|
| Human | 112 | 13241 | ttgacattatcttta ttgcttttag (SEQ ID NO: 14) | 90 | 129 | 53 | 99 |
| Mouse | 112 | 3064 | ttg-TattTtcttCa ttCcttttag (SEQ ID NO: 15) | 90 | 129 | 53 | 99 |

(b)
5'-ttgacattatctttattgcttttagATAAAATGCAATACCCAATTTCAATTAA
TGTTAACCCCTGTCTAGAATTGAAAAGATCCAAAGGATTATTGCACATTTTCTACA
TTCCAAgtaagttcaaattttgctttata-3' (SEQ ID NO: 16)

(a) Comparison of human and mouse MD-2 gene structure.
(b) The intron-exon boundary of exon 2 in the MD-2 gene is depicted, with the intronic sequences in lower case and the excised sequence in upper case.

Example 6

Similar to Wild-Type MD-2, MD-2s is Glycosylated and Secreted

In order to characterize this newly identified isoform of human MD-2, the smaller RT-PCR fragment was amplified and cloned into an expression vector containing a Myc tag. HEK293 cells were subsequently transiently transfected with MD-2s-Myc. Cellular extracts were later prepared and SDS-PAGE analysis was performed. Similar to wild-type MD-2, multiple forms of MD-2s could be detected upon overexpression (FIG. 2A, lane 1). The altered electrophorectic mobility of wild-type MD-2 is due to N-linked glycosylations at positions Asn26 and Asn114 (Ohnishi et al. (2001) J IMMUNOL 167, 3354-3359). These residues are still present in MD-2s, but since MD-2s lacks 30 amino acids, the tertiary structure is likely to be different from wild-type MD-2, which could result in occlusion of these known glycosylation sites. To determine if the altered electrophorectic mobility of MD-2s was due to glycosylation, immunoprecipitated MD-2s, isolated from HEK293 cells transiently expressing MD-2s-Myc, was treated with the N-glycosidase, PNGaseF. Samples were then analyzed by SDS-PAGE and immunoblotted with an anti-Myc antibody. It was found that the slowest migrating forms of MD-2s were no longer evident in the PNGaseF-treated sample (FIG. 2A, lane 2). These results indicate that similar to wild type MD-2, MD-2s is a glycoprotein.

Next, it was investigated if MD-2s exists as a stably secreted protein. Myc-tagged proteins were immunoprecipitated from culture supernatants obtained from HEK293 cells transiently expressing MD-2s-Myc. Samples were subsequently analyzed by SDS-PAGE and immunoblotted with an anti-Myc antibody. As shown in FIG. 2B, lane 2, MD-2s is present in a soluble form.

Example 7

MD-2s Fails to Induce NF-κB Activation Following LPS Stimulation

Figure 3A:
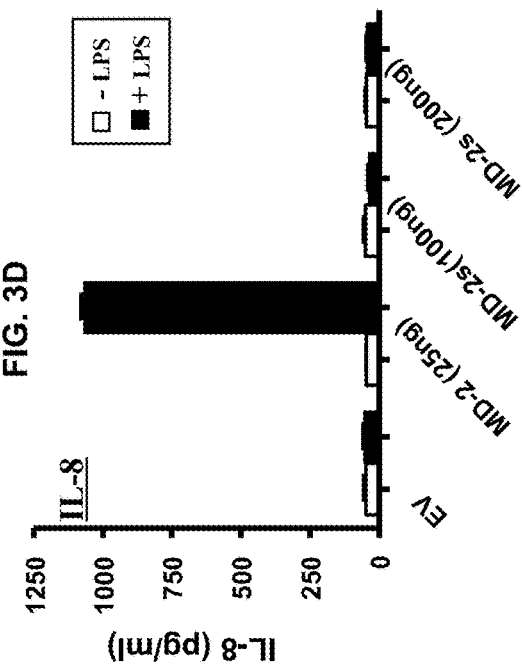
FIGS. 3A-3D show that MD2-s fails to mediate either LPS-dependent NF-κB activation or IL-8 secretion in accordance with an embodiment of the present invention. (A) HEK-293 cells stably transfected with TLR4 and a NF-κB reporter gene were treated with supernatants containing either MD-2 or MD-2s as described in the examples herein. Cells were left untreated or stimulated with LPS for 24 h. Mean relative stimulation of luciferase activity±S.D. for a representative experiment, each performed in triplicate, is shown. (B) HEK-293 cells stably transfected with TLR4 and a NF-κB reporter gene were transiently transfected with plasmids encoding for either MD-2, MD-2s or CD14 as shown. 24 h later, cells were left untreated or stimulated with LPS (250 ng/ml) for 6 h. Mean relative stimulation of luciferase activity±SD for a representative experiment, each performed in triplicate, is shown. (C) and (D) Supernatants were also collected and measured for IL-8 secretion.
Figure 3B:
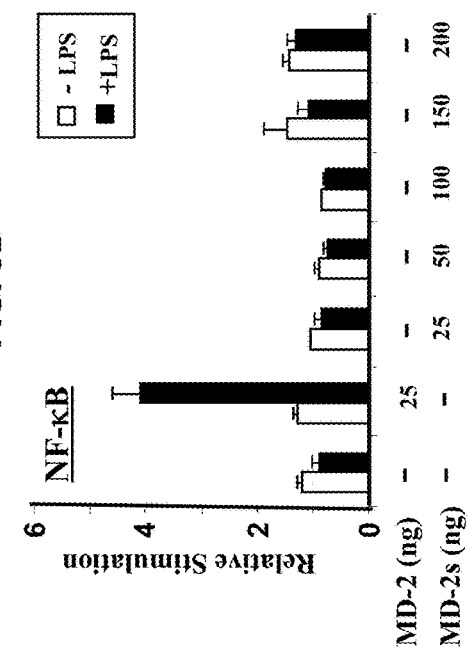
Figure 3C:
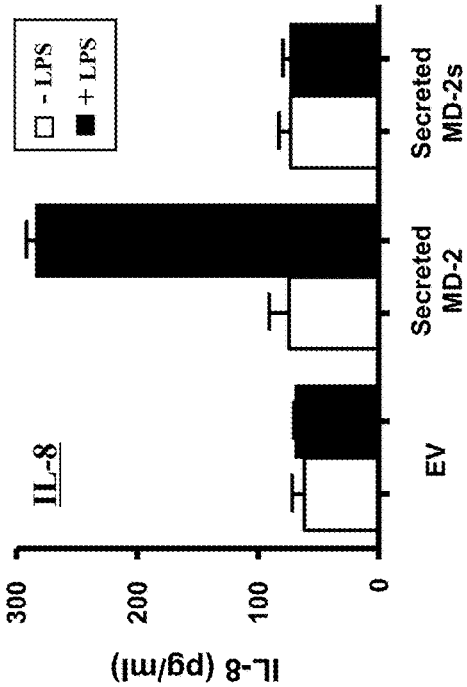
Figure 3D:
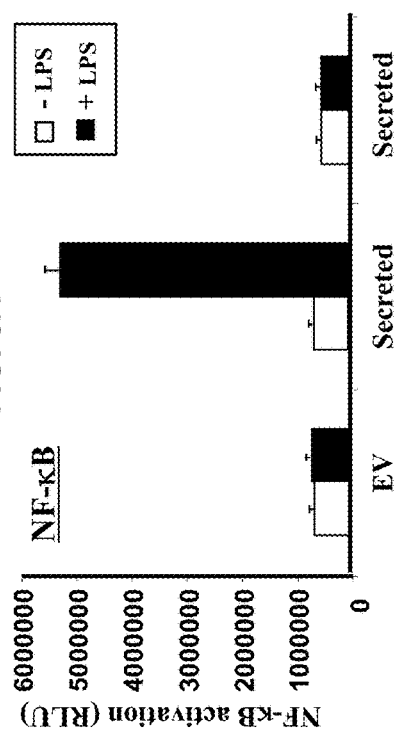

The requirement for MD-2s in LPS mediated NF-κB activation was assessed. It has been shown that the soluble form of wild-type MD-2 confers LPS responsiveness to cells expressing TLR4; therefore, it was investigated if soluble MD-2s was also bioactive. Culture supernatants were obtained from HEK293 cells transiently expressing control vector, MD-2, or MD-2s, and incubated with HEK293 cells stably transfected with TLR4 and an NF-κB-dependent luciferase reporter gene. As previously shown, soluble MD-2 strongly activated NF-κB following LPS stimulation (FIG. 3A). However, the secreted form of MD-2s could not confer LPS responsiveness to these cells as measured by NF-κB activation (FIG. 3A) or IL-8 secretion (FIG. 3C).

MD-2s was tested to see if it needed to be transiently expressed in TLR4 reporter cells in order to mediate NF-κB activation following LPS stimulation. HEK293 cells stably transfected with TLR4 and an NF-κB-dependent luciferase reporter gene were transiently transfected with plasmids encoding CD14 in combination with either MD-2 or MD-2s, and subsequently treated with LPS. In agreement with published results, wild-type MD-2 activated NF-κB in response to LPS treatment. In contrast, MD-2s was unable to induce LPS-mediated NF-κB activation, even at higher concentrations (FIG. 1B) or IL-8 secretion (FIG. 1D). Taken together, these results suggest that the region of human MD-2 encoded by exon 2 plays an important role in mediating LPS-induced signaling.

Example 8

Similar to Wild-Type MD-2, MD-2s Interacts with TLR4

Figure 4A:
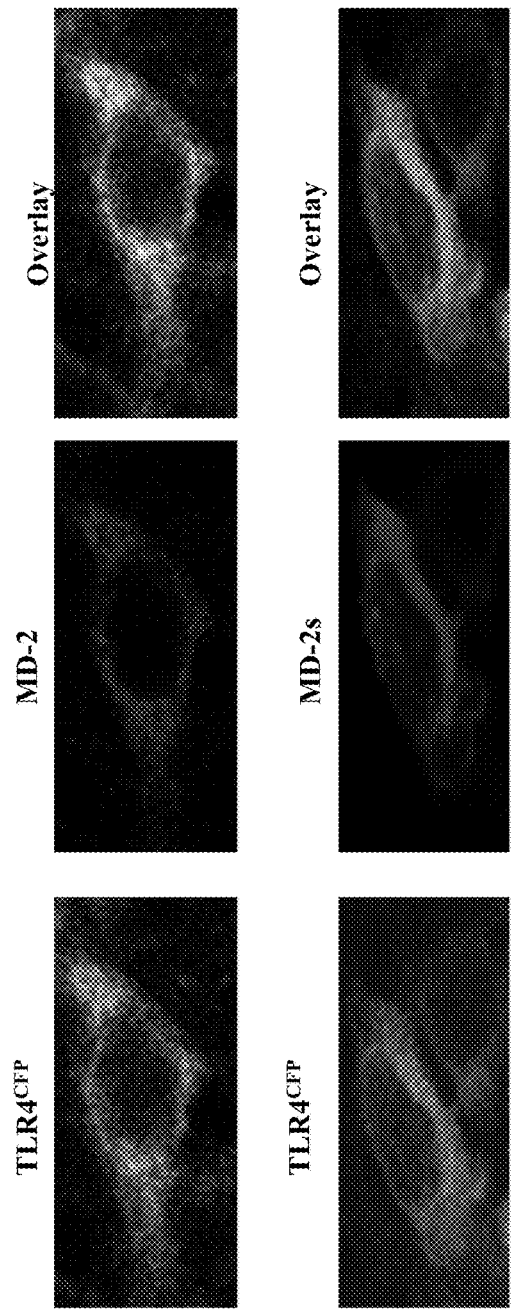
FIGS. 4A-4B shows that MD-2s colocalizes and interacts with TLR4 in accordance with an embodiment of the present invention. (A) Cells stably expressing CFP-tagged TLR4 were transiently transfected with plasmids encoding wild-type MD-2 (upper panels) or MD-2s (lower panels). 24 h later, cells were incubated with an anti-Myc antibody and cross-liked with Alexa 647-conjugated anti-mouse polyclonal secondary antibody. (B) HEK293 cells were transiently transfected with a plasmid encoding for Flag-tagged TLR4 (lane 2) and cotransfected with either a Myc-tagged MD-2 (lane 3) or a Myc-tagged MD-2s (lanes 1 and 4) expressing plasmid. Co-immunoprecipitation experiments were then performed using an anti-Flag antibody (lanes 2-4) or an IgG isotype control antibody (lane 1). Samples were fractionated by SDS-PAGE and immunoblotting with an anti-Myc antibody was performed. Experiment shown is representative of 4 separate experiments.
Figure 4B:
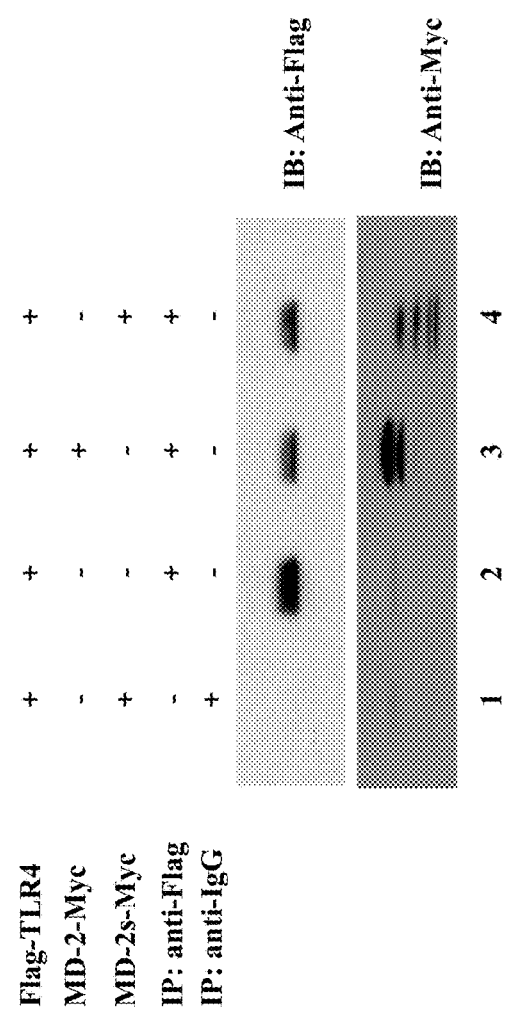

Given that MD-2s failed to induce LPS-dependent NF-κB activation, the inventors questioned whether this might be due to an inherent inability to interact directly with TLR4. To address this possibility, co-localization studies to examine the cellular distribution of MD-2s with respect to TLR4 were performed. HEK293 cells stably expressing TLR4CFP were subsequently transiently transfected with a plasmid encoding either MD-2 (FIG. 4A, upper panel) or MD-2s (FIG. 4A, lower panel) and stained with an anti-Myc antibody. Confocal analysis revealed that both TLR4 and MD-2s exhibited the same cellular distribution (FIG. 4A, lower right hand side panel). Next whether MD-2s is physically associated with TLR4 was assessed. HEK293 cells were transiently transfected with a plasmid encoding FLAG-tagged TLR4 in combination with either a Myc-tagged MD-2 or a Myc-tagged MD-2s expressing plasmid, and co-immunoprecipitation experiments were performed. It was determined that similar to MD-2, a direct interaction between MD-2s and TLR4 was observed (FIG. 4B, lane 4), indicating that although MD-2s fails to induce LPS-dependent NF-κB activation, this cannot be attributed to an inability to associate with TLR4.

Example 9

MD-2s Diminishes LPS-Induced NF-κB Activation

Figure 5A:
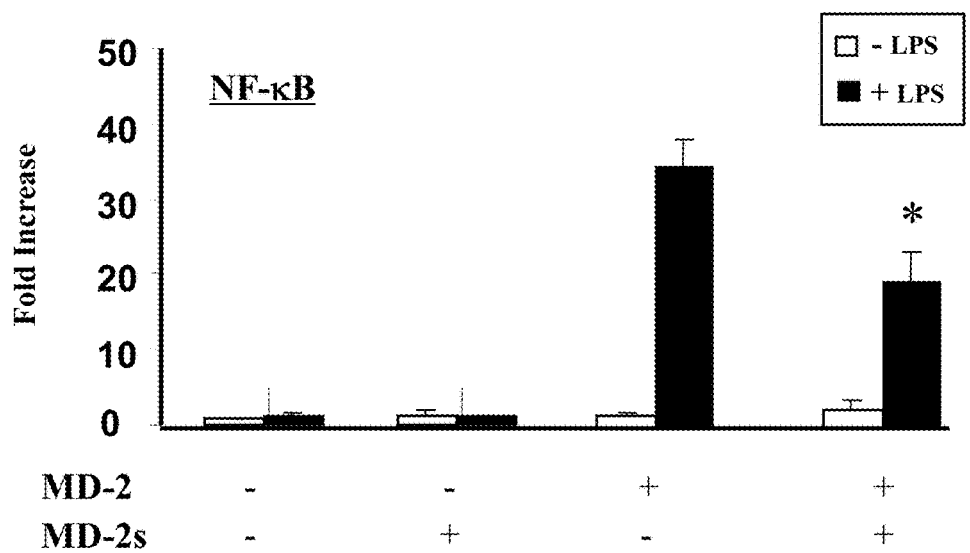
FIGS. 5A-5B show that MD-2s inhibits LPS-induced NF-κB activation in accordance with an embodiment of the present invention. (A) HEK293 cells were transiently transfected with plasmids encoding TLR4 and a NF-κB reporter gene in combination with MD-2 and MD-2s as indicated. 24 h later, cells were left untreated or incubated with LPS (250 ng/ml) for 5 h. Mean relative stimulation of luciferase activity±S.D. for a representative experiment from three separate experiments, each performed in triplicate, is shown. (B) HEK-293 cells stably transfected with TLR4 and a NF-κB reporter gene were treated with supernatants containing either MD-2 and MD-2s as depicted and left untreated or incubated with LPS for 24 h. Mean relative stimulation of luciferase activity±S.D. for a representative experiment from three separate experiments, each performed in triplicate, is shown.
Figure 5B:
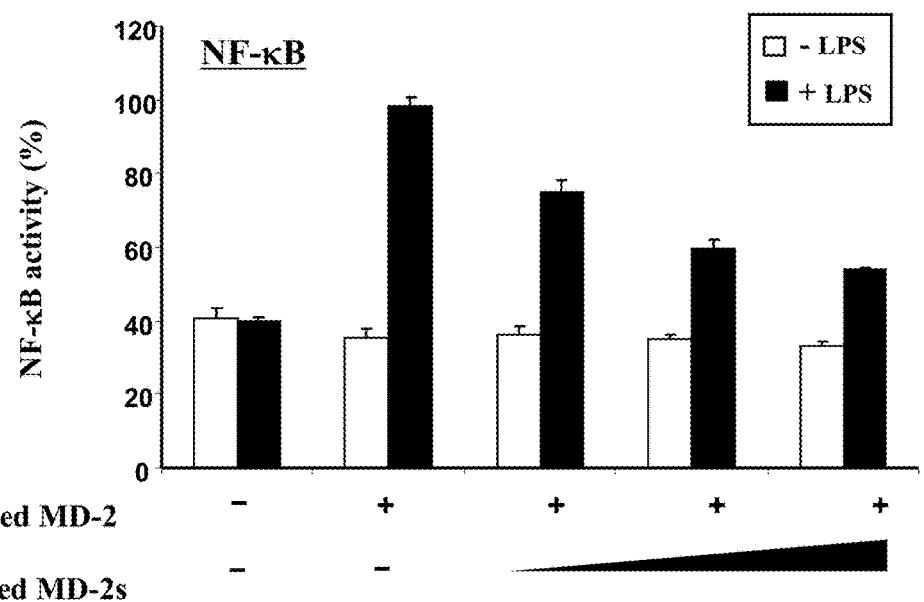

Having determined that MD-2s does not activate NF-κB, we next investigated the effect of MD-2s on MD-2/TLR4-mediated LPS signaling. HEK293 cells were transiently transfected with plasmids encoding CD14, TLR4, and wild-type MD-2 in conjunction with a plasmid encoding the NF-κB-dependent luciferase reporter gene in the presence or absence of a plasmid encoding MD-2s. As shown in FIG. 5A, MD-2s significantly inhibited LPS-induced NF-κB activation. Furthermore, we assessed the inhibitory role of soluble MD-2s following LPS stimulation. HEK293 cells stably transfected with TLR4 and an NF-κB-dependent luciferase reporter gene were incubated with supernatants obtained from HEK293 cells transiently expressing a constant amount of MD-2 with increasing concentrations of MD-2s. It was determined that soluble MD-2s inhibits NF-κB activation (FIG. 5B). This suggests that the region encoded by exon 2 is critical for efficient TLR4 signaling.

Example 10

MD-2s Interacts with MD-2 and LPS

Figure 6A:
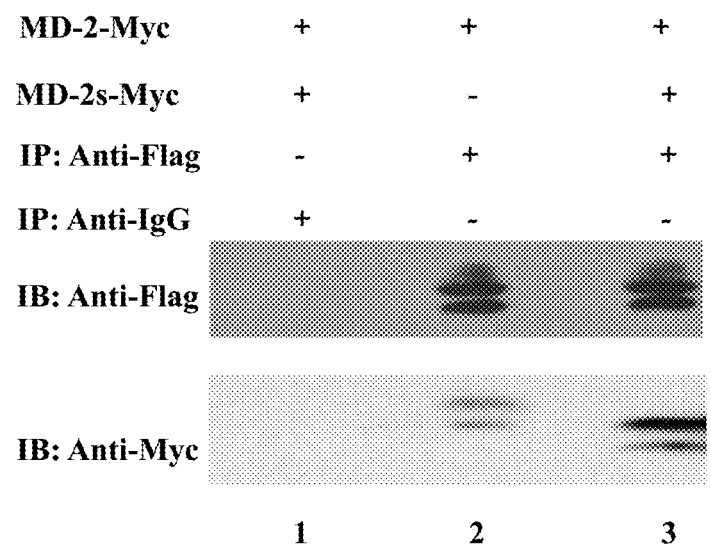
Figure 11:
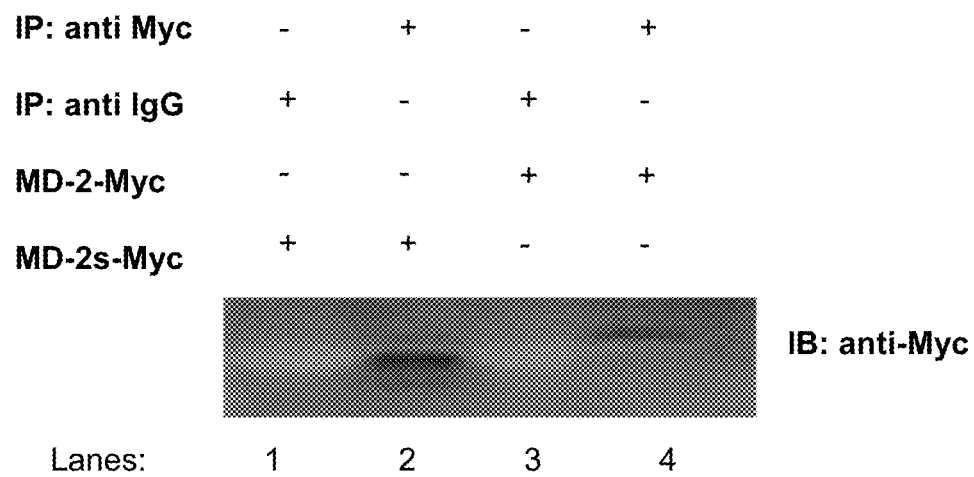
FIG. 11 depicts HEK293 cells that stably express MD-2 or MD-2s in accordance with an embodiment of the present invention. HEK293 cells were transiently transfected with plasmids expressing either MD-2-Myc or MD-2s-Myc and subsequently selected with G418. Culture supernatants from cells stably expressing MD-2s (lanes 1 and 2) or MD-2 (lanes 3 and 4) were collected and immunoprecipitations were performed using a control antibody (lanes 1 and 3) or with an anti-myc antibody (lanes 2 and 4). Samples were subsequently analyzed by SDS/PAGE and immunoblotted (IB) with an anti-Myc antibody.
Figure 12B:
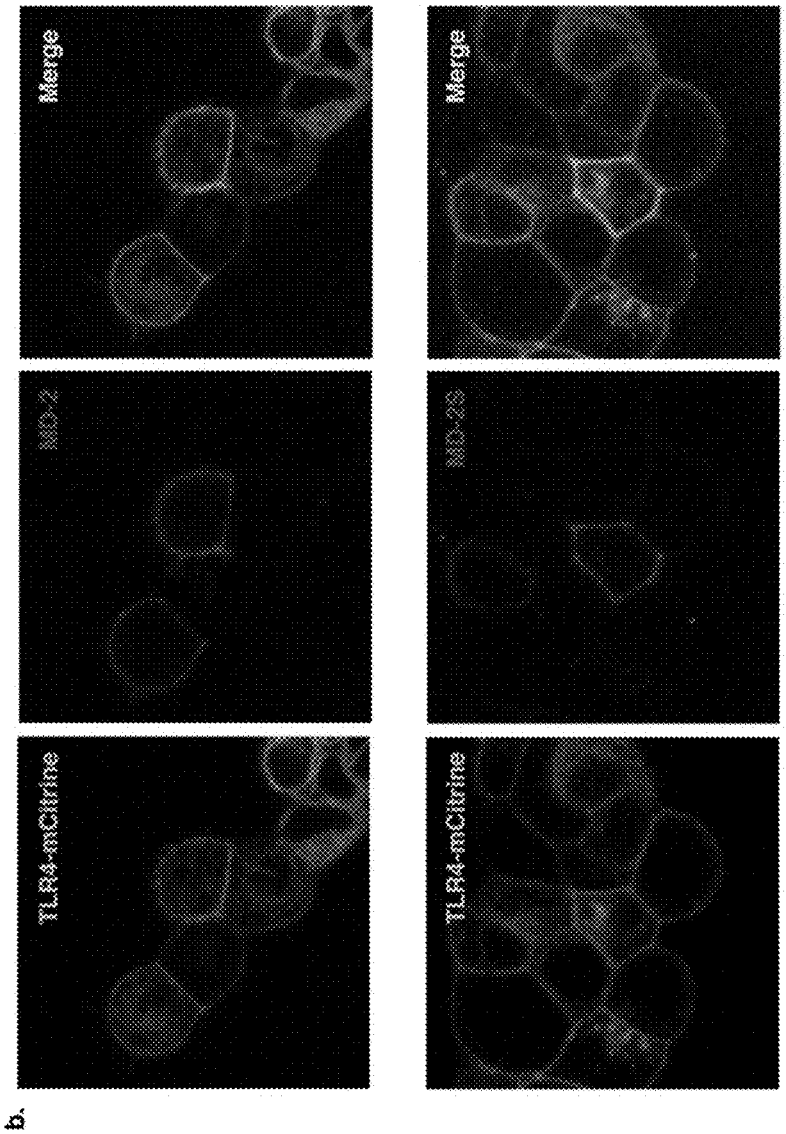

Previous reports indicate that monomeric MD-2 preferentially binds TLR4 and confers LPS responsiveness more efficiently than MD-2 multimers (Re et al. (2002) J BIOL CHEM 277, 23427-23432). Therefore, it was investigated if MD-2s could interact with wild-type MD-2, which could potentially diminish responsiveness to LPS by reducing the amount of available monomeric MD-2. HEK293 cells were transiently transfected with a plasmid encoding FLAG-tagged MD-2, in combination with either a Myc-tagged MD-2 or a Myc-tagged MD-2s expressing plasmid, and co-immunoprecipitation experiments were performed. Similar to previous reports, it was observed that MD-2 can homodimerise (FIG. 6A, lane 2). It was also noted that MD-2s associates with wild-type MD-2 (FIG. 11, lane 3). These results raise the possibility that the mechanism by which MD-2s inhibits LPS-induced TLR4-dependent signaling is by reducing the amount of the active monomeric species of MD-2, and thus increasing the multimeric form of MD-2. Both would be predicted to lead to a reduction in TLR4-dependent signaling during exposure to LPS (Re et al. (2002) J BIOL CHEM 277, 23427-23432; Teghanemt et al. (2008) J BIOL CHEM 283, 21881-21889).

Figure 6B:
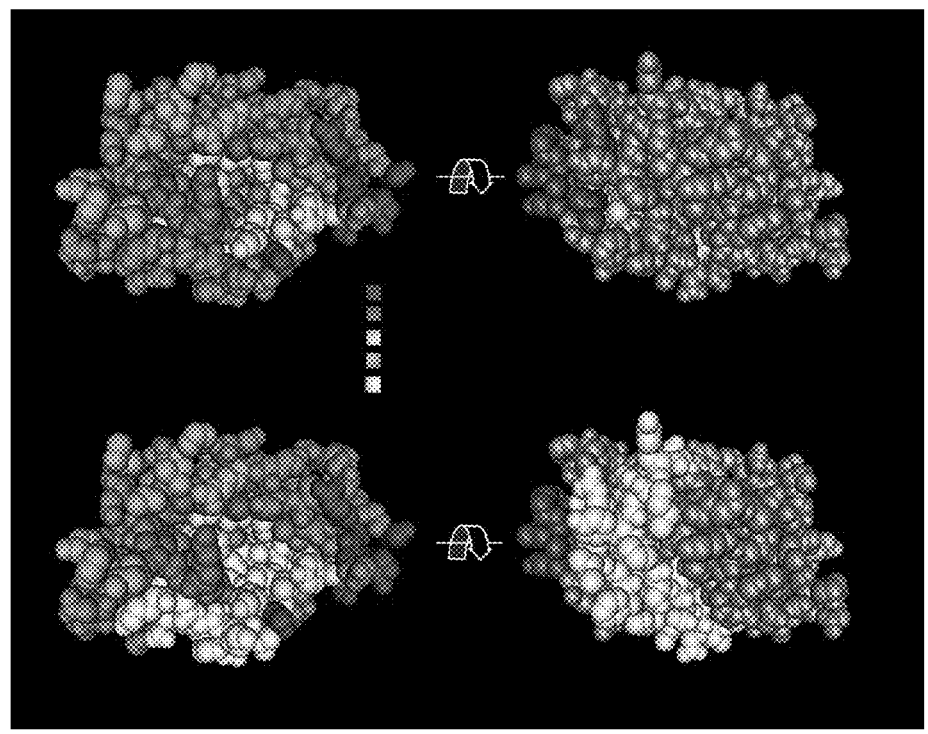
Figure 8A:
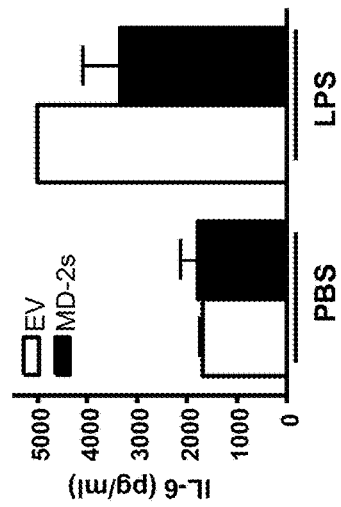
Figure 8B:
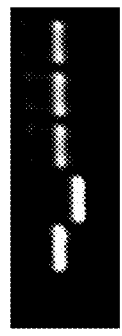
Figure 8C:
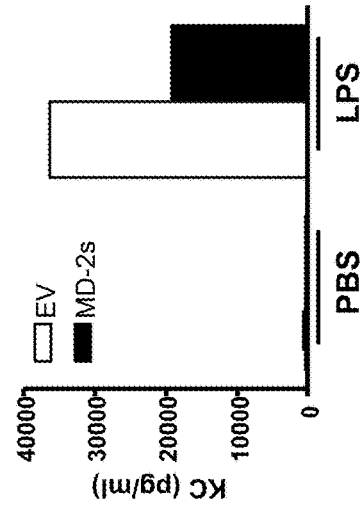
Figure 8D:
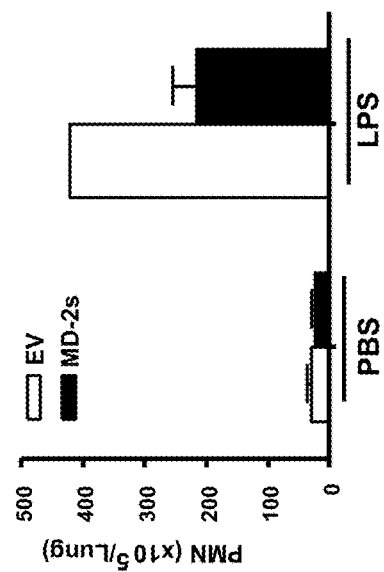

The published structural models of MD-2 were also analyzed to ascertain the structural effect of deleting exon 2. MD-2 consists of a β-cup fold with two anti-parallel β-sheets, the first one composed of six β-strands (numbered 1/2/9/8/5/6) and the other of three (numbered 3/4/7) (Kim et al. (2007) CELL 130, 906-917; Ohto et al. (2007) SCIENCE 316, 1632-1634). The missing exon 2 of MD-2s encodes the first two β-strands of the three-stranded β-sheet (β3 and β4 strands) (FIG. 6B). The hinges connecting β-strands 2 to 3 and 4 to 5 are also partially lost. Furthermore, the disulphide bond between Cys25 and Cys51, which assists in closing the MD-2 cavity and stabilizing the cup-like structure, is disrupted. The 136 and 137 strands that line the entrance to the deep hydrophobic cavity are still encoded by MD-2s mRNA.

Previous mutational studies have demonstrated that the LPS-binding region of MD-2 depends on Lys89, Arg90, Lys91, Phe119, Phe121, Lys122, Lys125, Lys128, and Lys132. Several of these residues have also been shown to be directly involved in the binding of Eritoran and Lipid IVa to MD-2 (Kim et al. (2007) CELL 130, 906-917; Ohto et al. (2007) SCIENCE 316, 1632-1634). Although all of the aforementioned residues are present in MD-2s, structural analysis of this protein implied that the ligand-binding pocket may be severely disrupted, suggesting that MD-2s may be unable to bind LPS efficiently. To address this possibility, HEK293 cells were transiently transfected with plasmids encoding either MD-2 or MD-2s. Culture supernatants were then incubated with biotin-LPS and Myc-tagged proteins were immunoprecipitated. In agreement with previous studies, secreted MD-2 bound readily to LPS (FIG. 6C, lane 4) (Visintin et al. (2003) J BIOL CHEM 278, 48313-48320). Interestingly, under similar conditions, an interaction between secreted MD-2s and LPS was also detected (FIG. 6C, lane 6), suggesting that exogenous MD-2s may actively sequester LPS from MD-2. Hence, these results suggest a second way that MD-2s could suppress LPS-induced activation of TLR4 is by directly binding LPS, thereby reducing the availability of LPS to bind with monomeric MD-2 and thus diminishing TLR4 signal transduction.

Example 11

Figure 9A:
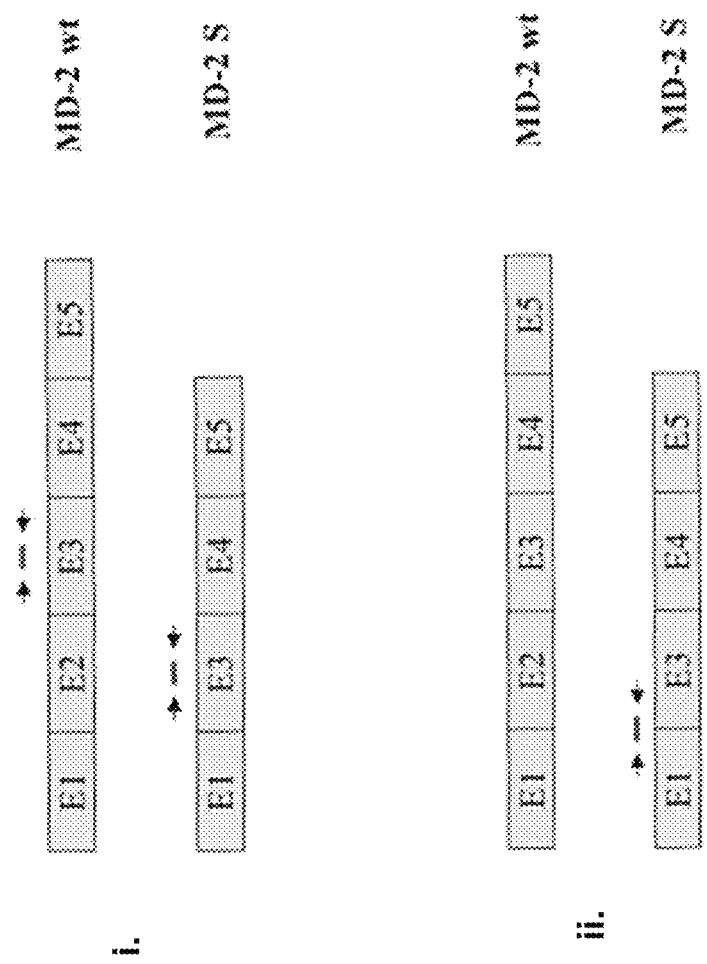
FIGS. 9A-9B depicts the detection of MD-2s in accordance with an embodiment of the present invention. (A) MD-2 probes for real time PCR; (i) MD-2 total probe recognizes both wild-type and MD-2s; (ii) MD-2s probe recognizes only the short isoform of MD-2. (B) Real-time polymerase chain reaction analysis for MD-2 expression: shown are the threshold cycles for total MD-2 (wild-type and short isoform) and short MD-2 in epithelial cells stimulated with IFN-γ and TNF-α. The short MD-2 isoform is not expressed in unstimulated cells (flat blue line). MD-2s (blue=unstimulated; dark blue=IFN-γ; purple=TNF-α stimulation for 8 h). Total MD-2 (red=unstimulated; light blue IFN-γ; blue=TNF-α).
Figure 9B:
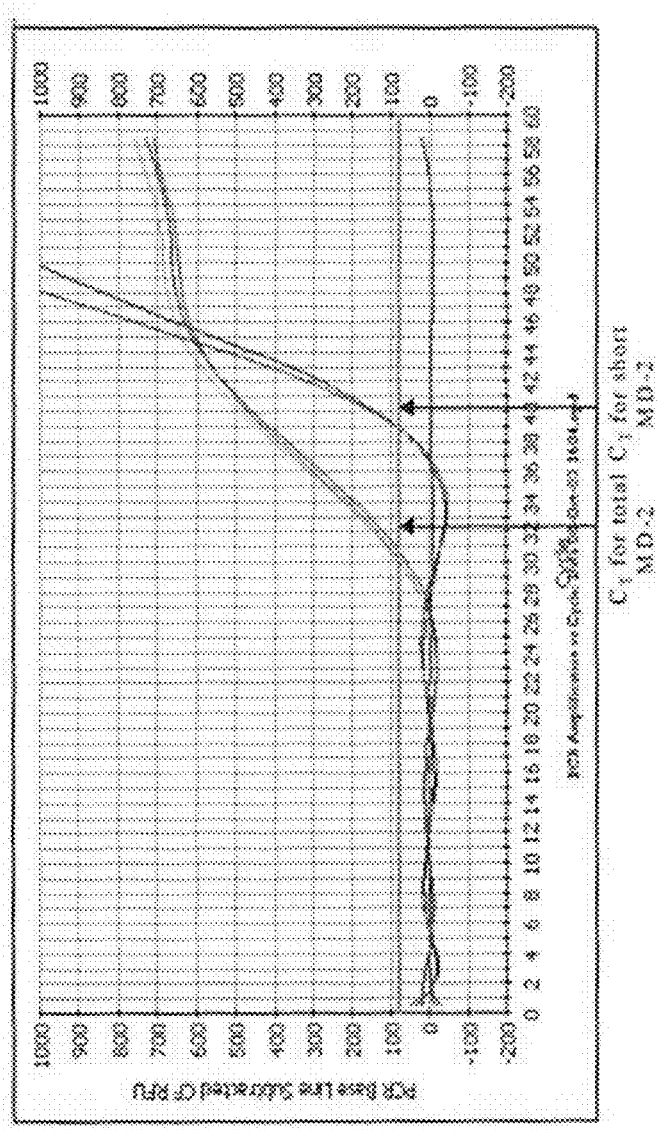
Figure 10:
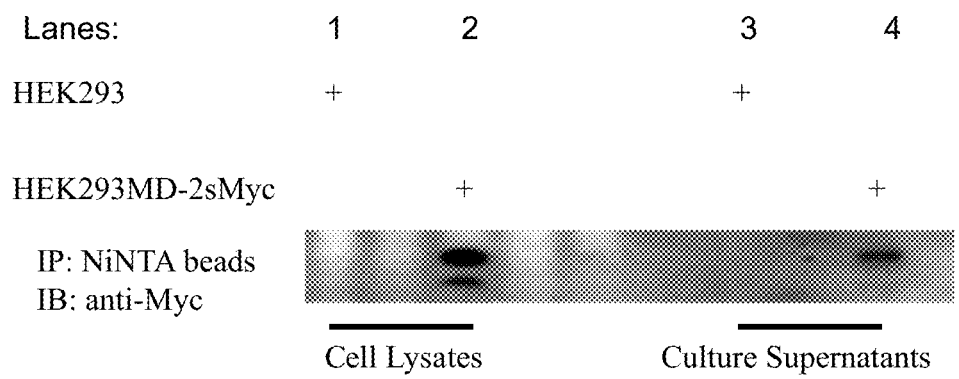
FIG. 10 depicts HEK293 cells transiently transfected with a plasmid expressing MD-2s-Myc (lane 2 and 4) and subsequently treated with G418 in accordance with an embodiment of the present invention. Cell lysates were prepared (lanes 1 and 2) or culture supernatants were collected (lanes 3 and 4). Immunoprecipitations (IP) were performed using Ni-NTA beads. Samples were subsequently analyzed by SDS/PAGE and immunoblotted (IB) with an anti-Myc antibody. HEK293 cells were used as a negative control.

Real-time polymerase chain reaction analysis for MD-2s expression was performed on epithelial cells. The primers/probes for MD-2s are as shown in Table 3. Results are shown in FIG. 9b.

TABLE 3

| Sense | 5'-ATTGGGTCTGCAACTCATCC-3' (SEQ ID NO: 7) |
|---|---|
| Antisense | 5'-CGCTTTGGAAGATTCATGGT-3' (SEQ ID NO: 8) |
| Probe | 5'-CCTACTGTGGGAGAGATTTAAAG-3' (SEQ ID NO: 9) |

Example 12

Flow-Cytometric Analysis of MD-2 and MD-2S Expression

HEK293T cells were retrovirally transduced to generate a cell line stably expressing TLR4-mCitrine. TLR4-mCitrine cells in 12-well dishes were transfected with 300 ng of plasmid encoding myc-tagged MD2 or MD2S using Gene-Juice lipofection reagent (Novagen) and cultured overnight. Cells were dislodged by scraping, washed once with cold PBS and incubated with a 1:50 dilution of anti-myc Alexa 647-conjugated antibody (AbD Serotec) at 4° C. for 30 minutes. Cells were washed four times with PBS for and fluorescence was assessed with an LSR II flow cytometer (BD Biosciences) running FACS Diva software (BD Biosciences). Data was processed using FlowJo software v8.6.3 (Tree Star).

Example 13

Confocal Imaging of MD-2 and MD-2s Transfected Cells

TLR4-mCitrine cells were cultured on glass-bottom confocal dishes (MatTek) coated with collagen. After 24-hours of culture, cells were transfected with up to 300 ng of plasmid encoding myc-tagged MD-2 or MD-2S using Gene-Juice lipofection reagent (Novagen) and cultured for approximately 24 hours. Cells were stained with anti-myc Alexa-647 antibody (AbD Serotec) in culture medium at 4° C. for 20 minutes. Cells were gently washed 3 times with PBS and culture medium was replaced. Cells were imaged at room temperature using an SP2 AOBS confocal laser scanning microscope (Leica Microsystems) running LCS software (Leica Microsystems).

Example 14

MD-2 was Found to be Tyrosine Phosphorylated Upon Stimulation with LPS

Tyrosine phosphorylation of numerous proteins is induced upon stimulation with LPS and indeed the LPS receptor, TLR4, is itself tyrosine phosphorylated. Given the important role of MD-2 following LPS stimulation, the inventors investigated whether MD-2 is posttranslationally modified as well. HEK293 cells were transiently transfected with plasmids expressing Flag-TLR4, Flag-MD-2 and CD14 or mock transfected. 24 hrs later, cells were left untreated or stimulated with LPS for various time points. Proteins were immunoprecipitated from cell extracts with an anti-Flag Ab and analyzed by immunoblotting with an Ab that detects proteins phosphorylated on phosphotyrosine residues. Upon stimulation with LPS, MD-2 was found to be tyrosine phosphorylated (FIG. 13A). The presence of 5 mM phosphotyrosine, a competitive inhibitor, completely abrogated the immunoreactivity detected by the anti-phosphotyrosine Ab, in contrast, phosphoserine or phosphothreonine had no effect on MD-2 tyrosine phosphorylation (data not shown), which confirms the specificity of this result. In addition, MD-2 tyrosine phosphorylation was not observed after stimulation with IL-1β or TNFα or RsDPLA, a biologically inactive analogue of lipid A (data not shown). To further confirm that MD-2 is posttranslationally modified, the inventors pre-treated HEK 293 cells, overexpressing TLR4 and MD-2, with the tyrosine kinase inhibitor herbimycin A for two hours prior to LPS stimulation and observed that herbimycin A significantly inhibited LPS-induced MD-2 tyrosine phosphorylation in a dose dependent manner (FIG. 13B, compare lanes 3 and 4 to lane 2).

Next, the inventors investigated whether MD-2 phosphorylation occurred during trafficking, instead of on the cell surface. More specifically, the inventors examined the role of receptor or ligand internalization and endocytosis on the phosphorylation status of MD-2. Since cytochalasins effectively block LPS internalization and signaling for cytokine release (Poussin et al. (2006) J BIOL CHEM 273, 20285-20291), HEK293 cells, overexpressing TLR4 and MD-2, were pre-treated with Cytochalasin-D for one hour prior to LPS stimulation. The inventors observed that LPS-induced MD-2 tyrosine phosphorylation was significantly inhibited following pretreatment with cytochalasin D (FIG. 13B, lane 5). Thus according to certain embodiments MD-2 tyrosine phosphorylation occurs intracellularly during trafficking and not on the cell surface.

Example 15

Identification of Tyr-22 and Tyr-131 as Possible Phospho-Acceptors

Figure 14:
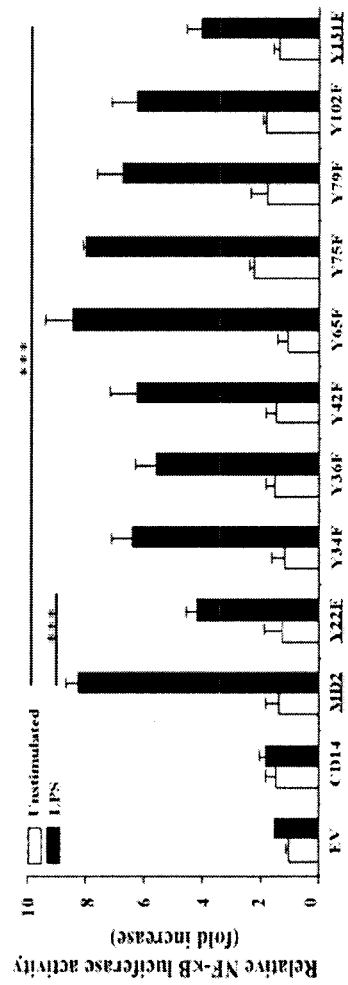
FIGS. 14A-14E show that the mutant proteins MD-2-Y22F, MD-2-Y131F, and MD-2-Y22FY131F do not activate NF-κB as strongly as wild-type MD-2. (A) Schematic diagram showing the location of the tyrosine residues of MD-2. (B) HEK293 cells stably transfected with a NF-κB reporter gene and TLR4 were transiently transfected with wild-type MD-2, MD-2-Y22F, MD-2-Y34F, MD-2-Y36F, MD-2-Y42F, MD-2-Y65F, MD-2-Y75F, MD-2-Y79F, or MD-2-Y131F constructs, for 24 h. Cells were left untreated or stimulated with LPS for 6 hours and luciferase activity measured in cell lysates and expressed as fold induction relative to mock-transfected cells (EV). (C) and (D) HEK293 cells stably transfected with a NF-κB and IL-8 reporter gene and TLR4 were transiently transfected with wild-type MD-2, MD-2-Y22F, MD-2-Y131F, or MD-2-Y22FY131F constructs. Cells were left untreated or stimulated with LPS for 6 hours and luciferase activity measured in cell lysates and expressed as fold induction relative to mock-transfected cells (EV). (E) HEK293 cells were transfected with plasmids expressing the indicated mutant Flag-MD-2 proteins, wild type Flag-MD-2 or empty vector, plus Myc-TLR4 and CD14 constructs. The cells were stimulated with LPS for 15 minutes. Cell lysates were prepared and samples were analyzed by immunoblotting with an p38 or an anti-phospho-p38 antibody. Flag-tagged proteins were immunoprecipitated with an anti-Flag Ab in cell lysates and analyzed by SDS-PAGE and immunoblotted with an anti-phosphotyrosine Ab, or an anti-Flag Ab.
Figure 14:
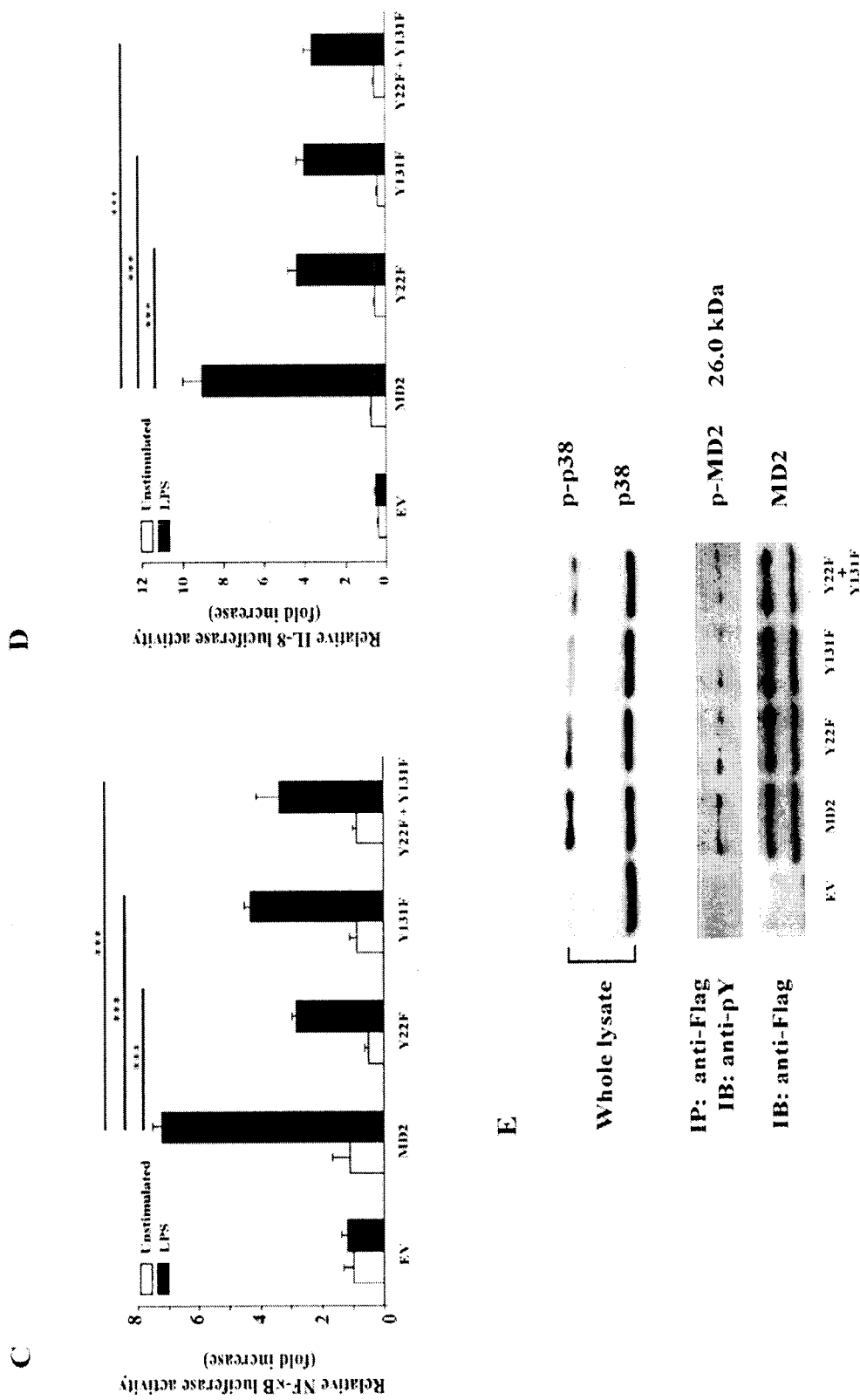

Human MD-2 contains nine tyrosine residues (FIG. 14A). The inventors mutated all nine tyrosine residues conservatively to phenylalanine and tested their ability to respond to LPS. HEK293 cells stably transfected with a NF-κB reporter gene and TLR4 were transiently transfected with plasmids encoding wild-type MD-2, MD-2-Y22F, MD-2-Y34F, MD-2-Y36F, MD-2-Y42F, MD-2-Y65F, MD-2-Y75F, MD-2-Y79F, MD-2-Y102F, or MD-2-Y131F. 24 hrs later, cells were stimulated with LPS. As can be seen in FIG. 14B, upon LPS stimulation the mutant proteins MD-2-Y22F and MD-2-Y131F are significantly less potent in their ability to activate NF-κB compared to wild-type MD-2. Analysis of a double mutant protein, MD-2-Y22F and Y131F, further confirmed that these residues are important for MD-2 to signal NF-κB activation in response to LPS (FIG. 14C). It was also determined that the mutant proteins lacking tyrosine residues located at positions 22 and 131 had a diminished ability to activate IL-8 (FIG. 14D). The inventors further characterized these mutant MD-2 proteins by analyzing their phosphorylation status after LPS stimulation. Supporting the prediction that the sites mutagenized were phosphorylation sites, the mutant proteins were indeed less phosphorylated compared to normal MD-2 (FIG. 14E). Additionally, the amount of phosphorylated p38 after LPS stimulation was measured. Cells transfected with the mutant MD-2 proteins had less phosphor-p38 compared to the normal MD-2 transfected cells, indicating dysfunctional signaling in these cells (FIG. 14E). In addition, it was confirmed that these mutant proteins were secreted (data not shown), and that they displayed a similar glycosylation pattern as wild-type MD-2 upon SDS-PAGE analysis, and that they were expressed at similar levels (FIG. 14E).

Figure 15:
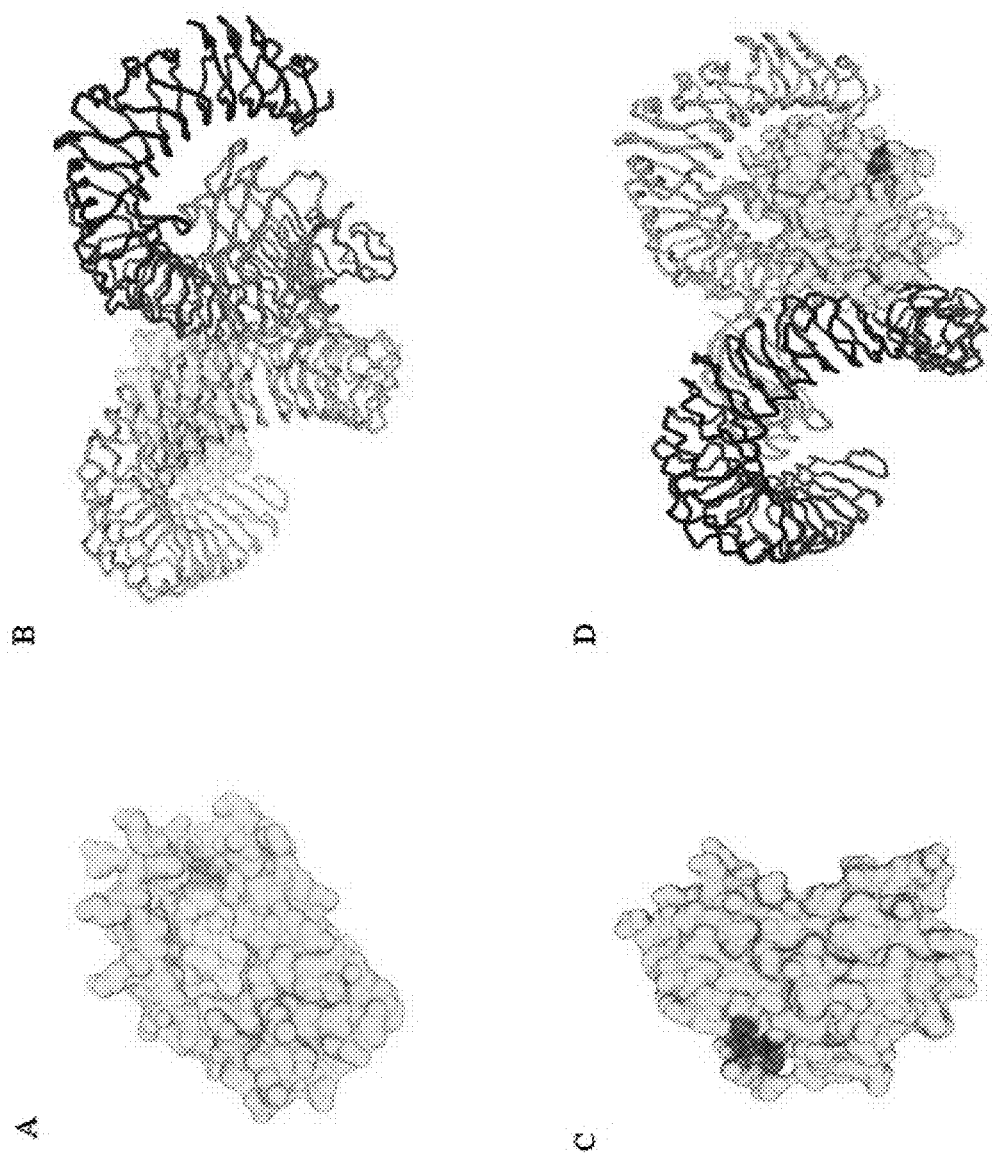
FIGS. 15A-15D depict the structure of the TLR4-MD-2 complex. All figures are based on the published crystal structure of the TLR4-MD-2 receptor complex. The structure with PDB ID: 3FXI was modified with 3-D molecule viewer (a component of vector NTI Advance 11.0-Invitrogen). The surface was calculated using the Conolly method. (A) The structure of MD-2 (yellow) with the location of Y131 depicted in purple. (B) The structure of MD-2 as shown in (A) in complex with TLR-4 (Cyan) and with one more copy of the TLR-4 (blue)-MD-2 (green) complex. (C) Y131 is shown in purple, the overall structure of MD-2 (yellow) with the location of Y22 depicted in purple. (D) The structure of MD-2 as shown in (C) in complex with TLR-4 (Cyan) and with one more copy of TLR-4 (blue)-MD-2(green) complex. The position of Y22 is shown in purple.

Given that it has been shown that Tyr 22 and Tyr 131 are possible phospho-accepting residues, the inventors next determined the location of these residues with respect to the published crystal structure of MD-2. As shown in FIGS. 15 A and C, the hydroxyl-groups of both residues appear to be surface exposed, thereby allowing phosphorylation of these tyrosine residues to occur. Although Tyr 131 is located at the hydrophobic pocket of MD-2, neither Tyr 22 nor 131 are involved in the main dimerization interface of the TLR4-MD-2-LPS complex (FIGS. 15, B and D).

In conclusion, two of the substitutions, MD-2-Y22F and MD-2-Y131F, resulted in a 50% decrease in NF-κB activity upon LPS stimulation, indicating that these residues were critical for maximal NF-κB activation and can be phospho-accepting residues. In addition, by analyzing the published crystal structure of MD-2, the inventors determined that the hydroxyl groups of both MD2 tyrosine residues, located at positions 22 and 131, are surface exposed thereby permitting phosphorylation of the aforementioned residues to occur.

TABLE 4

Y to F sequences of human MD-2.

| | |
|---|---|
| Y22F | MLPFLFFSTLFSSIFTEAQKQFWVCNSSDASISYTYCDKMQYPISINVNPCIE<br>LKRSKGLLHIFYIPRRDLKQLYFNLYITVNTMNLPKRKEVICRGSDDDYSFC<br>RALKGETVNTTISFSFKGIKFSKGKYKCVVEAISGSPEEMLFCLEFVILHQPN<br>SN (SEQ ID NO: 17) |

TABLE 4 -continued

Y to F sequences of human MD-2.

Y34F MLPFLFFSTLFSSIFTEAQKQYWVCNSSDASISFTYCDKMQYPISINVNPCIE
LKRSKGLLHIFYIPRRDLKQLYFNLYITVNTMNLPKRKEVICRGSDDDYSFC
RALKGETVNTTISFSFKGIKFSKGKYKCVVEAISGSPEEMLFCLEFVILHQPN
SN (SEQ ID NO: 18)

Y36F MLPFLFFSTLFSSIFTEAQKQYWVCNSSDASISYTFCDKMQYPISINVNPCIE
LKRSKGLLHIFYIPRRDLKQLYFNLYITVNTMNLPKRKEVICRGSDDDYSFC
RALKGETVNTTISFSFKGIKFSKGKYKCVVEAISGSPEEMLFCLEFVILHQPN
SN (SEQ ID NO: 19)

Y42F MLPFLFFSTLFSSIFTEAQKQYWVCNSSDASISYTYCDKMQFPISINVNPCIE
LKRSKGLLHIFYIPRRDLKQLYFNLYITVNTMNLPKRKEVICRGSDDDYSFC
RALKGETVNTTISFSFKGIKFSKGKYKCVVEAISGSPEEMLFCLEFVILHQPN
SN (SEQ ID NO: 20)

Y65F MLPFLFFSTLFSSIFTEAQKQYWVCNSSDASISYTYCDKMQYPISINVNPCIE
LKRSKGLLHIFFIPRRDLKQLYFNLYITVNTMNLPKRKEVICRGSDDDYSFC
RALKGETVNTTISFSFKGIKFSKGKYKCVVEAISGSPEEMLFCLEFVILHQPN
SN (SEQ ID NO: 21)

Y75F MLPFLFFSTLFSSIFTEAQKQYWVCNSSDASISYTYCDKMQYPISINVNPCIE
LKRSKGLLHIFYIPRRDLKQLFFNLYITVNTMNLPKRKEVICRGSDDDYSFC
RALKGETVNTTISFSFKGIKFSKGKYKCVVEAISGSPEEMLFCLEFVILHQPN
SN (SEQ ID NO: 22)

Y79F MLPFLFFSTLFSSIFTEAQKQYWVCNSSDASISYTYCDKMQYPISINVNPCIE
LKRSKGLLHIFYIPRRDLKQLYFNLFITVNTMNLPKRKEVICRGSDDDYSFC
RALKGETVNTTISFSFKGIKFSKGKYKCVVEAISGSPEEMLFCLEFVILHQPN
SN (SEQ ID NO: 23)

Y102F MLPFLFFSTLFSSIFTEAQKQYWVCNSSDASISYTYCDKMQYPISINVNPCIE
LKRSKGLLHIFYIPRRDLKQLYFNLYITVNTMNLPKRKEVICRGSDDDFSFC
RALKGETVNTTISFSFKGIKFSKGKYKCVVEAISGSPEEMLFCLEFVILHQPN
SN (SEQ ID NO: 24)

Y131F MLPFLFFSTLFSSIFTEAQKQYWVCNSSDASISYTYCDKMQYPISINVNPCIE
LKRSKGLLHIFYIPRRDLKQLYFNLYITVNTMNLPKRKEVICRGSDDDYSFC
RALKGETVNTTISFSFKGIKFSKGKFKCVVEAISGSPEEMLFCLEFVILHQPN
SN (SEQ ID NO: 25)

Y22F + MLPFLFFSTLFSSIFTEAQKQFWVCNSSDASISYTYCDKMQYPISINVNPCIE
Y131F LKRSKGLLHIFYIPRRDLKQLYFNLYITVNTMNLPKRKEVICRGSDDDYSFC
RALKGETVNTTISFSFKGIKFSKGKFKCVVEAISGSPEEMLFCLEFVILHQPN
SN (SEQ ID NO: 26)

Example 16

MD-2 was Shown to Interact with Lyn

Prior studies have shown that the Src kinase, Lyn, is recruited to TLR4 (Medvedev et al. (2007) J BIOL CHEM 282, 16042-16053) as well as to CD14 (Stefanova et al. (1993) J BIOL CHEM 268, 20725-20728). Furthermore it has been suggested that Lyn may be involved in TLR4 tyrosine phosphorylation. Similar to previous results, the inventors found that TLR4 immunoprecipitated with Lyn upon LPS stimulation (FIG. 16A). Given that MD-2 tyrosine phosphorylation was abolished following pretreatment with herbimycin A (FIG. 13B), a potent Src kinase inhibitor, which has been shown to inhibit Lyn activity (June et al. (2006) PROC NATL ACAD SCI USA 87, 7722-7726), Lyn involvement in the phosphorylation of MD-2 was investigated. HEK293 cells were transiently transfected with Myc-TLR4, HA-MD-2, Flag-Lyn and CD14 constructs. HA-tagged proteins were immunoprecipitated from cell lysates with an anti-HA antibody and immunoblotted with an anti-Flag antibody. The inventors observed that Lyn immunoprecipitated with MD-2 (FIG. 16B). However, given that Lyn also immunoprecipitates with TLR4, the inventors examined whether the interaction between MD2 and Lyn was due to a direct interaction. HEK293 cells were transiently transfected with plasmids expressing HA-MD-2 and Flag-Lyn. HA-tagged proteins were then immunoprecipitated and subsequently immunoblotted with an anti-Flag antibody. The inventors discovered that even without the presence of TLR4, MD-2 immunoprecipitated with Lyn, thus confirming that Lyn and MD-2 could directly interact (FIG. 16C). This result thus suggested that Lyn is the most likely kinase that phosphorylates MD2.

Example 17

Lyn Peptide Inhibitor Diminished MD-2 Tyrosine Phosphorylation

Given that MD-2 tyrosine phosphorylation was abolished following pretreatment with herbimycin A, and that MD-2 and Lyn were found to be in a complex together, the inventors confirmed that Lyn was required for MD-2 tyrosine phosphorylation. A Lyn specific peptide inhibitor (Adachi et al. (1999) J IMMUNOL 163, 939-946) was used to examine the effect of inhibiting Lyn activation on MD-2 phosphorylation. HEK 293 cells, overexpressing TLR4, Myc-MD-2 and CD14 were pretreated with the Lyn peptide inhibitor for two hours prior to LPS stimulation. As can be seen in FIG. 17A, the Lyn peptide inhibitor significantly abolished LPS-induced MD-2 tyrosine phosphorylation in a dose dependent manner (FIG. 17A, compare lanes 4-6 to lane 3). Furthermore, following pretreatment with the Lyn peptide inhibitor, LPS-induced activation of IL-8 and NF-κB was abolished in HEK293 cells overexpressing TLR4, CD14 and MD2 (FIG. 17B), thus confirming the important role for Lyn kinase in mediating the signaling of the LPS-MD-2-TLR4-complex.

Example 18

Animals

C57BL/6 mice were used for all of the experiments in this study. For all ALI experiments, C57BL/6 mice were bred in house (originally from The Jackson Laboratory, Bar Harbor, Me.). For all HDM studies, C57BL/6 mice were purchased from The Jackson Laboratory. All animal experiments were performed according to the guidelines and approved protocols of the Institutional Animal Care and Use Committee, Cedars-Sinai Medical Center.

Laboratory animals are maintained in accordance with the applicable portions of the Animal Welfare Act and the guidelines prescribed in the Guide for the Care and Use of Laboratory Animals. Cedars-Sinai Medical Center is fully accredited by the Association for Assessment and Accreditation of Laboratory Animal Care and abides by all applicable laws governing the use of laboratory animals.

Cell Culture

The murine macrophage/monocyte cell line RAW264.7 (BH-AC71; American Type Culture Collection) was maintained in DMEM (Sigma-Aldrich) containing 10% FBS (Hyclone), 100 U/ml penicillin, and 100 U/ml streptomycin. Primary normal human small airway epithelial cells (SAEC) as well as all the basal media and growth supplements were obtained from Lonza (Walkersville, Md.). Cells were cultivated according to the instructions of the manufacturer on plastic dishes or flasks (BD Biosciences, Heidelberg, Germany).

Passage number was kept to less than four passages from original stocks. SAEC were maintained in SAEC basal medium supplemented with 52 mg/ml bovine pituitary extract, 0.5 ng/ml human recombinant epidermal growth factor, 0.5 mg/ml hydrocortisone, 0.5 mg/ml epinephrine, 10 mg/ml transferrin, 5 mg/ml insulin, 0.1 ng/ml retinoic acid, 6.5 ng/ml triiodothyronine, 50 mg/ml Gentamicin/Amphotericin-B (GA-1000), and 50 mg/ml fatty acid-free BSA.

Preparation of Adenoviral Vector Expressing MD-2s-Myc

The human MD-2s gene was cloned into the pEntry CMV-IRES shuttle vector using AgeI-NotI sites. After sequence verification, the pEntry-CMVMD-2s-IRES plasmid was recombined with pDest-Ad plasmid (Life Technologies). The recombinant p-adenovirus construct that expressed MD-2s (Ad-MD-2s) plasmid was selected in DH10B *Escherichia coli* using ampicillin. For generating recombinant Ad-MD-2s virus, the pAd-MD-2s plasmid DNA was transfected into HEK-293 cells. At 10-14 d posttransfection, viral plaques appeared, and the infected cell lysates were harvested. The Ad-MD-2s virus underwent two additional rounds of amplification. The amplified virus was subjected to two rounds of CsCl gradient ultracentrifugation and dialysis. The viral vector titer was measured in HEK-293 cells by serial dilution. A control Ad-EV virus was generated as described above.

Mouse Model of LPS-Induced ALI

Male, 6-8-wk-old C57BL/6 mice (n=8 in each group) received a first generation replication-deficient adenovirus serotype 5 containing human short MD-2s cDNA (Ad-MD-2s) ($1\times10^9$ viral particles in 50 ml PBS) or an empty vector lacking a transgene (Ad-EV) intratracheally (i.t.) 2 d before i.t. instillation of LPS (*E. coli* serotype 0:111; Alpha Chemical and Plastics Co., Hollister, Mo.) at 0.25 mg/kg. The mice were sacrificed 6 h later to evaluate lung injury. For bronchoalveolar lavage fluid (BALF) transfer experiments, 12 mice in each group treated with $1\times10^9$ PFU/mice of Ad-EV or Ad-MD-2s for 48 h and BALF collected, pooled, and concentrated by using centrifugal filter devices (Amicon Ultra-15; Merck Millipore) in sterile condition. A total of 100 ml BALF was administrated i.t. into six naive mice in each group, and 1 h later, mice were treated with 0.25 mg/kg LPS i.t. and sacrificed 6 h later.

Mouse Model of HDM-Induced Allergic Airway Inflammation

Female, 6-8-wk-old C57BL/6 mice (n=10 in each group) received Ad-MD-2s ($5\times10^8$ viral particles in 50 ml PBS), Ad-EV, or PBS. Forty-eight hours later, each of them treated with 50 mg HDM extract of *Dermatophagoides pteronyssinus* (Greer Laboratories, Lenoir, N.C.) once by i.t. for sensitization. Then mice were challenged with 50 mg/mice HDM by i.t. route on day 15 and 18 and sacrificed on day 20. Bronchoalveolar lavage fluid (BALF) and lung homogenate BALF was obtained by cannulating the trachea with a needle and infusing the lungs three times with 0.3 ml PBS. After centrifugation at 2000×g for 10 min, cell-free BALF was collected and kept at −80° C. Total protein quantification in cell-free BALF was accomplished on aliquots of supernatants from all samples with the BCA Protein Assay Reagent Kit (Pierce Biotechnology, Rockford, Ill.). The cell pellet was resuspended in cold PBS, and the total cell counts were determined using a hemacytometer. The number of eosinophils was determined by FACS using PE-conjugated anti-Siglec F Ab. Lung tissues were homogenized in PBS, centrifuged, and supernatant of each sample kept at −80° C.

Inflammatory Mediators and Total Protein Measurement

Inflammatory mediators IL-6, TNF-a, keratinocyte chemoattractant (KC), MIP-2, IL-5, and IL-8 were measured in BALF, supernatants of lung homogenate, and culture medium by using an ELISA kit (BD Biosciences, San Jose, Calif. and R&D Systems, Minneapolis, Minn.) according to the manufacturer's instructions.

Myeloperoxidase Assay

Myeloperoxidase (MPO) activity was measured in the supernatants of lung tissue homogenate. Briefly, the lung tissues were homogenized in PBS and centrifuged. The MPO activity was assayed by measuring the absorbance spectrophotometrically at 450 nm using 0.167 mg/ml O-dianisidine hydrochloride and 0.0005% hydrogen peroxide. Data were expressed as fold increase comparing to PBS group.

Immunohistochemistry

For paraffin sections, tissues were fixed in 10% neutral-buffered formalin and embedded using standard techniques. Sections (5 mm) were cut, deparaffinized, and stained with standard H&E methods to evaluate the tissue histological alterations. For our allergic airway inflammation model, lung sections were also stained with Alcian blue reagent (American MasterTech, Lodi, Calif.) for detecting airway mucus production. For immunofluorescence, the tissues were fixed in 2.5% paraformaldehyde following dehydration with 30% sucrose overnight at 4° C. Transverse lung sections (30 mm) were obtained with a cryostat and processed for immunofluorescence staining. The tissues were then permeabilized and blocked with protein block (DakoCytomation). The sections were stained with combinations of Abs against E-cadherin (BD Biosciences) and anti-Myc conjugated with Alexa Fluor 488 in blocking solution overnight at 4° C. We used the secondary Alexa Fluor 589-conjugated polyclonal donkey anti-rabbit Ab (1:2500; Jackson ImmunoResearch Laboratories) for 1 h incubation. Images were obtained using a BZ-9000 microscope (Keyence, Itasca, Ill.).

Quantitative Real-Time PCR

Total RNA was extracted by the RNeasy extraction kit (Qiagen) and reverse transcribed with the iScript cDNA Synthesis Kit (Bio-Rad, Hercules, Calif.). Real-time PCR was performed using SYBR Green Master Mix (Takara Bio). GAPDH served as a loading control. PCR primers for human IL-8: forward 5'-TCTGGCAACCCTAGTCTGCT-3' (SEQ ID NO:29) and reverse 5'-GCTTCCACATGTCCT-CACAA-3' (SEQ ID NO:30); and human CCL2: forward 5'-ATCCAGCTCCTTCCAGGATT-3' (SEQ ID NO:31) and reverse 5'-ACACACCCACCCTCTCTTTG-3' (SEQ ID NO:32).

Western Blot Assay

Protein concentration was determined by a BCA Protein Assay Kit (Pierce) with BSA used as a standard. Equal amounts of protein were mixed with sample buffer, separated by 10% SDS-PAGE, and transferred onto a polyvinylidene difluoride membrane. Membranes were then incubated in blocking buffer (5% skim milk in 100 mM Tris-HCl [pH 7.5], 150 mM NaCl, and 0.1% Tween-20 [TBST]) for 1 h. Primary Abs were applied in blocking buffer overnight at 4° C. Membranes were washed three times, for 5 min each with TBST, and incubated with a secondary Ab conjugated with HRP (GE Healthcare) in blocking buffer for 1 h at room temperature. After washing the membranes with TBST four times (5 min each), signal was detected by chemiluminescence using the ECL Plus Western blotting Detection kit (GE Healthcare Life Sciences, Piscataway, N.J.) and a Bio-Spectrum UVP Imaging system (Bio-Rad).

Flow Cytometry

To check the overexpression of MD-2s in vitro, the cells were treated with 50:1 multiplicity of infection (MOI) of Ad-EV or Ad-MD-2s for 1 h, the culture medium changed, and then continuously incubated for 48 h. The cells were dislodged by scraping and washed with PBS. After fixation and permeabilization with Cytofix/Cytoperm kit (BD Biosciences), the cells were stained with anti-Myc Alexa Fluor 488 (Santa Cruz Biotechnologies, Santa Cruz, Calif.) on ice for 30 min. Cells were washed twice with PBS before fluorescence measurement. Eosinophil cell numbers were determined by staining with PE-conjugated anti-Siglec F. Fluorescence was assessed with a CyAn flow cytometer (Beckman Coulter), and data were analyzed using Summit (DakoCytomation, Carpinteria, Calif.) software.

Statistical Analysis

Results are expressed as mean 6 SD. Data were analyzed using Student t test. Significant differences were set at $p<0.05$ for all studies. For multiple comparisons, statistical significance was evaluated by one-way ANOVA with the Tukey post hoc test.

Ad-MD-2s-Mediated MD-2s Expression and Inhibition of LPS/TLR4 Signaling in Mouse Macrophages We reported that MD-2s impedes LPS signaling in vitro by competitively inhibiting MD-2 binding to TLR4. To investigate the potential therapeutic effects of MD-2s in vivo, we generated a Myc-tagged MD-2s adenoviral overexpression vector, Ad-MD-2s. Expression was confirmed by flow cytometry using an anti-Myc Ab compared with cells infected with Ad-EV. We next infected RAW 264.7 cells to assess if Ad-MD-2s would inhibit LPS-induced signaling and inflammatory cytokine production. In response to 6-h LPS stimulation, the levels of TNF-a and IL-6 were significantly reduced in Ad-MD-2s-infected cells compared with Ad-EV-infected cells. These data demonstrate that overexpression of MD-2s blunts LPS-mediated proinflammatory responses in cells.

Expression of MD-2s Protein after Ad-MD-2s Administration In Vivo

Figure 18:
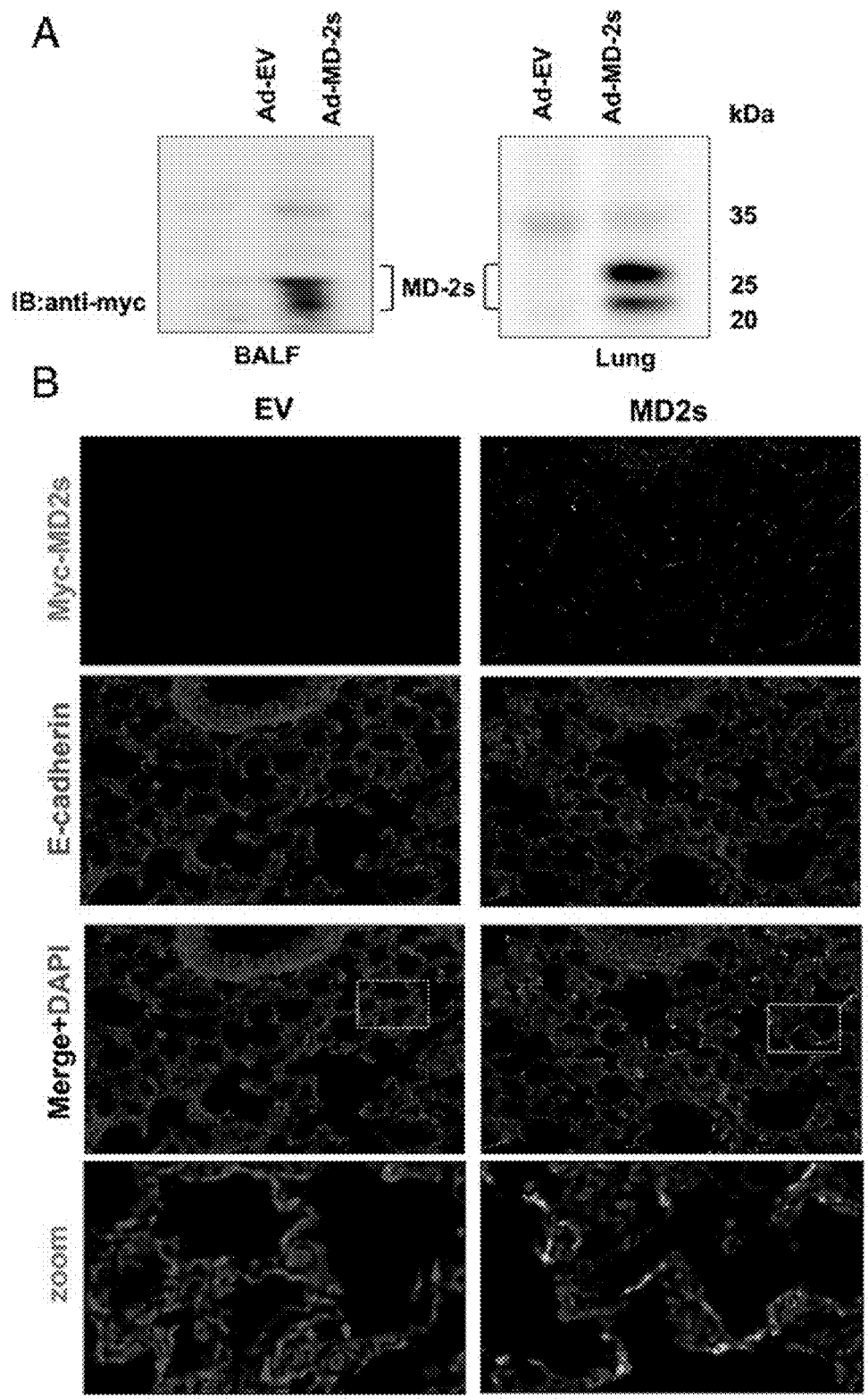
FIGS. 18A-18B depict expression of recombinant adenovirus-mediated MD-2s protein in vivo. Ad-EV or Ad-MD-2s-Myc was administered i.t. to C57BL/6 mice at a dose of $1 \times 10^9$ PFUs/mouse. (A) Forty-eight hours later, BALF was pooled in each group and concentrated. Lung homogenate was prepared. Samples were subsequently analyzed by SDS-PAGE and immunoblotted (IB) with an anti-Myc Ab. (B) Immunofluorescent staining in lung sections. Green: Myc tag of MD-2s protein; red: epithelial cell marker E-cadherin; and blue: nuclei. Photographs are representative examples from each group. Images were taken at original magnification ×40.

To elucidate the immunomodulatory effect of MD-2s in LPS-induced lung damage, we examined if i.t. administration of Ad-MD-2s could elevate MD-2s levels in mouse lung. We administered C57BL/6 mice with $1\times10^9$ PFU Ad-EV or Ad-MD-2s and 48 h later probed for the Myc tag in BALF and lung homogenates. Myc-tagged MD-2s was detected in both the BALF and lung homogenate as two major bands (FIG. 18A), indicating that MD-2s was differentially glycosylated as expected. We used immunofluorescence to determine which cells expressed MD-2s in the lungs. Frozen sections were stained with Abs specific for Myc conjugated with Alexa Fluor 488 (green) and the epithelial cell marker E-cadherin, followed by secondary Ab conjugated with Alexa Fluor 569 (red). MD-2s was seen in the bronchial and alveolar epithelial cells of the lung. There was no detectable Myc signal in Ad-EV-infected lungs (FIG. 18B).

Overexpression of MD-2s Protein Attenuates LPS-Induced Inflammatory Lung Injury

Figure 19:
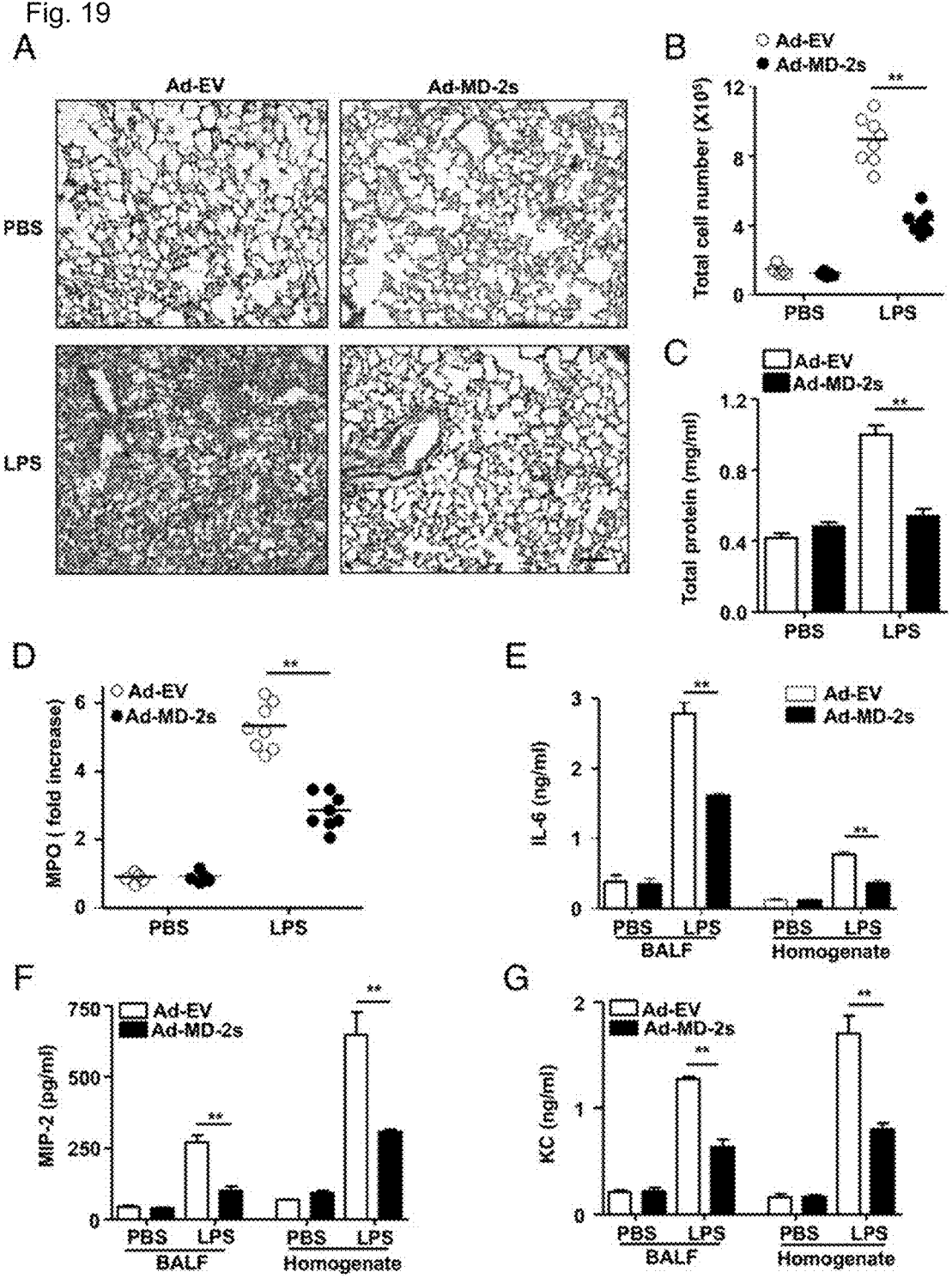
FIGS. 19A-19G show that MD-2s overexpression attenuates lung tissue damage in mice challenged with LPS. Mice (n=8 for each group) received i.t. instillation of Ad-EV or Ad-MD-2s at dose of $1 \times 10^9$ PFU/mice, and 48 h later, LPS (0.25 mg/kg) was administrated i.t. and sacrificed 6 h later. (A) Lungs were collected and stained with H&E for histology (original magnification ×400). Total cell number (B) and protein level (C) in BALF were determined. (D) MPO content was assessed in lung tissue homogenates, as described herein. IL-6 (E), MIP-2 (F), and KC (G) concentrations were determined by ELISA. Data are presented as the mean±SEM. **$p<0.05$.
Figure 20:
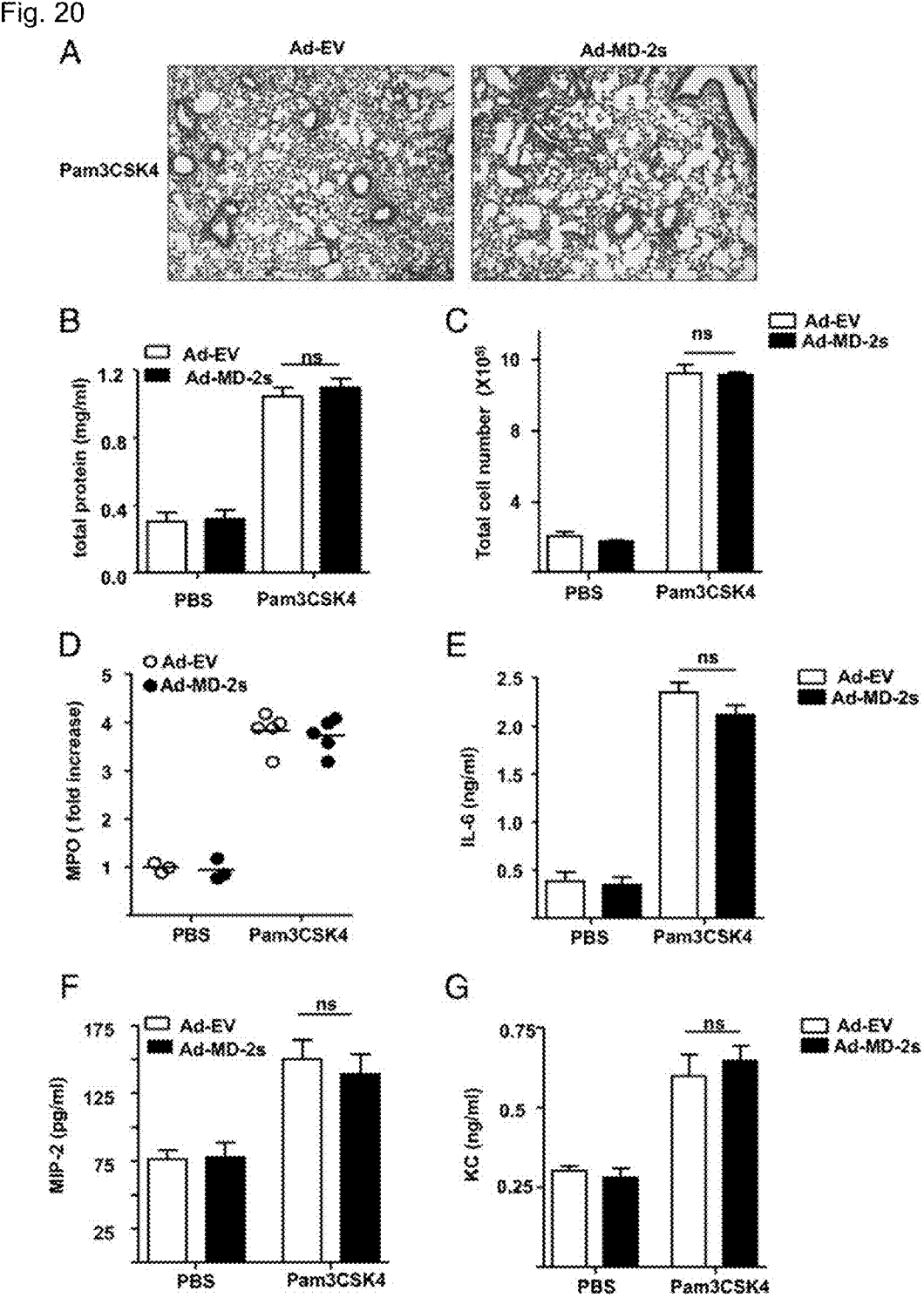
FIGS. 20A-20G show that MD-2s does not prevent Pam3CSK4-induced pulmonary inflammation. Ad-EV or Ad-MD-2s $1 \times 10^9$ PFU was delivered into lungs of mice by i.t. and 48 h later Pam3CSK4 by 0.25 mg/kg or PBS instilled i.t. and sacrificed 6 h later. (A) Lungs were collected and stained with H&E for histology. Original magnification 340. Total protein (B) and total cell number (C) in BALF and MPO activity (D) in lung homogenate was measured by MPO assay. IL-6 (E), MIP-2 (F), and KC (G) were determined in BALF by ELISA. Values are the mean±SD; n=5 for each treatment group and vehicle.

To assess the therapeutic effects of MD-2s in vivo, we infected mice with Ad-EV or AD-MD-2s and then 48 h later challenged them with LPS and assessed pulmonary inflammation 6 h later. In the Ad-EV group, LPS treatment resulted, as expected, in thickened alveolar walls, alveolar congestion, and massive cell infiltration. These pathological changes were clearly attenuated in lungs of MD-2s-overexpressing mice (FIG. 19A). Mice that received Ad-MD-2s had significantly reduced levels of protein and cells in the BALF compared with Ad-EV controls (FIG. 19B, 19C). As a proxy for neutrophil infiltration into the lungs, we measured MPO levels in the lung homogenates and found a significant reduction in enzyme levels in mice that received Ad-MD-2s (FIG. 19D). We next measured the proinflammatory cytokine IL-6, as well as the neutrophil chemokines MIP-2 and KC, and found that all three were significantly reduced in both BALF and lung homogenates in mice that received Ad-MD-2s compared with mice that received the empty vector (FIG. 19E-G). Importantly, adenoviral vector alone did not alter the effects of LPS-induced ALI as measured by cellular recruitment and cytokine production. These observations indicate that Ad-MD-2s treatment attenuated lung injury in response to LPS by reducing vascular leak and decreasing neutrophil influx and production of proinflammatory cytokines and chemokines.

To determine if MD-2s functioned specifically by inhibiting TLR4 signaling and not other TLR pathways, we evaluated the effect of MD-2s on the inflammatory cell accumulation and cytokine production in the lungs following an i.t. challenge with Pam3CSK4, a potent activator of TLR2/TLR1 pathway. Pam3CSK4 induced marked infiltration of inflammatory cells into the alveolar space and protein in the BALF (FIGS. 20A-C) and increased levels of MPO, IL-6, MIP-2, and KC (FIG. 20D-G). However, none of these endpoints differed between Ad-EV- or Ad-MD-2s-infected mice. These data demonstrate that over-expression of MD-2s did not inhibit TLR2-mediated inflammation and support our conclusion that MD-2s acts specifically to blunt TLR4 signaling.

Secreted MD-2s in the BAL Inhibits LPS-Induced Lung Injury

Figure 21:
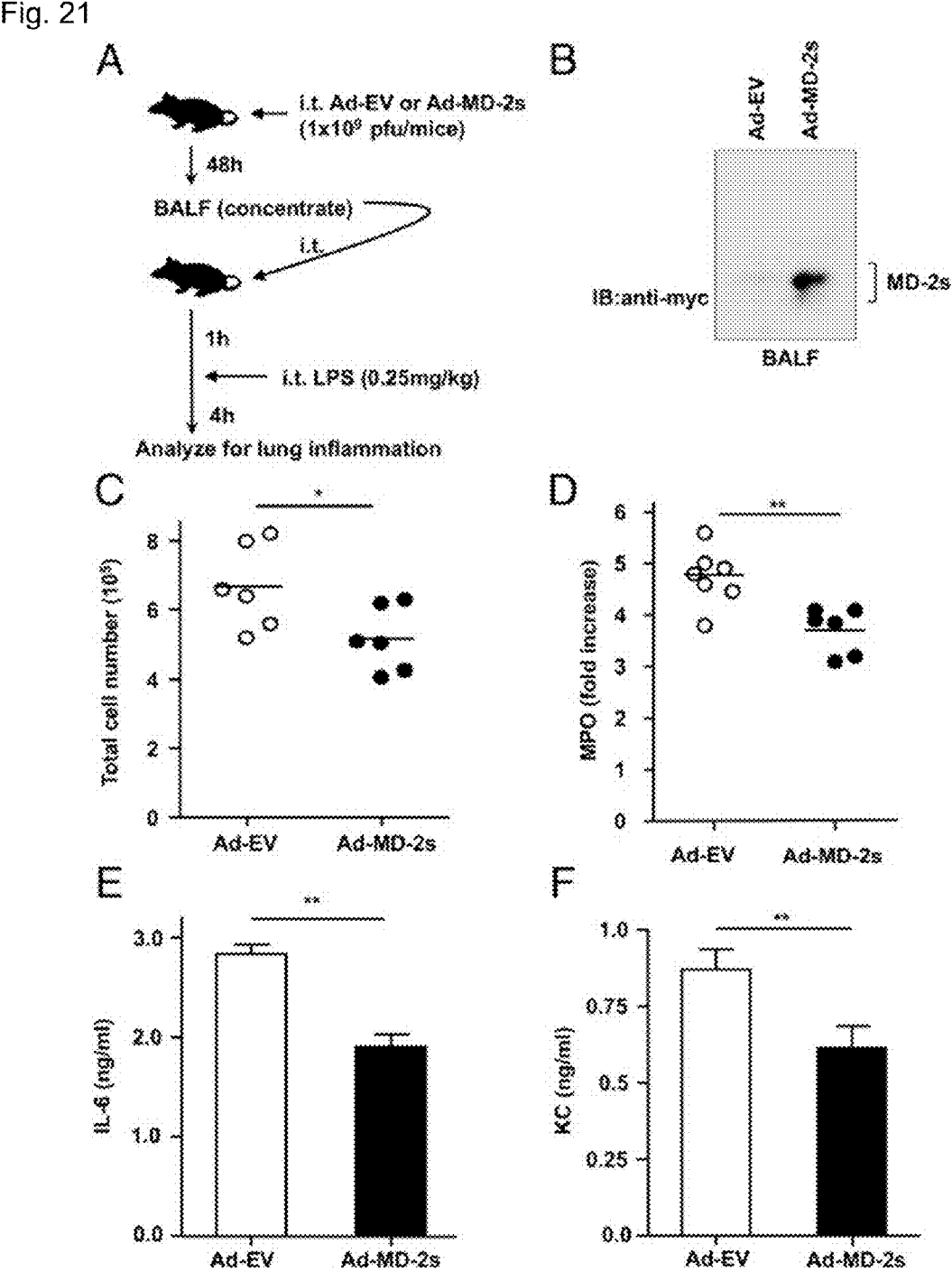
FIGS. 21A-21F show that sMD-2s protein inhibited LPS-induced cytokines and chemokines Ad-EV or Ad-MD-2s $1 \times 10^9$ PFU was delivered into lungs of mice (n=12 for each group). Forty-eight hours later, mice were sacrificed, and BALF was pooled in each group and concentrated. Mice were (n=6 for each group) i.t. administrated with a concentration of BALF (100 ml) 1 h before LPS (0.25 mg/kg, 50 ml) i.t. instillation and sacrificed 6 h later. (A) The schematic view of experiment. (B) The expression of Myc-tagged MD-2s protein in concentrated BALF. Total cell number in BALF (C) and MPO activity (D) in lung homogenate was measured. IL-6 (E) and KC (F) concentrations were determined in BALF by ELISA. Values are the mean±SD. *$p<0.05$, **$p<0.05$. IB, immunoblot.

A soluble form of MD-2 (sMD-2) is markedly elevated in plasma from patients with severe infections and in other fluids from inflamed tissues. sMD-2-LPS complex plays a crucial role in the LPS response by activating epithelial and other TLR4-positive MD-2-negative cells in the inflammatory microenvironment. We reported that MD-2s exists also as a secreted form that retains its TLR4-inhibitory activity in cell models. To assess if soluble MD-2s produced in vivo from Ad-MD-2s could block TLR4 signaling, we transferred BALF from Ad-MD-2s- or Ad-EV-infected mice into naive mice then challenged with LPS (FIG. 21A). sMD-2s in BALF was detected by immunoblotting using anti-Myc Ab (FIG. 21B). Concentrated BALF was administrated i.t. 1 h before instillation of 0.25 mg/kg LPS, and the mice were sacrificed 6 h later. In the group that received Ad-EV BALF, LPS challenge led to increased total cell number and levels of MPO, IL-6, and KC (FIG. 21C-F). The pretreatment of BALF prepared from Ad-MD-2s-treated mice significantly blunted these proinflammatory responses (FIG. 21C-F). The pretreatment of BALF obtained from naive animals had no effect on LPS-induced inflammation. Although it is possible that an unknown factor in the BALF is contributing the inhibition of LPS signaling, the data indicate that it is likely to be the secreted form of MD-2s.

Ad-MD-2s Inhibits HDM-Induced Lung Allergic Inflammation in Mice

Figure 22:
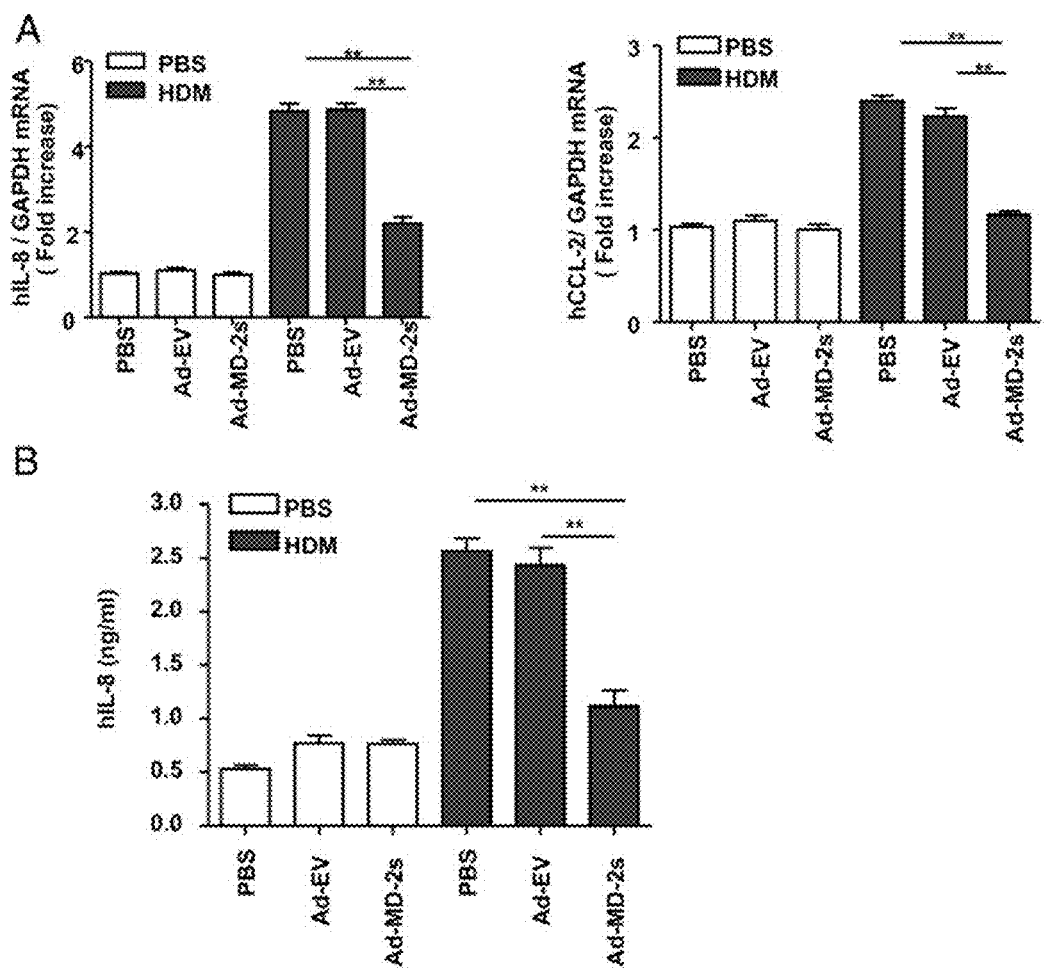
FIGS. 22A-22B show the effect of MD-2s on HDM-induced human SAEC activation. SAECs were transduced with Ad-EV or Ad-MD-2s-Myc of MOI 50:1 for 1 h and, after changing culture medium, incubated further for 48 h. (A) The cells were stimulated with 100 mg/ml of HDM for 8 h. mRNA for IL-8 and CCL-2 expression were examined by real-time PCR. GAPDH served as loading control. (B) After 24-h treatment of HDM, culture medium was collected, and IL-8 production was measured by ELISA. A representative result of three independent experiments. Value are the mean±SD. **$p<0.01$.

Recent publications have described the MD-2-related lipid recognition family of proteins of which MD-2 is the prototypical member. More recently, the HDM major Ag Der p 2 was found to have many common structural and functional characteristics with MD-2. In mouse models of allergic asthma, the effects of Der p 2 are markedly reduced in Tlr4 knockout mice and can be prevented in wild-type mice by administration of a TLR4 antagonist. The bronchiolar-alveolar epithelium is a primary target site for inhaled agents that cause lung injury and releases a broad range of mediators that influence other cell populations. New findings showed epithelial cells are in a pivotal position in the development of allergic inflammation though the activation of the TLR4 signaling pathway. However, in addition to its proinflammatory effects, due to its structural similarities to MD-2, Der p 2 can functionally replace MD-2 and facilitate TLR4 signaling in vitro. To determine if MD-2s inhibits HDM-induced activation of epithelial cells, we measured mRNA expression of CCL2 and IL-8, and the release of IL-8 protein from human primary SAEC. The cells were transduced with Ad-EV or Ad-MD-2s at 50:1 MOI for 1 h, washed, and incubated for 48 h. The cells were then stimulated with HDM or PBS. As expected, HDM stimulated the expression of CCL-2 and IL-8 mRNA as well as IL-8 secretion. However, transduction with Ad-MD-2s significantly inhibited the induction of these cytokines (FIG. 22). We also performed similar experiments using the human bronchial epithelial cell line (BEAS-2b) and obtained the same results (data not shown). These data demonstrate that MD-2s inhibits the expression of inflammatory mediators CCL-2 and IL-8 by airway epithelial cells exposed to HDM.

Figure 23:
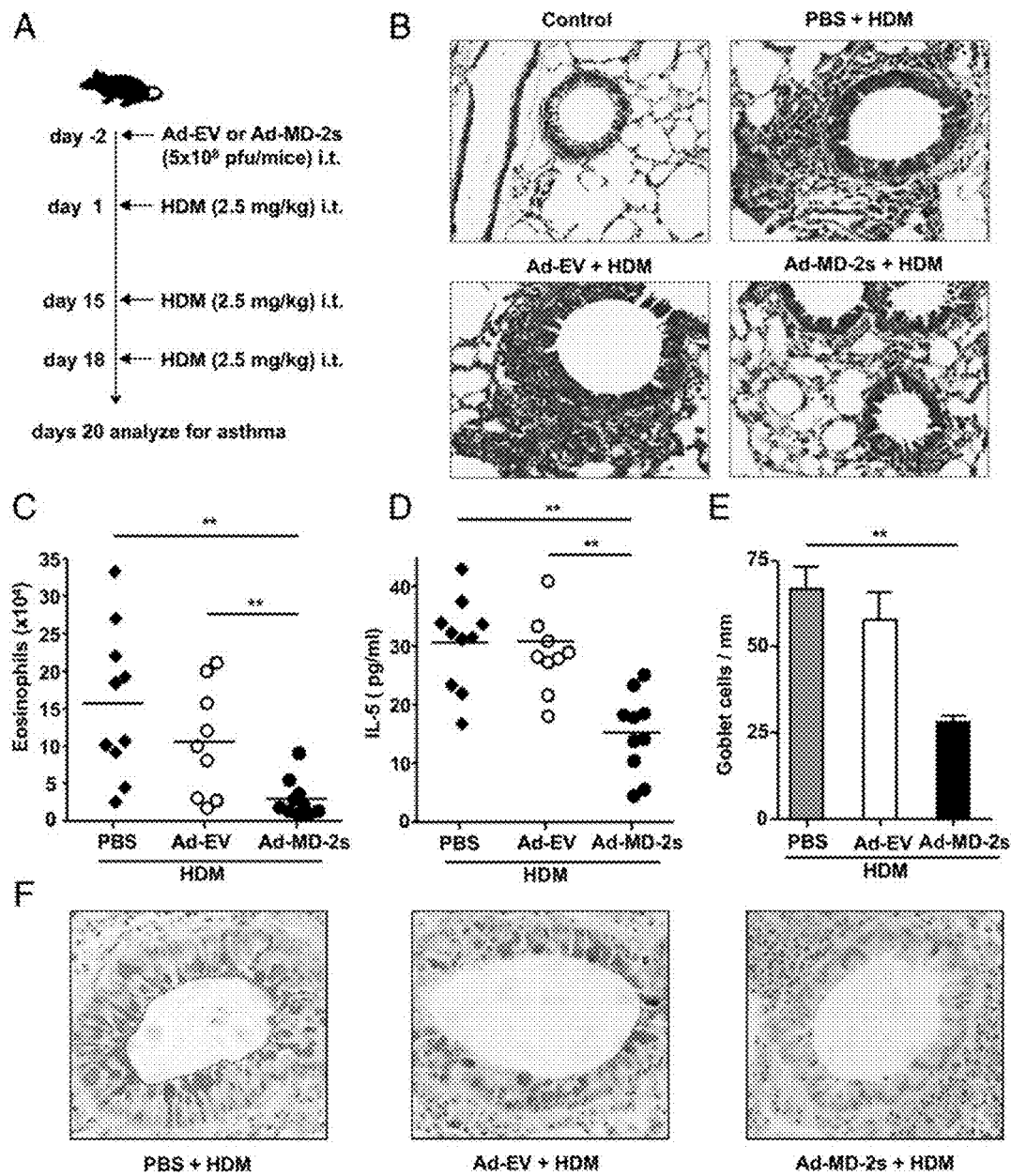
FIGS. 23A-23F show that alleviation of allergic lung inflammation in HDM-challenged mice pretreated with Ad-MD2s. (A) Schematic protocol. The mice were treated with PBS, Ad-EV, or Ad-MD2s (n=10 for each group) at $5 \times 10^8$ PFU/mice for 48 h. Sensitization on day 1 and challenge on days 14 and 18 with HDM at 50 mg/mice were performed by i.t. administration. Then at day 20, mice were sacrificed. (B) Lung sections were stained with H&E for measurement of cellular infiltration of the peri-airway region. Original magnification ×40. (C) The number of eosinophils measured by FACS. (D) Level of IL-5 in the BALF by ELISA. (E) The number of goblet cells in airway. Data are the mean 6 SEM and representative of eight mice evaluated in each group (one-way ANOVA [Tukey post hoc]; **p<0.001). (F) A representative picture of each group. Original magnification ×40.

To explore further if MD-2s has a protective effect on allergic airway inflammation in vivo, we used the HDM-induced allergic inflammation model in mice. This model exhibits a number of features of human allergic airway inflammation including cellular infiltration into the lungs, increase in eosinophil numbers, and elevated levels of inflammatory cytokines in BAL fluid. As shown in FIG. 23A, mice were treated with Ad-EV or Ad-MD-2s (n=10 for each group) at $5 \times 10^8$ PFU/mice for 48 h, followed by sensitization with 50 mg HDM given by i.t. route. Mice were then challenged with 50 mg HDM on days 15 and 18 postsensitization and sacrificed on day 20 (FIG. 23A). Sections of the lungs stained with H&E showed marked histological alterations such as peribronchial and perivascular cell infiltration in the airway after HDM challenge in the PBS- or Ad-EV-pretreated groups. However, these changes were reduced in the mice that were treated with AD-MD-2s (FIG. 23B). MD-2s overexpression during sensitization also significantly reduced the influx of eosinophils into the airways, as well as the level of the Th2-associated cytokine IL-5 (p, 0.01) (FIG. 23C, 23D). Finally, MD-2s overexpression significantly reduced goblet cell hyperplasia and airway mucus production in murine lung when compared with mice treated with PBS or Ad-EV prior to HDM sensitization (FIG. 23E, 23F). It should be noted although there were no differences found between PBS groups and empty vector, there was a trend for reduced eosinophils with the vector control. It is possible that adenoviral transduction slightly inhibited Th2 responses by the induction of type I IFN. However, it is clear that MD-2s significantly reduced the overall allergic airway inflammation compared with both controls. These results indicate that in addition to inhibiting LPS-induced ALI, MD-2s can also inhibit HDM-induced allergic lung inflammation in mice.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method of inhibiting lipopolysaccharide ("LPS") induced lung inflammation in a subject in need thereof, comprising:
   providing a purified polypeptide comprising an amino acid sequence that is at least 85% identical to SEQ ID NO:1 or SEQ ID NO:2; and
   administering the polypeptide to the subject to inhibit LPS induced lung inflammation.

2. The method of claim 1, wherein the polypeptide comprises the amino acid sequence of SEQ ID NO:1.

3. The method of claim 1, wherein the polypeptide is glycosylated.

4. The method of claim 1, wherein the polypeptide comprises the amino acid sequence of SEQ ID NO:2.

5. The method of claim 1, wherein the purified polypeptide comprising an amino acid sequence that is at least 90% identical to SEQ ID NO:1 or SEQ ID NO:2.

6. The method of claim 1, wherein the purified polypeptide comprising an amino acid sequence that is at least 95% identical to SEQ ID NO:1 or SEQ ID NO:2.

7. The method of claim 1, wherein the purified polypeptide comprising an amino acid sequence that is at least 99% identical to SEQ ID NO:1 or SEQ ID NO:2.

8. A method of treating asthma, allergic asthma, house dust mite (HDM)-induced allergic airway inflammation, perennial rhinitis, or atopic dermatitis (AD) in a subject in need thereof, comprising:
   providing a purified polypeptide comprising an amino acid sequence that is at least 85% identical to SEQ ID NO:1 or SEQ ID NO:2; and administering the polypeptide to the subject to treat asthma, allergic asthma, house dust mite (HDM)-induced allergic airway inflammation, perennial rhinitis, or atopic dermatitis (AD).

9. The method of claim 8, wherein the polypeptide comprises the amino acid sequence of SEQ ID NO:1.

10. The method of claim 8, wherein the polypeptide is glycosylated.

11. The method of claim 8, wherein the polypeptide comprises the amino acid sequence of SEQ ID NO:2.

12. The method of claim 8, wherein the purified polypeptide comprising an amino acid sequence that is at least 90% identical to SEQ ID NO:1 or SEQ ID NO:2.

13. The method of claim 8, wherein the purified polypeptide comprising an amino acid sequence that is at least 95% identical to SEQ ID NO:1 or SEQ ID NO:2.

14. The method of claim 8, wherein the purified polypeptide comprising an amino acid sequence that is at least 99% identical to SEQ ID NO:1 or SEQ ID NO:2.

* * * * *

UNITED STATES PATENT AND TRADEMARK OFFICE
CERTIFICATE OF CORRECTION

PATENT NO. : 9,512,196 B2
APPLICATION NO. : 14/639782
DATED : December 6, 2016
INVENTOR(S) : Arditi et al.

Page 1 of 1

It is certified that error appears in the above-identified patent and that said Letters Patent is hereby corrected as shown below:

Column 1, Lines 19-25, cancel:
"STATEMENT REGARDING FEDERALLY-SPONSORED RESEARCH
This invention was made with Government support under Grant Nos. AI058128 and HL066436 awarded by the National Institute of Health. The Government has certain rights in the invention."

and insert:
--STATEMENT REGARDING FEDERALLY SPONSORED RESEARCH OR DEVELOPMENT
This invention was made with government support under Grant Nos. AI058128 and HL068436 awarded by National Institutes of Health. The government has certain rights in the invention.--

Signed and Sealed this
Twenty-eighth Day of February, 2017

Michelle K. Lee
*Director of the United States Patent and Trademark Office*

SEQUENCE LISTING

<160> NUMBER OF SEQ ID NOS: 32

<210> SEQ ID NO 1
<211> LENGTH: 130
<212> TYPE: PRT
<213> ORGANISM: Homo sapiens

<400> SEQUENCE: 1

Met Leu Pro Phe Leu Phe Phe Ser Thr Leu Phe Ser Ser Ile Phe Thr
1               5                   10                  15

Glu Ala Gln Lys Gln Tyr Trp Val Cys Asn Ser Ser Asp Ala Ser Ile
            20                  25                  30

Ser Tyr Thr Tyr Cys Gly Arg Asp Leu Lys Gln Leu Tyr Phe Asn Leu
        35                  40                  45

Tyr Ile Thr Val Asn Thr Met Asn Leu Pro Lys Arg Lys Glu Val Ile
    50                  55                  60

Cys Arg Gly Ser Asp Asp Asp Tyr Ser Phe Cys Arg Ala Leu Lys Gly
65                  70                  75                  80

Glu Thr Val Asn Thr Thr Ile Ser Phe Ser Phe Lys Gly Ile Lys Phe
                85                  90                  95

Ser Lys Gly Lys Tyr Lys Cys Val Val Glu Ala Ile Ser Gly Ser Pro
            100                 105                 110

Glu Glu Met Leu Phe Cys Leu Glu Phe Val Ile Leu His Gln Pro Asn
        115                 120                 125

Ser Asn
    130

<210> SEQ ID NO 2
<211> LENGTH: 114
<212> TYPE: PRT
<213> ORGANISM: Homo sapiens

<400> SEQUENCE: 2

Glu Ala Gln Lys Gln Tyr Trp Val Cys Asn Ser Ser Asp Ala Ser Ile
1               5                   10                  15

Ser Tyr Thr Tyr Cys Gly Arg Asp Leu Lys Gln Leu Tyr Phe Asn Leu
            20                  25                  30

Tyr Ile Thr Val Asn Thr Met Asn Leu Pro Lys Arg Lys Glu Val Ile
        35                  40                  45

Cys Arg Gly Ser Asp Asp Asp Tyr Ser Phe Cys Arg Ala Leu Lys Gly
    50                  55                  60

Glu Thr Val Asn Thr Thr Ile Ser Phe Ser Phe Lys Gly Ile Lys Phe
65                  70                  75                  80

Ser Lys Gly Lys Tyr Lys Cys Val Val Glu Ala Ile Ser Gly Ser Pro
                85                  90                  95

Glu Glu Met Leu Phe Cys Leu Glu Phe Val Ile Leu His Gln Pro Asn
            100                 105                 110

Ser Asn

<210> SEQ ID NO 3
<211> LENGTH: 29
<212> TYPE: PRT
<213> ORGANISM: Homo sapiens

<400> SEQUENCE: 3

Lys Met Gln Tyr Pro Ile Ser Ile Asn Val Asn Pro Cys Ile Glu Leu
1               5                   10                  15

Lys Gly Ser Lys Gly Leu Leu His Ile Phe Tyr Ile Pro
            20                  25

<210> SEQ ID NO 4
<211> LENGTH: 393
<212> TYPE: DNA
<213> ORGANISM: Homo sapiens

<400> SEQUENCE: 4

| | | | | | |
|---|---|---|---|---|---|
| atgttaccat | ttctgttttt | ttccaccctg | ttttcttcca | tatttactga | agctcagaag | 60 |
| cagtattggg | tctgcaactc | atccgatgca | agtatttcat | acacctactg | tgggagagat | 120 |
| ttaaagcaat | tatatttcaa | tctctatata | actgtcaaca | ccatgaatct | tccaaagcgc | 180 |
| aaagaagtta | tttgccgagg | atctgatgac | gattactctt | tttgcagagc | tctgaaggga | 240 |
| gagactgtga | atacaacaat | atcattctcc | ttcaagggaa | taaaattttc | taagggaaaa | 300 |
| tacaaatgtg | ttgttgaagc | tatttctggg | agcccagaag | aaatgctctt | tgcttggag | 360 |
| tttgtcatcc | tacaccaacc | taattcaaat | tag | | | 393 |

<210> SEQ ID NO 5
<211> LENGTH: 345
<212> TYPE: DNA
<213> ORGANISM: Homo sapiens

<400> SEQUENCE: 5

| | | | | | |
|---|---|---|---|---|---|
| gaagctcaga | agcagtattg | ggtctgcaac | tcatccgatg | caagtatttc | atacacctac | 60 |
| tgtgggagag | atttaaagca | attatatttc | aatctctata | taactgtcaa | caccatgaat | 120 |
| cttccaaagc | gcaaagaagt | tatttgccga | ggatctgatg | acgattactc | tttttgcaga | 180 |
| gctctgaagg | gagagactgt | gaatacaaca | atatcattct | ccttcaaggg | aataaaattt | 240 |
| tctaagggaa | aatacaaatg | tgttgttgaa | gctatttctg | ggagcccaga | agaaatgctc | 300 |
| ttttgcttgg | agtttgtcat | cctacaccaa | cctaattcaa | attag | | 345 |

<210> SEQ ID NO 6
<211> LENGTH: 90
<212> TYPE: DNA
<213> ORGANISM: Homo sapiens

<400> SEQUENCE: 6

| | | | | | |
|---|---|---|---|---|---|
| ataaaatgca | atacccaatt | tcaattaatg | ttaacccctg | tctagaattg | aaaagatcca | 60 |
| aaggattatt | gcacattttc | tacattccaa | | | | 90 |

<210> SEQ ID NO 7
<211> LENGTH: 20
<212> TYPE: DNA
<213> ORGANISM: Artificial Sequence
<220> FEATURE:
<223> OTHER INFORMATION: synthetic construct

<400> SEQUENCE: 7
attgggtctg caactcatcc     20

<210> SEQ ID NO 8
<211> LENGTH: 20
<212> TYPE: DNA
<213> ORGANISM: Artificial Sequence
<220> FEATURE:
<223> OTHER INFORMATION: synthetic construct

<400> SEQUENCE: 8
cgctttggaa gattcatggt                                              20

<210> SEQ ID NO 9
<211> LENGTH: 23
<212> TYPE: DNA
<213> ORGANISM: Artificial Sequence
<220> FEATURE:
<223> OTHER INFORMATION: Synthetic Construct

<400> SEQUENCE: 9
cctactgtgg gagagattta aag                                          23

<210> SEQ ID NO 10
<211> LENGTH: 18
<212> TYPE: DNA
<213> ORGANISM: Homo sapiens

<400> SEQUENCE: 10
atgttaccat ttctgttt                                                18

<210> SEQ ID NO 11
<211> LENGTH: 18
<212> TYPE: DNA
<213> ORGANISM: Homo sapiens

<400> SEQUENCE: 11
ctaatttgaa ttaggttg                                                18

<210> SEQ ID NO 12
<211> LENGTH: 18
<212> TYPE: DNA
<213> ORGANISM: Mus

<400> SEQUENCE: 12
tctgcaactc ctccgatg                                                18

<210> SEQ ID NO 13
<211> LENGTH: 18
<212> TYPE: DNA
<213> ORGANISM: Mus

<400> SEQUENCE: 13
ggcggtgaat gatggtga                                                18

<210> SEQ ID NO 14
<211> LENGTH: 25
<212> TYPE: DNA
<213> ORGANISM: Homo sapiens

<400> SEQUENCE: 14
ttgacattat ctttattgct tttag                                        25

<210> SEQ ID NO 15
<211> LENGTH: 24
<212> TYPE: DNA
<213> ORGANISM: Mus

<400> SEQUENCE: 15
ttgtattttc ttcattcctt ttag                                         24

<210> SEQ ID NO 16
<211> LENGTH: 140
<212> TYPE: DNA
<213> ORGANISM: Homo sapiens

```
<400> SEQUENCE: 16
ttgacattat ctttattgct tttagataaa atgcaatacc caatttcaat taatgttaac     60
ccctgtctag aattgaaaag atccaaagga ttattgcaca ttttctacat tccaagtaag    120
ttcaaatttt tgcttttata                                                140

<210> SEQ ID NO 17
<211> LENGTH: 160
<212> TYPE: PRT
<213> ORGANISM: Artificial Sequence
<220> FEATURE:
<223> OTHER INFORMATION: Tyrosine to phenylalanine mutation at position
      22 of human MD-2

<400> SEQUENCE: 17

Met Leu Pro Phe Leu Phe Phe Ser Thr Leu Phe Ser Ser Ile Phe Thr
1               5                   10                  15

Glu Ala Gln Lys Gln Phe Trp Val Cys Asn Ser Ser Asp Ala Ser Ile
            20                  25                  30

Ser Tyr Thr Tyr Cys Asp Lys Met Gln Tyr Pro Ile Ser Ile Asn Val
        35                  40                  45

Asn Pro Cys Ile Glu Leu Lys Arg Ser Lys Gly Leu Leu His Ile Phe
    50                  55                  60

Tyr Ile Pro Arg Arg Asp Leu Lys Gln Leu Tyr Phe Asn Leu Tyr Ile
65                  70                  75                  80

Thr Val Asn Thr Met Asn Leu Pro Lys Arg Lys Glu Val Ile Cys Arg
                85                  90                  95

Gly Ser Asp Asp Asp Tyr Ser Phe Cys Arg Ala Leu Lys Gly Glu Thr
            100                 105                 110

Val Asn Thr Thr Ile Ser Phe Ser Phe Lys Gly Ile Lys Phe Ser Lys
        115                 120                 125

Gly Lys Tyr Lys Cys Val Val Glu Ala Ile Ser Gly Ser Pro Glu Glu
    130                 135                 140

Met Leu Phe Cys Leu Glu Phe Val Ile Leu His Gln Pro Asn Ser Asn
145                 150                 155                 160

<210> SEQ ID NO 18
<211> LENGTH: 160
<212> TYPE: PRT
<213> ORGANISM: Artificial Sequence
<220> FEATURE:
<223> OTHER INFORMATION: Tyrosine to phenylalanine mutation at position
      34 of human MD-2

<400> SEQUENCE: 18

Met Leu Pro Phe Leu Phe Phe Ser Thr Leu Phe Ser Ser Ile Phe Thr
1               5                   10                  15

Glu Ala Gln Lys Gln Tyr Trp Val Cys Asn Ser Ser Asp Ala Ser Ile
            20                  25                  30

Ser Phe Thr Tyr Cys Asp Lys Met Gln Tyr Pro Ile Ser Ile Asn Val
        35                  40                  45

Asn Pro Cys Ile Glu Leu Lys Arg Ser Lys Gly Leu Leu His Ile Phe
    50                  55                  60

Tyr Ile Pro Arg Arg Asp Leu Lys Gln Leu Tyr Phe Asn Leu Tyr Ile
65                  70                  75                  80

Thr Val Asn Thr Met Asn Leu Pro Lys Arg Lys Glu Val Ile Cys Arg
                85                  90                  95
```

```
Gly Ser Asp Asp Asp Tyr Ser Phe Cys Arg Ala Leu Lys Gly Glu Thr
            100                 105                 110

Val Asn Thr Thr Ile Ser Phe Ser Phe Lys Gly Ile Lys Phe Ser Lys
        115                 120                 125

Gly Lys Tyr Lys Cys Val Val Glu Ala Ile Ser Gly Ser Pro Glu Glu
    130                 135                 140

Met Leu Phe Cys Leu Glu Phe Val Ile Leu His Gln Pro Asn Ser Asn
145                 150                 155                 160
```

<210> SEQ ID NO 19
<211> LENGTH: 160
<212> TYPE: PRT
<213> ORGANISM: Artificial Sequence
<220> FEATURE:
<223> OTHER INFORMATION: Tyrosine to phenylalanine mutation at position
      36 of human MD-2

<400> SEQUENCE: 19

```
Met Leu Pro Phe Leu Phe Phe Ser Thr Leu Phe Ser Ser Ile Phe Thr
1               5                   10                  15

Glu Ala Gln Lys Gln Tyr Trp Val Cys Asn Ser Ser Asp Ala Ser Ile
            20                  25                  30

Ser Tyr Thr Phe Cys Asp Lys Met Gln Tyr Pro Ile Ser Ile Asn Val
        35                  40                  45

Asn Pro Cys Ile Glu Leu Lys Arg Ser Lys Gly Leu Leu His Ile Phe
    50                  55                  60

Tyr Ile Pro Arg Arg Asp Leu Lys Gln Leu Tyr Phe Asn Leu Tyr Ile
65                  70                  75                  80

Thr Val Asn Thr Met Asn Leu Pro Lys Arg Lys Glu Val Ile Cys Arg
                85                  90                  95

Gly Ser Asp Asp Asp Tyr Ser Phe Cys Arg Ala Leu Lys Gly Glu Thr
            100                 105                 110

Val Asn Thr Thr Ile Ser Phe Ser Phe Lys Gly Ile Lys Phe Ser Lys
        115                 120                 125

Gly Lys Tyr Lys Cys Val Val Glu Ala Ile Ser Gly Ser Pro Glu Glu
    130                 135                 140

Met Leu Phe Cys Leu Glu Phe Val Ile Leu His Gln Pro Asn Ser Asn
145                 150                 155                 160
```

<210> SEQ ID NO 20
<211> LENGTH: 160
<212> TYPE: PRT
<213> ORGANISM: Artificial Sequence
<220> FEATURE:
<223> OTHER INFORMATION: Tyrosine to phenylalanine mutation at position
      42 of human MD-2

<400> SEQUENCE: 20

```
Met Leu Pro Phe Leu Phe Phe Ser Thr Leu Phe Ser Ser Ile Phe Thr
1               5                   10                  15

Glu Ala Gln Lys Gln Tyr Trp Val Cys Asn Ser Ser Asp Ala Ser Ile
            20                  25                  30

Ser Tyr Thr Tyr Cys Asp Lys Met Gln Phe Pro Ile Ser Ile Asn Val
        35                  40                  45

Asn Pro Cys Ile Glu Leu Lys Arg Ser Lys Gly Leu Leu His Ile Phe
    50                  55                  60

Tyr Ile Pro Arg Arg Asp Leu Lys Gln Leu Tyr Phe Asn Leu Tyr Ile
65                  70                  75                  80
```

Thr Val Asn Thr Met Asn Leu Pro Lys Arg Lys Glu Val Ile Cys Arg
                85                  90                  95

Gly Ser Asp Asp Asp Tyr Ser Phe Cys Arg Ala Leu Lys Gly Glu Thr
            100                 105                 110

Val Asn Thr Thr Ile Ser Phe Ser Phe Lys Gly Ile Lys Phe Ser Lys
        115                 120                 125

Gly Lys Tyr Lys Cys Val Val Glu Ala Ile Ser Gly Ser Pro Glu Glu
    130                 135                 140

Met Leu Phe Cys Leu Glu Phe Val Ile Leu His Gln Pro Asn Ser Asn
145                 150                 155                 160

<210> SEQ ID NO 21
<211> LENGTH: 160
<212> TYPE: PRT
<213> ORGANISM: Artificial Sequence
<220> FEATURE:
<223> OTHER INFORMATION: Tyrosine to phenylalanine mutation at position
      65 of human MD-2

<400> SEQUENCE: 21

Met Leu Pro Phe Leu Phe Phe Ser Thr Leu Phe Ser Ser Ile Phe Thr
1               5                   10                  15

Glu Ala Gln Lys Gln Tyr Trp Val Cys Asn Ser Ser Asp Ala Ser Ile
            20                  25                  30

Ser Tyr Thr Tyr Cys Asp Lys Met Gln Tyr Pro Ile Ser Ile Asn Val
        35                  40                  45

Asn Pro Cys Ile Glu Leu Lys Arg Ser Lys Gly Leu Leu His Ile Phe
    50                  55                  60

Phe Ile Pro Arg Arg Asp Leu Lys Gln Leu Tyr Phe Asn Leu Tyr Ile
65                  70                  75                  80

Thr Val Asn Thr Met Asn Leu Pro Lys Arg Lys Glu Val Ile Cys Arg
                85                  90                  95

Gly Ser Asp Asp Asp Tyr Ser Phe Cys Arg Ala Leu Lys Gly Glu Thr
            100                 105                 110

Val Asn Thr Thr Ile Ser Phe Ser Phe Lys Gly Ile Lys Phe Ser Lys
        115                 120                 125

Gly Lys Tyr Lys Cys Val Val Glu Ala Ile Ser Gly Ser Pro Glu Glu
    130                 135                 140

Met Leu Phe Cys Leu Glu Phe Val Ile Leu His Gln Pro Asn Ser Asn
145                 150                 155                 160

<210> SEQ ID NO 22
<211> LENGTH: 160
<212> TYPE: PRT
<213> ORGANISM: Artificial Sequence
<220> FEATURE:
<223> OTHER INFORMATION: Tyrosine to phenylalanine mutation at position
      75 of human MD-2

<400> SEQUENCE: 22

Met Leu Pro Phe Leu Phe Phe Ser Thr Leu Phe Ser Ser Ile Phe Thr
1               5                   10                  15

Glu Ala Gln Lys Gln Tyr Trp Val Cys Asn Ser Ser Asp Ala Ser Ile
            20                  25                  30

Ser Tyr Thr Tyr Cys Asp Lys Met Gln Tyr Pro Ile Ser Ile Asn Val
        35                  40                  45

Asn Pro Cys Ile Glu Leu Lys Arg Ser Lys Gly Leu Leu His Ile Phe
    50                  55                  60

Tyr Ile Pro Arg Arg Asp Leu Lys Gln Leu Phe Phe Asn Leu Tyr Ile
65                  70                  75                  80

Thr Val Asn Thr Met Asn Leu Pro Lys Arg Lys Glu Val Ile Cys Arg
                85                  90                  95

Gly Ser Asp Asp Asp Tyr Ser Phe Cys Arg Ala Leu Lys Gly Glu Thr
            100                 105                 110

Val Asn Thr Thr Ile Ser Phe Ser Phe Lys Gly Ile Lys Phe Ser Lys
        115                 120                 125

Gly Lys Tyr Lys Cys Val Val Glu Ala Ile Ser Gly Ser Pro Glu Glu
    130                 135                 140

Met Leu Phe Cys Leu Glu Phe Val Ile Leu His Gln Pro Asn Ser Asn
145                 150                 155                 160

<210> SEQ ID NO 23
<211> LENGTH: 160
<212> TYPE: PRT
<213> ORGANISM: Artificial Sequence
<220> FEATURE:
<223> OTHER INFORMATION: Tyrosine to phenylalanine mutation at position
      79 of human MD-2

<400> SEQUENCE: 23

Met Leu Pro Phe Leu Phe Phe Ser Thr Leu Phe Ser Ser Ile Phe Thr
1               5                   10                  15

Glu Ala Gln Lys Gln Tyr Trp Val Cys Asn Ser Ser Asp Ala Ser Ile
            20                  25                  30

Ser Tyr Thr Tyr Cys Asp Lys Met Gln Tyr Pro Ile Ser Ile Asn Val
        35                  40                  45

Asn Pro Cys Ile Glu Leu Lys Arg Ser Lys Gly Leu Leu His Ile Phe
    50                  55                  60

Tyr Ile Pro Arg Arg Asp Leu Lys Gln Leu Tyr Phe Asn Leu Phe Ile
65                  70                  75                  80

Thr Val Asn Thr Met Asn Leu Pro Lys Arg Lys Glu Val Ile Cys Arg
                85                  90                  95

Gly Ser Asp Asp Asp Tyr Ser Phe Cys Arg Ala Leu Lys Gly Glu Thr
            100                 105                 110

Val Asn Thr Thr Ile Ser Phe Ser Phe Lys Gly Ile Lys Phe Ser Lys
        115                 120                 125

Gly Lys Tyr Lys Cys Val Val Glu Ala Ile Ser Gly Ser Pro Glu Glu
    130                 135                 140

Met Leu Phe Cys Leu Glu Phe Val Ile Leu His Gln Pro Asn Ser Asn
145                 150                 155                 160

<210> SEQ ID NO 24
<211> LENGTH: 160
<212> TYPE: PRT
<213> ORGANISM: Artificial Sequence
<220> FEATURE:
<223> OTHER INFORMATION: Tyrosine to phenylalanine mutation at position
      102 of human MD-2

<400> SEQUENCE: 24

Met Leu Pro Phe Leu Phe Phe Ser Thr Leu Phe Ser Ser Ile Phe Thr
1               5                   10                  15

Glu Ala Gln Lys Gln Tyr Trp Val Cys Asn Ser Ser Asp Ala Ser Ile
            20                  25                  30

Ser Tyr Thr Tyr Cys Asp Lys Met Gln Tyr Pro Ile Ser Ile Asn Val
        35                  40                  45

```
Asn Pro Cys Ile Glu Leu Lys Arg Ser Lys Gly Leu Leu His Ile Phe
 50                  55                  60

Tyr Ile Pro Arg Arg Asp Leu Lys Gln Leu Tyr Phe Asn Leu Tyr Ile
 65                  70                  75                  80

Thr Val Asn Thr Met Asn Leu Pro Lys Arg Lys Glu Val Ile Cys Arg
                 85                  90                  95

Gly Ser Asp Asp Asp Phe Ser Phe Cys Arg Ala Leu Lys Gly Glu Thr
                100                 105                 110

Val Asn Thr Thr Ile Ser Phe Ser Phe Lys Gly Ile Lys Phe Ser Lys
                115                 120                 125

Gly Lys Tyr Lys Cys Val Val Glu Ala Ile Ser Gly Ser Pro Glu Glu
            130                 135                 140

Met Leu Phe Cys Leu Glu Phe Val Ile Leu His Gln Pro Asn Ser Asn
145                 150                 155                 160

<210> SEQ ID NO 25
<211> LENGTH: 160
<212> TYPE: PRT
<213> ORGANISM: Artificial Sequence
<220> FEATURE:
<223> OTHER INFORMATION: Tyrosine to phenylalanine mutation at position
      131 of human MD-2

<400> SEQUENCE: 25

Met Leu Pro Phe Leu Phe Phe Ser Thr Leu Phe Ser Ser Ile Phe Thr
  1               5                  10                  15

Glu Ala Gln Lys Gln Tyr Trp Val Cys Asn Ser Ser Asp Ala Ser Ile
                 20                  25                  30

Ser Tyr Thr Tyr Cys Asp Lys Met Gln Tyr Pro Ile Ser Ile Asn Val
             35                  40                  45

Asn Pro Cys Ile Glu Leu Lys Arg Ser Lys Gly Leu Leu His Ile Phe
 50                  55                  60

Tyr Ile Pro Arg Arg Asp Leu Lys Gln Leu Tyr Phe Asn Leu Tyr Ile
 65                  70                  75                  80

Thr Val Asn Thr Met Asn Leu Pro Lys Arg Lys Glu Val Ile Cys Arg
                 85                  90                  95

Gly Ser Asp Asp Asp Tyr Ser Phe Cys Arg Ala Leu Lys Gly Glu Thr
                100                 105                 110

Val Asn Thr Thr Ile Ser Phe Ser Phe Lys Gly Ile Lys Phe Ser Lys
                115                 120                 125

Gly Lys Phe Lys Cys Val Val Glu Ala Ile Ser Gly Ser Pro Glu Glu
            130                 135                 140

Met Leu Phe Cys Leu Glu Phe Val Ile Leu His Gln Pro Asn Ser Asn
145                 150                 155                 160

<210> SEQ ID NO 26
<211> LENGTH: 160
<212> TYPE: PRT
<213> ORGANISM: Artificial Sequence
<220> FEATURE:
<223> OTHER INFORMATION: Tyrosine to phenylalanine mutation at position
      22 and 131 of human MD-2

<400> SEQUENCE: 26

Met Leu Pro Phe Leu Phe Phe Ser Thr Leu Phe Ser Ser Ile Phe Thr
  1               5                  10                  15

Glu Ala Gln Lys Gln Phe Trp Val Cys Asn Ser Ser Asp Ala Ser Ile
                 20                  25                  30
```

```
Ser Tyr Thr Tyr Cys Asp Lys Met Gln Tyr Pro Ile Ser Ile Asn Val
            35                  40                  45

Asn Pro Cys Ile Glu Leu Lys Arg Ser Lys Gly Leu Leu His Ile Phe
         50                  55                  60

Tyr Ile Pro Arg Arg Asp Leu Lys Gln Leu Tyr Phe Asn Leu Tyr Ile
 65                  70                  75                  80

Thr Val Asn Thr Met Asn Leu Pro Lys Arg Lys Glu Val Ile Cys Arg
                 85                  90                  95

Gly Ser Asp Asp Tyr Ser Phe Cys Arg Ala Leu Lys Gly Glu Thr
             100                 105                 110

Val Asn Thr Thr Ile Ser Phe Ser Phe Lys Gly Ile Lys Phe Ser Lys
             115                 120                 125

Gly Lys Phe Lys Cys Val Val Glu Ala Ile Ser Gly Ser Pro Glu Glu
         130                 135                 140

Met Leu Phe Cys Leu Glu Phe Val Ile Leu His Gln Pro Asn Ser Asn
145                 150                 155                 160

<210> SEQ ID NO 27
<211> LENGTH: 160
<212> TYPE: PRT
<213> ORGANISM: Homo sapiens

<400> SEQUENCE: 27

Met Leu Pro Phe Leu Phe Phe Ser Thr Leu Phe Ser Ser Ile Phe Thr
 1               5                  10                  15

Glu Ala Gln Lys Gln Tyr Trp Val Cys Asn Ser Ser Asp Ala Ser Ile
                 20                  25                  30

Ser Tyr Thr Tyr Cys Asp Lys Met Gln Tyr Pro Ile Ser Ile Asn Val
            35                  40                  45

Asn Pro Cys Ile Glu Leu Lys Gly Ser Lys Gly Leu Leu His Ile Phe
         50                  55                  60

Tyr Ile Pro Arg Arg Asp Leu Lys Gln Leu Tyr Phe Asn Leu Tyr Ile
 65                  70                  75                  80

Thr Val Asn Thr Met Asn Leu Pro Lys Arg Lys Glu Val Ile Cys Arg
                 85                  90                  95

Gly Ser Asp Asp Tyr Ser Phe Cys Arg Ala Leu Lys Gly Glu Thr
             100                 105                 110

Val Asn Thr Thr Ile Ser Phe Ser Phe Lys Gly Ile Lys Phe Ser Lys
             115                 120                 125

Gly Lys Tyr Lys Cys Val Val Glu Ala Ile Ser Gly Ser Pro Glu Glu
         130                 135                 140

Met Leu Phe Cys Leu Glu Phe Val Ile Leu His Gln Pro Asn Ser Asn
145                 150                 155                 160

<210> SEQ ID NO 28
<211> LENGTH: 129
<212> TYPE: PRT
<213> ORGANISM: Artificial Sequence
<220> FEATURE:
<223> OTHER INFORMATION: Consensus

<400> SEQUENCE: 28

Met Leu Pro Phe Leu Phe Phe Ser Thr Leu Phe Ser Ser Ile Phe Thr
 1               5                  10                  15

Glu Ala Gln Lys Gln Tyr Trp Val Cys Asn Ser Ser Asp Ala Ser Ile
                 20                  25                  30

Ser Tyr Thr Tyr Cys Arg Asp Leu Lys Gln Leu Tyr Phe Asn Leu Tyr
```

```
                35                  40                  45
Ile Thr Val Asn Thr Met Asn Leu Pro Lys Arg Lys Glu Val Ile Cys
    50                  55                  60

Arg Gly Ser Asp Asp Asp Tyr Ser Phe Cys Arg Ala Leu Lys Gly Glu
65                  70                  75                  80

Thr Val Asn Thr Thr Ile Ser Phe Ser Phe Lys Gly Ile Lys Phe Ser
                85                  90                  95

Lys Gly Lys Tyr Lys Cys Val Val Glu Ala Ile Ser Gly Ser Pro Glu
                100                 105                 110

Glu Met Leu Phe Cys Leu Glu Phe Val Ile Leu His Gln Pro Asn Ser
                115                 120                 125

Asn

<210> SEQ ID NO 29
<211> LENGTH: 20
<212> TYPE: DNA
<213> ORGANISM: Homo sapiens

<400> SEQUENCE: 29
tctggcaacc ctagtctgct                                                 20

<210> SEQ ID NO 30
<211> LENGTH: 20
<212> TYPE: DNA
<213> ORGANISM: Homo sapiens

<400> SEQUENCE: 30
gcttccacat gtcctcacaa                                                 20

<210> SEQ ID NO 31
<211> LENGTH: 20
<212> TYPE: DNA
<213> ORGANISM: Homo sapiens

<400> SEQUENCE: 31
atccagctcc ttccaggatt                                                 20

<210> SEQ ID NO 32
<211> LENGTH: 20
<212> TYPE: DNA
<213> ORGANISM: Homo sapiens

<400> SEQUENCE: 32
acacacccac cctctctttg                                                 20
```